(12) United States Patent
Nawana et al.

(10) Patent No.: US 11,923,068 B2
(45) Date of Patent: Mar. 5, 2024

(54) SYSTEMS AND METHODS FOR SURGICAL AND INTERVENTIONAL PLANNING, SUPPORT, POST-OPERATIVE FOLLOW-UP, AND FUNCTIONAL RECOVERY TRACKING

(71) Applicant: DePuy Synthes Products, Inc., Raynham, MA (US)

(72) Inventors: Namal Nawana, Weston, MA (US); Michael Gorhan, Raynham, MA (US); William J. Frasier, New Bedford, MA (US); William C. Horton, Duxbury, MA (US); Mark T. Hall, Bridgewater, MA (US); Matthew Parsons, Dartmouth, MA (US); Jennifer DiPietro, North Easton, MA (US); Christopher Nordstrom, Boston, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 929 days.

(21) Appl. No.: 16/214,947

(22) Filed: Dec. 10, 2018

(65) Prior Publication Data

US 2019/0110784 A1    Apr. 18, 2019

Related U.S. Application Data

(63) Continuation of application No. 14/734,359, filed on Jun. 9, 2015, now Pat. No. 10,166,019, which is a
(Continued)

(51) Int. Cl.
*G16H 30/20* (2018.01)
*A61B 5/00* (2006.01)
(Continued)

(52) U.S. Cl.
CPC .......... *G16H 30/20* (2018.01); *A61B 5/0022* (2013.01); *A61B 5/1118* (2013.01);
(Continued)

(58) Field of Classification Search
CPC ........ G16H 30/20; G16H 20/40; G16H 70/20; G16H 10/20; G16H 40/63; G16H 40/20;
(Continued)

(56) References Cited

U.S. PATENT DOCUMENTS 4,722,056 A    1/1988  Roberts et al.
4,737,972 A    4/1988  Schoolman
(Continued)

FOREIGN PATENT DOCUMENTS

EP    0 812 441 A1    12/1997
EP    1 028 659 A1     8/2000
(Continued)

OTHER PUBLICATIONS

Japanese Office Action for JP Application No. 2020-005047 dated Jan. 26, 2021.
(Continued)

*Primary Examiner* — Peter H Choi
*Assistant Examiner* — Chad A Newton
(74) *Attorney, Agent, or Firm* — Mintz Levin Cohn Ferris Glovsky and Popeo, P.C.

(57) ABSTRACT

Various systems and methods are provided for surgical and interventional planning, support, post-operative follow-up, and functional recovery tracking. In general, a patient can be tracked throughout medical treatment including through initial onset of symptoms, diagnosis, non-surgical treatment, surgical treatment, and recovery from the surgical treatment. In one embodiment, a patient and one or more medical professionals involved with treating the patient can electronically access a comprehensive treatment planning, sup-
(Continued)

port, and review system. The system can provide recommendations regarding diagnosis, non-surgical treatment, surgical treatment, and recovery from the surgical treatment based on data gathered from the patient and the medical professional(s). The system can manage the tracking of multiple patients, thereby allowing for data comparison between similar aspects of medical treatments and for learning over time through continual data gathering, analysis, and assimilation to decision-making algorithms.

16 Claims, 40 Drawing Sheets

Related U.S. Application Data continuation of application No. 14/031,761, filed on Sep. 19, 2013, now Pat. No. 9,129,054, which is a continuation of application No. 13/803,763, filed on Mar. 14, 2013, now abandoned.

(60) Provisional application No. 61/739,514, filed on Dec. 19, 2012, provisional application No. 61/702,073, filed on Sep. 17, 2012.

(51) Int. Cl.

| | | |
|---|---|---|
| *A61B 5/11* | (2006.01) | |
| *A61B 6/00* | (2006.01) | |
| *A61B 8/08* | (2006.01) | |
| *A61B 17/02* | (2006.01) | |
| *A61B 17/50* | (2006.01) | |
| *A61B 34/00* | (2016.01) | |
| *A61B 34/10* | (2016.01) | |
| *A61B 34/20* | (2016.01) | |
| *G01L 5/00* | (2006.01) | |
| *G06Q 10/00* | (2023.01) | |
| *G06Q 10/10* | (2023.01) | |
| *G09B 23/28* | (2006.01) | |
| *G16H 10/20* | (2018.01) | |
| *G16H 20/40* | (2018.01) | |
| *G16H 40/20* | (2018.01) | |
| *G16H 40/40* | (2018.01) | |
| *G16H 40/63* | (2018.01) | |
| *G16H 50/20* | (2018.01) | |
| *G16H 50/50* | (2018.01) | |
| *G16H 50/70* | (2018.01) | |
| *G16H 70/20* | (2018.01) | |
| *G16Z 99/00* | (2019.01) | |
| *A61B 10/00* | (2006.01) | |
| *A61B 17/00* | (2006.01) | |
| *A61B 90/00* | (2016.01) | |
| *A61B 90/50* | (2016.01) | |
| *A61B 90/98* | (2016.01) | |

(52) U.S. Cl.
CPC .......... *A61B 5/4509* (2013.01); *A61B 5/4566* (2013.01); *A61B 5/4571* (2013.01); *A61B 5/4824* (2013.01); *A61B 5/4833* (2013.01); *A61B 5/4848* (2013.01); *A61B 5/7282* (2013.01); *A61B 5/742* (2013.01); *A61B 5/746* (2013.01); *A61B 5/7475* (2013.01); *A61B 6/485* (2013.01); *A61B 8/08* (2013.01); *A61B 17/02* (2013.01); *A61B 17/025* (2013.01); *A61B 17/50* (2013.01); *A61B 34/10* (2016.02); *A61B 34/20* (2016.02); *A61B 34/25* (2016.02); *G01L 5/00* (2013.01); *G06Q 10/00* (2013.01); *G06Q 10/10* (2013.01); *G09B 23/28* (2013.01); *G16H 10/20* (2018.01); *G16H 20/40* (2018.01); *G16H 40/20* (2018.01); *G16H 40/40* (2018.01); *G16H 40/63* (2018.01); *G16H 50/20* (2018.01); *G16H 50/50* (2018.01); *G16H 50/70* (2018.01); *G16H 70/20* (2018.01); *G16Z 99/00* (2019.02); *A61B 6/4494* (2013.01); *A61B 6/506* (2013.01); *A61B 2010/009* (2013.01); *A61B 2010/0093* (2013.01); *A61B 2017/00115* (2013.01); *A61B 2017/00119* (2013.01); *A61B 2017/0262* (2013.01); *A61B 2034/101* (2016.02); *A61B 2034/105* (2016.02); *A61B 2034/2051* (2016.02); *A61B 2034/2055* (2016.02); *A61B 2034/2057* (2016.02); *A61B 2034/252* (2016.02); *A61B 2034/254* (2016.02); *A61B 2034/256* (2016.02); *A61B 2090/365* (2016.02); *A61B 2090/502* (2016.02); *A61B 90/98* (2016.02)

(58) Field of Classification Search
CPC ........ G16H 40/40; G16H 50/50; G16H 50/70; G16H 50/20; G16Z 99/00; A61B 8/08; A61B 17/025; A61B 34/25; A61B 34/10; A61B 34/20; A61B 5/4571; A61B 17/50; A61B 5/1118; A61B 5/0022; A61B 5/4509; A61B 5/4566; A61B 5/4824; A61B 5/4833; A61B 5/4848; A61B 5/7282; A61B 5/742; A61B 5/746; A61B 5/7475; A61B 6/485; A61B 17/02; A61B 2017/0262; A61B 2034/105; A61B 2034/252; A61B 2034/101; A61B 2034/2055; A61B 2034/2057; A61B 2034/254; A61B 2034/256; A61B 2010/009; A61B 2017/00119; A61B 2010/0093; A61B 2017/00115; A61B 6/4494; A61B 6/506; G06Q 10/10; G06Q 10/00; G01L 5/00
See application file for complete search history.

(56) References Cited

U.S. PATENT DOCUMENTS

| | | |
|---|---|---|
| 4,985,678 A | 1/1991 | Gangarosa et al. |
| 5,239,716 A | 8/1993 | Fisk |
| 5,488,001 A | 1/1996 | Brotherton |
| 5,491,510 A | 2/1996 | Gove |
| 5,510,077 A | 4/1996 | Dinh et al. |
| 5,554,182 A | 9/1996 | Dinh et al. |
| 5,577,503 A | 11/1996 | Bonutti |
| 5,578,051 A | 11/1996 | Mirza |
| 5,583,758 A | 12/1996 | McIlroy et al. |
| 5,591,227 A | 1/1997 | Dinh et al. |
| 5,594,638 A | 1/1997 | Iliff |
| 5,613,254 A | 3/1997 | Clayman et al. |
| 5,657,255 A | 8/1997 | Fink et al. |
| 5,660,176 A | 8/1997 | Iliff |
| 5,697,368 A | 12/1997 | Luber et al. |
| 5,711,297 A | 1/1998 | Iliff |
| 5,724,968 A | 3/1998 | Iliff |
| 5,740,802 A | 4/1998 | Nafis et al. |
| 5,765,561 A | 6/1998 | Chen et al. |
| 5,832,488 A | 11/1998 | Eberhardt |
| 5,860,917 A | 1/1999 | Comanor et al. |
| 5,868,669 A | 2/1999 | Iliff |
| 5,878,746 A | 3/1999 | Lemelson et al. |
| 5,903,889 A | 5/1999 | de la Huerga et al. |
| 5,908,383 A | 6/1999 | Brynjestad |
| 5,910,107 A | 6/1999 | Iliff |
| 5,930,741 A | 7/1999 | Kramer |
| 5,935,060 A | 8/1999 | Iliff |
| 5,940,802 A | 8/1999 | Hildebrand et al. |

(56) References Cited

U.S. PATENT DOCUMENTS

| | | | |
|---|---|---|---|
| 5,953,704 A | 9/1999 | McIlroy et al. |
| 5,963,891 A | 10/1999 | Walker et al. |
| 5,970,499 A | 10/1999 | Smith et al. |
| 5,984,870 A | 11/1999 | Giger et al. |
| 5,993,386 A | 11/1999 | Ericsson |
| 5,996,889 A | 12/1999 | Fuchs et al. |
| 5,997,528 A | 12/1999 | Bisch et al. |
| 6,000,828 A | 12/1999 | Leet |
| 6,003,020 A | 12/1999 | Hazlehurst et al. |
| 6,014,626 A | 1/2000 | Cohen |
| 6,021,404 A | 2/2000 | Moukheibir |
| 6,022,315 A | 2/2000 | Iliff |
| 6,029,138 A | 2/2000 | Khorasani et al. |
| 6,032,119 A | 2/2000 | Brown et al. |
| 6,032,120 A | 2/2000 | Rock et al. |
| 6,035,228 A | 3/2000 | Yanof et al. |
| 6,039,688 A | 3/2000 | Douglas et al. |
| 6,047,203 A | 4/2000 | Sackner et al. |
| 6,047,259 A | 4/2000 | Campbell et al. |
| 6,063,026 A | 5/2000 | Schauss et al. |
| 6,063,028 A | 5/2000 | Luciano |
| 6,067,523 A | 5/2000 | Bair et al. |
| 6,071,236 A | 6/2000 | Iliff |
| 6,074,345 A | 6/2000 | van Oostrom et al. |
| 6,076,166 A | 6/2000 | Moshfeghi et al. |
| 6,081,786 A | 6/2000 | Barry et al. |
| 6,090,044 A | 7/2000 | Bishop et al. |
| 6,095,591 A | 8/2000 | Matsuyama et al. |
| 6,106,460 A | 8/2000 | Panescu et al. |
| 6,108,305 A | 8/2000 | Charny et al. |
| 6,108,635 A | 8/2000 | Herren et al. |
| 6,108,703 A | 8/2000 | Leighton et al. |
| 6,113,540 A | 9/2000 | Iliff |
| 6,117,076 A | 9/2000 | Cassidy |
| 6,122,351 A | 9/2000 | Schlueter, Jr. et al. |
| 6,126,595 A | 10/2000 | Amano et al. |
| 6,126,596 A | 10/2000 | Freedman |
| 6,129,681 A | 10/2000 | Kuroda et al. |
| 6,132,218 A | 10/2000 | Benja-Athon |
| 6,135,949 A | 10/2000 | Russo et al. |
| 6,139,494 A | 10/2000 | Cairnes |
| 6,149,585 A | 11/2000 | Gray |
| 6,151,581 A | 11/2000 | Kraftson et al. |
| 6,157,914 A | 12/2000 | Seto et al. |
| 6,161,095 A | 12/2000 | Brown |
| 6,177,940 B1 | 1/2001 | Bond et al. |
| 6,183,494 B1 | 2/2001 | Amor et al. |
| 6,188,988 B1 | 2/2001 | Barry et al. |
| 6,196,970 B1 | 3/2001 | Brown |
| 6,206,829 B1 | 3/2001 | Iliff |
| 6,212,519 B1 | 4/2001 | Segal |
| 6,223,137 B1 | 4/2001 | McCay et al. |
| 6,223,164 B1 | 4/2001 | Seare et al. |
| 6,224,548 B1 | 5/2001 | Gopinathan et al. |
| 6,224,549 B1 | 5/2001 | Drongelen |
| 6,233,137 B1 | 5/2001 | Kolos et al. |
| 6,234,964 B1 | 5/2001 | Iliff |
| 6,247,004 B1 | 6/2001 | Moukheibir |
| 6,248,063 B1 | 6/2001 | Barnhill et al. |
| 6,260,220 B1 | 7/2001 | Lamb et al. |
| 6,261,239 B1 | 7/2001 | Abraham-Fuchs et al. |
| 6,270,456 B1 | 8/2001 | Iliff |
| 6,270,457 B1 | 8/2001 | Bardy |
| 6,272,469 B1 | 8/2001 | Koritzinsky et al. |
| 6,273,854 B1 | 8/2001 | Kane et al. |
| 6,277,070 B1 | 8/2001 | Kane et al. |
| 6,280,380 B1 | 8/2001 | Bardy |
| 6,283,761 B1 | 9/2001 | Joao |
| 6,283,923 B1 | 9/2001 | Finkelstein et al. |
| 6,289,238 B1 | 9/2001 | Besson et al. |
| 6,290,646 B1 | 9/2001 | Cosentino et al. |
| 6,305,377 B1 | 10/2001 | Portwood et al. |
| 6,317,731 B1 | 11/2001 | Luciano |
| 6,338,713 B1 | 1/2002 | Chamoun et al. |
| 6,347,329 B1 | 2/2002 | Evans |
| 6,371,123 B1 | 4/2002 | Stark et al. |
| 6,381,576 B1 | 4/2002 | Gilbert |
| 6,383,136 B1 | 5/2002 | Jordan |
| 6,387,066 B1 | 5/2002 | Whiteside |
| 6,394,811 B2 | 5/2002 | Finitzo et al. |
| 6,401,072 B1 | 6/2002 | Haudenschild et al. |
| 6,409,660 B1 | 6/2002 | Sjoqvist |
| 6,409,662 B1 | 6/2002 | Lloyd et al. |
| 6,413,212 B1 | 7/2002 | Raab |
| 6,416,471 B1 | 7/2002 | Kumar et al. |
| 6,434,531 B1 | 8/2002 | Lancelot et al. |
| 6,440,068 B1 | 8/2002 | Brown et al. |
| 6,450,955 B1 | 9/2002 | Brown et al. |
| 6,450,956 B1 | 9/2002 | Rappaport et al. |
| 6,454,705 B1 | 9/2002 | Cosentino et al. |
| 6,454,768 B1 | 9/2002 | Jackson |
| 6,463,417 B1 | 10/2002 | Schoenberg |
| 6,468,210 B2 | 10/2002 | Iliff |
| 6,475,143 B2 | 11/2002 | Iliff |
| 6,482,156 B2 | 11/2002 | Iliff |
| 6,484,144 B2 | 11/2002 | Martin et al. |
| 6,484,334 B1 | 11/2002 | Borders et al. |
| 6,485,418 B2 | 11/2002 | Yasushi et al. |
| 6,487,520 B1 | 11/2002 | Kurtzberg et al. |
| 6,491,629 B1 | 12/2002 | Bousseljot et al. |
| 6,494,829 B1 | 12/2002 | New, Jr. et al. |
| 6,497,657 B2 | 12/2002 | Nunome |
| 6,514,219 B1 | 2/2003 | Guimond et al. |
| 6,520,910 B1 | 2/2003 | Kohls |
| 6,523,009 B1 | 2/2003 | Wilkins |
| 6,524,239 B1 | 2/2003 | Reed et al. |
| 6,524,241 B2 | 2/2003 | Iliff |
| 6,527,712 B1 | 3/2003 | Brown et al. |
| 6,527,713 B2 | 3/2003 | Iliff |
| 6,533,724 B2 | 3/2003 | McNair |
| 6,535,756 B1 | 3/2003 | Simon et al. |
| 6,551,243 B2 | 4/2003 | Bocionek et al. |
| 6,558,321 B1 | 5/2003 | Burd et al. |
| 6,560,476 B1 | 5/2003 | Pelletier et al. |
| 6,561,992 B1 | 5/2003 | Eberhart et al. |
| 6,569,093 B2 | 5/2003 | Iliff |
| 6,569,095 B2 | 5/2003 | Eggers |
| 6,579,231 B1 | 6/2003 | Phipps |
| 6,579,888 B2 | 6/2003 | Reitberg |
| 6,581,038 B1 | 6/2003 | Mahran |
| 6,584,445 B2 | 6/2003 | Papageorge |
| 6,599,241 B1 | 7/2003 | Murphy |
| 6,602,191 B2 | 8/2003 | Quy |
| 6,605,038 B1 | 8/2003 | Teller et al. |
| 6,607,480 B1 | 8/2003 | Bousseljot et al. |
| 6,607,482 B1 | 8/2003 | Teitelbaum |
| 6,612,985 B2 | 9/2003 | Eiffert et al. |
| 6,612,986 B2 | 9/2003 | Doi et al. |
| 6,614,453 B1 | 9/2003 | Suri et al. |
| 6,622,032 B1 | 9/2003 | Robinson et al. |
| 6,622,036 B1 | 9/2003 | Suffin |
| 6,635,016 B2 | 10/2003 | Finkelshteins |
| 6,638,218 B2 | 10/2003 | Bulat |
| 6,641,532 B2 | 11/2003 | Iliff |
| 6,644,322 B2 | 11/2003 | Webb |
| 6,656,115 B1 | 12/2003 | Miyazaki et al. |
| 6,656,120 B2 | 12/2003 | Lee et al. |
| 6,658,396 B1 | 12/2003 | Tang et al. |
| 6,659,968 B1 | 12/2003 | McClure |
| 6,669,630 B1 | 12/2003 | Joliat et al. |
| 6,669,631 B2 | 12/2003 | Norris et al. |
| 6,671,563 B1 | 12/2003 | Engelson et al. |
| 6,675,032 B2 | 1/2004 | Chen et al. |
| 6,678,703 B2 | 1/2004 | Rothschild et al. |
| 6,684,276 B2 | 1/2004 | Walker et al. |
| 6,687,685 B1 | 2/2004 | Sadeghi et al. |
| 6,692,436 B1 | 2/2004 | Bluth et al. |
| 6,694,162 B2 | 2/2004 | Hartlep |
| 6,694,168 B2 | 2/2004 | Traxel et al. |
| 6,697,664 B2 | 2/2004 | Kienzle, III et al. |
| 6,701,174 B1 | 3/2004 | Krause et al. |
| 6,711,432 B1 | 3/2004 | Krause et al. |
| 6,723,045 B2 | 4/2004 | Cosentino et al. |
| 6,725,082 B2 | 4/2004 | Sati et al. |

(56) References Cited

U.S. PATENT DOCUMENTS

| | | |
|---|---|---|
| 6,725,209 B1 | 4/2004 | Iliff |
| 6,730,027 B2 | 5/2004 | Iliff |
| 6,746,399 B2 | 6/2004 | Iliff |
| 6,748,353 B1 | 6/2004 | Iliff |
| 6,751,499 B2 | 6/2004 | Lange et al. |
| 6,754,655 B1 | 6/2004 | Segal |
| 6,757,898 B1 | 6/2004 | Ilsen et al. |
| 6,764,447 B2 | 7/2004 | Iliff |
| 6,767,325 B2 | 7/2004 | Iliff |
| 6,770,029 B2 | 8/2004 | Iliff |
| 6,773,396 B2 | 8/2004 | Flach et al. |
| 6,802,810 B2 | 10/2004 | Ciarniello et al. |
| 6,804,656 B1 | 10/2004 | Rosenfeld et al. |
| 6,807,531 B1 | 10/2004 | Kanai |
| 6,810,349 B2 | 10/2004 | Westerterp et al. |
| 6,817,979 B2 | 11/2004 | Nihtila |
| 6,817,980 B2 | 11/2004 | Iliff |
| 6,819,785 B1 | 11/2004 | Vining et al. |
| 6,827,670 B1 | 12/2004 | Stark et al. |
| 6,834,436 B2 | 12/2004 | Townsend et al. |
| 6,842,796 B2 | 1/2005 | Zweig et al. |
| 6,847,336 B1 | 1/2005 | Lemelson et al. |
| 6,849,045 B2 | 2/2005 | Iliff |
| 6,850,889 B1 | 2/2005 | Zayas, Jr. |
| 6,859,660 B2 | 2/2005 | Vilsmeier |
| 6,864,796 B2 | 3/2005 | Lehrman et al. |
| 6,866,629 B2 | 3/2005 | Bardy |
| 6,887,201 B2 | 5/2005 | Bardy |
| 6,896,660 B2 | 5/2005 | Jelliffe et al. |
| 6,903,657 B2 | 6/2005 | Kwoen |
| 6,911,464 B2 | 6/2005 | Man et al. |
| 6,911,916 B1 | 6/2005 | Wang et al. |
| 6,917,829 B2 | 7/2005 | Kwong |
| 6,917,926 B2 | 7/2005 | Chen et al. |
| 6,920,347 B2 | 7/2005 | Simon et al. |
| 6,929,607 B2 | 8/2005 | Lipman |
| 6,941,951 B2 | 9/2005 | Hubert et al. |
| 6,945,934 B2 | 9/2005 | Bardy |
| 6,955,647 B2 | 10/2005 | Rice |
| 6,957,102 B2 | 10/2005 | Silver et al. |
| 6,957,187 B1 | 10/2005 | Kameda |
| 6,966,081 B1 | 11/2005 | Sharps et al. |
| 6,975,230 B1 | 12/2005 | Brilman |
| 6,988,075 B1 | 1/2006 | Hacker |
| 6,988,088 B1 | 1/2006 | Miikkulainen et al. |
| 7,011,629 B2 | 3/2006 | Bulat |
| 7,020,508 B2 | 3/2006 | Stivoric et al. |
| 7,024,369 B1 | 4/2006 | Brown et al. |
| 7,065,528 B2 | 6/2006 | Herz et al. |
| 7,130,676 B2 | 10/2006 | Barrick |
| 7,133,879 B1 | 11/2006 | Goldsmith et al. |
| 7,180,014 B2 | 2/2007 | Farber et al. |
| 7,181,375 B2 | 2/2007 | Rao et al. |
| 7,194,120 B2 | 3/2007 | Wicker et al. |
| 7,194,301 B2 | 3/2007 | Jenkins et al. |
| 7,210,240 B2 | 5/2007 | Townsend et al. |
| 7,212,850 B2 | 5/2007 | Prystowsky et al. |
| 7,215,991 B2 | 5/2007 | Besson et al. |
| 7,216,385 B2 | 5/2007 | Hill |
| 7,223,235 B2 | 5/2007 | Brown |
| 7,223,236 B2 | 5/2007 | Brown |
| 7,228,315 B2 | 6/2007 | Finitzo et al. |
| 7,234,180 B2 | 6/2007 | Horton et al. |
| 7,234,937 B2 | 6/2007 | Sachdeva et al. |
| 7,254,566 B2 | 8/2007 | Merkle |
| 7,256,708 B2 | 8/2007 | Rosenfeld et al. |
| 7,261,690 B2 | 8/2007 | Teller et al. |
| 7,285,090 B2 | 10/2007 | Stivoric et al. |
| 7,287,031 B1 | 10/2007 | Karpf et al. |
| 7,290,302 B2 | 11/2007 | Sharps |
| 7,297,108 B2 | 11/2007 | Iliff |
| 7,297,111 B2 | 11/2007 | Iliff |
| 7,300,402 B2 | 11/2007 | Iliff |
| 7,306,560 B2 | 12/2007 | Iliff |
| 7,307,543 B2 | 12/2007 | Rosenfeld et al. |
| 7,313,440 B2 | 12/2007 | Miesel |
| 7,315,825 B2 | 1/2008 | Rosenfeld et al. |
| 7,321,862 B2 | 1/2008 | Rosenfeld et al. |
| 7,330,760 B2 | 2/2008 | Heruth et al. |
| 7,344,496 B2 | 3/2008 | Iliff |
| 7,351,203 B2 | 4/2008 | Jelliffe et al. |
| 7,374,536 B1 | 5/2008 | Taylor |
| 7,379,885 B1 | 5/2008 | Zakim |
| 7,383,197 B1 | 6/2008 | Neuman |
| 7,389,277 B2 | 6/2008 | Chen et al. |
| 7,395,216 B2 | 7/2008 | Rosenfeld et al. |
| 7,398,217 B2 | 7/2008 | Lewis et al. |
| 7,409,354 B2 | 8/2008 | Putnam et al. |
| 7,411,509 B2 | 8/2008 | Rosenfeld et al. |
| 7,412,396 B1 | 8/2008 | Haq |
| 7,418,299 B2 | 8/2008 | Merkle |
| 7,428,494 B2 | 9/2008 | Hasan et al. |
| 7,433,798 B2 | 10/2008 | Townsend et al. |
| 7,433,827 B2 | 10/2008 | Rosenfeld et al. |
| 7,440,904 B2 | 10/2008 | Hasan et al. |
| 7,454,359 B2 | 11/2008 | Rosenfeld et al. |
| 7,454,360 B2 | 11/2008 | Rosenfeld et al. |
| 7,464,021 B1 | 12/2008 | Myers et al. |
| 7,467,094 B2 | 12/2008 | Rosenfeld et al. |
| 7,471,290 B2 | 12/2008 | Wang et al. |
| 7,475,019 B2 | 1/2009 | Rosenfeld et al. |
| 7,492,261 B2 | 2/2009 | Cambre et al. |
| 7,509,264 B2 | 3/2009 | Hasan et al. |
| 7,516,192 B2 | 4/2009 | Brown |
| 7,533,353 B2 | 5/2009 | Dvorak et al. |
| 7,558,738 B1 | 7/2009 | Flatt |
| 7,580,846 B2 | 8/2009 | Chishti et al. |
| 7,587,469 B2 | 9/2009 | Brown |
| 7,593,913 B2 | 9/2009 | Wang et al. |
| 7,617,078 B2 | 11/2009 | Rao et al. |
| 7,617,116 B2 | 11/2009 | Amar et al. |
| 7,625,316 B1 | 12/2009 | Amsbury et al. |
| 7,630,947 B2 | 12/2009 | Pandya et al. |
| 7,640,051 B2 | 12/2009 | Krishnan et al. |
| 7,650,321 B2 | 1/2010 | Krishnan et al. |
| 7,653,227 B2 | 1/2010 | Krishnan et al. |
| 7,664,660 B2 | 2/2010 | Korpman et al. |
| 7,672,491 B2 | 3/2010 | Krishnan et al. |
| 7,676,379 B2 | 3/2010 | Kil et al. |
| 7,685,003 B2 | 3/2010 | Hasan et al. |
| 7,689,014 B2 | 3/2010 | Abovitz et al. |
| 7,689,437 B1 | 3/2010 | Teller et al. |
| 7,691,059 B2 | 4/2010 | Bulat |
| 7,693,730 B2 | 4/2010 | Hasan et al. |
| 7,707,047 B2 | 4/2010 | Hasan et al. |
| 7,711,404 B2 | 5/2010 | Rao et al. |
| 7,720,691 B2 | 5/2010 | Hasan et al. |
| 7,729,928 B2 | 6/2010 | Backhaus et al. |
| 7,734,477 B2 | 6/2010 | Bellin et al. |
| 7,744,540 B2 | 6/2010 | Rao et al. |
| 7,769,600 B2 | 8/2010 | Iliff |
| 7,769,605 B2 | 8/2010 | Brown |
| 7,780,595 B2 | 8/2010 | Iliff |
| 7,792,583 B2 | 9/2010 | Miesel et al. |
| 7,799,021 B2 | 9/2010 | Leung et al. |
| 7,805,385 B2 | 9/2010 | Steck et al. |
| 7,831,446 B2 | 11/2010 | Korpman et al. |
| 7,840,420 B2 | 11/2010 | Brown |
| 7,840,511 B2 | 11/2010 | Rosales et al. |
| 7,840,512 B2 | 11/2010 | Pandya et al. |
| 7,844,560 B2 | 11/2010 | Krishnan et al. |
| 7,870,249 B2 | 1/2011 | Brown |
| 7,878,811 B2 | 2/2011 | Earle |
| 7,899,764 B2 | 3/2011 | Martin et al. |
| 7,907,996 B2 | 3/2011 | Prystowsky et al. |
| 7,912,278 B2 | 3/2011 | Fung et al. |
| 7,912,528 B2 | 3/2011 | Krishnan et al. |
| 7,917,377 B2 | 3/2011 | Rao et al. |
| 7,917,478 B2 | 3/2011 | Friedlander et al. |
| 7,918,849 B2 | 4/2011 | Bleich et al. |
| 7,921,017 B2 | 4/2011 | Claus et al. |
| 7,921,186 B2 | 4/2011 | Brown |
| 7,925,521 B2 | 4/2011 | Backhaus et al. |
| 7,953,613 B2 | 5/2011 | Gizewski |

(56) References Cited

U.S. PATENT DOCUMENTS

| | | |
|---|---|---|
| RE42,508 E | 6/2011 | Lewis et al. |
| 7,970,634 B2 | 6/2011 | Backhaus et al. |
| 7,974,677 B2 | 7/2011 | Mire et al. |
| 7,987,001 B2 | 7/2011 | Teichman et al. |
| 7,991,485 B2 | 8/2011 | Zakim |
| 7,993,267 B2 | 8/2011 | Iliff |
| 7,996,444 B2 | 8/2011 | Seemann |
| 8,000,984 B2 | 8/2011 | Hasan et al. |
| 8,015,145 B2 | 9/2011 | Liu et al. |
| 8,019,582 B2 | 9/2011 | Iliff |
| 8,023,706 B2 | 9/2011 | Witte |
| 8,036,912 B2 | 10/2011 | Jensen et al. |
| 8,037,052 B2 | 10/2011 | Kariathungal et al. |
| 8,055,516 B2 | 11/2011 | Iliff |
| 8,060,181 B2 | 11/2011 | Rodriguez Ponce et al. |
| 8,060,378 B2 | 11/2011 | Iliff |
| 8,065,166 B2 | 11/2011 | Maresh et al. |
| 8,066,636 B2 | 11/2011 | Iliff |
| 8,073,707 B2 | 12/2011 | Teller et al. |
| 8,073,710 B2 | 12/2011 | Hasan et al. |
| 8,090,593 B2 | 1/2012 | Backhaus et al. |
| 8,090,596 B2 | 1/2012 | Maresh et al. |
| 8,092,465 B2 | 1/2012 | Metzger et al. |
| 8,095,378 B2 | 1/2012 | Zimmerman et al. |
| 8,095,380 B2 | 1/2012 | Wennberg |
| 8,099,307 B2 | 1/2012 | Maresh et al. |
| 8,105,339 B2 | 1/2012 | Melkent et al. |
| 8,108,228 B2 | 1/2012 | Maresh et al. |
| 8,121,870 B2 | 2/2012 | Maresh et al. |
| 8,126,736 B2 | 2/2012 | Anderson et al. |
| 8,131,563 B2 | 3/2012 | Hasan et al. |
| 8,131,569 B2 | 3/2012 | Maresh et al. |
| 8,145,503 B2 | 3/2012 | Backhaus et al. |
| 8,150,708 B2 | 4/2012 | Kotula et al. |
| 8,160,325 B2 | 4/2012 | Zug et al. |
| 8,161,977 B2 | 4/2012 | Shelton, IV et al. |
| RE43,433 E | 5/2012 | Iliff |
| 8,170,888 B2 | 5/2012 | Silverman |
| 8,193,931 B2 | 6/2012 | Rapaport et al. |
| 8,195,481 B2 | 6/2012 | Backhaus |
| 8,195,483 B2 | 6/2012 | Maresh et al. |
| 8,195,594 B1 | 6/2012 | Bryce |
| 8,200,310 B2 | 6/2012 | Jonckheere et al. |
| RE43,548 E | 7/2012 | Iliff |
| 8,214,224 B2 | 7/2012 | Rao et al. |
| 8,214,225 B2 | 7/2012 | Rao et al. |
| 8,214,234 B2 | 7/2012 | Hasan et al. |
| 8,224,665 B2 | 7/2012 | Morris |
| 8,224,666 B1 | 7/2012 | Watt et al. |
| 8,224,667 B1 | 7/2012 | Miller et al. |
| 8,229,559 B2 | 7/2012 | Westendorp et al. |
| 8,229,760 B2 | 7/2012 | Hasan et al. |
| 8,229,761 B2 | 7/2012 | Backhaus et al. |
| 8,229,780 B2 | 7/2012 | Davidow et al. |
| 8,229,881 B2 | 7/2012 | Pedro et al. |
| 8,243,940 B2 | 8/2012 | Smith |
| 8,255,238 B2 | 8/2012 | Powell et al. |
| 8,260,635 B2 | 9/2012 | Hasan et al. |
| 8,265,949 B2 | 9/2012 | Haddad |
| 8,265,954 B2 | 9/2012 | Hasan et al. |
| 8,265,957 B2 | 9/2012 | Craine |
| 8,271,415 B2 | 9/2012 | Iliff |
| 8,280,750 B2 | 10/2012 | Krishnan et al. |
| 8,287,523 B2 | 10/2012 | Wong et al. |
| 8,301,465 B2 | 10/2012 | Janas, III et al. |
| 8,301,466 B2 | 10/2012 | Lorsch |
| 8,301,467 B2 | 10/2012 | Iliff |
| 8,311,791 B1 | 11/2012 | Avisar |
| 8,311,847 B2 | 11/2012 | Kotula et al. |
| 8,312,057 B2 | 11/2012 | John |
| 8,313,432 B2 | 11/2012 | Chiu et al. |
| 8,321,239 B2 | 11/2012 | Hasan et al. |
| 8,332,466 B1 | 12/2012 | Cha et al. |
| 8,333,696 B2 | 12/2012 | Levendowski et al. |
| 8,335,364 B2 | 12/2012 | Osmundson et al. |
| 8,335,553 B2 | 12/2012 | Rubner et al. |
| 8,337,409 B2 | 12/2012 | Iliff |
| 8,348,847 B2 | 1/2013 | Vezina |
| 8,352,056 B2 | 1/2013 | Lee et al. |
| 8,374,673 B2 | 2/2013 | Adcox et al. |
| 8,376,937 B2 | 2/2013 | Xia et al. |
| 8,380,537 B2 | 2/2013 | Hasan et al. |
| 8,380,542 B2 | 2/2013 | Wons et al. |
| 8,386,278 B2 | 2/2013 | Maresh et al. |
| 8,392,217 B2 | 3/2013 | Iliff |
| 8,392,223 B2 | 3/2013 | Hasan et al. |
| 8,392,342 B2 | 3/2013 | Mangione-Smith |
| 8,394,144 B2 | 3/2013 | Zehavi et al. |
| 8,396,232 B2 | 3/2013 | Thomas |
| 8,398,646 B2 | 3/2013 | Metzger et al. |
| 8,438,041 B2 | 5/2013 | Green, III et al. |
| 8,452,615 B2 | 5/2013 | Abri |
| 8,473,310 B2 | 6/2013 | Hasan et al. |
| 8,484,001 B2 | 7/2013 | Glozman et al. |
| 8,489,418 B2 | 7/2013 | Gustafson et al. |
| 8,489,423 B2 | 7/2013 | Hasan et al. |
| 8,489,424 B2 | 7/2013 | Hasan et al. |
| 8,498,883 B2 | 7/2013 | Lorsch |
| 8,515,778 B2 | 8/2013 | Backhaus |
| 8,532,741 B2 | 9/2013 | Heruth et al. |
| 8,554,697 B2 | 10/2013 | Claus et al. |
| 8,560,346 B2 | 10/2013 | Bundschus et al. |
| 8,568,317 B1 | 10/2013 | Gharib et al. |
| 8,634,904 B2 | 1/2014 | Kaula et al. |
| 8,992,580 B2 | 3/2015 | Bar et al. |
| 9,049,989 B2 | 6/2015 | Crenshaw et al. |
| 9,129,054 B2 | 9/2015 | Nawana et al. |
| 9,636,096 B1 | 5/2017 | Heaton, II et al. |
| 9,700,292 B2 | 7/2017 | Nawana et al. |
| 9,858,721 B2 | 1/2018 | Maimone et al. |
| 9,949,840 B1 | 4/2018 | Smith |
| 9,983,412 B1 | 5/2018 | Fuchs et al. |
| 10,058,338 B2 | 8/2018 | Shoham |
| 10,166,019 B2 | 1/2019 | Nawana et al. |
| 10,595,844 B2 | 3/2020 | Nawana et al. |
| 10,864,047 B2 | 12/2020 | Hagag et al. |
| 11,749,396 B2 | 9/2023 | Nawana et al. |
| 2002/0016994 A1 | 2/2002 | Hand et al. |
| 2002/0082498 A1 | 6/2002 | Wendt et al. |
| 2002/0140694 A1 | 10/2002 | Sauer et al. |
| 2003/0120458 A1 | 6/2003 | Rao et al. |
| 2003/0120514 A1 | 6/2003 | Rao et al. |
| 2003/0125782 A1 | 7/2003 | Streeter |
| 2003/0125988 A1 | 7/2003 | Rao et al. |
| 2003/0126101 A1 | 7/2003 | Rao et al. |
| 2003/0130871 A1 | 7/2003 | Rao et al. |
| 2003/0135275 A1 | 7/2003 | Garcia et al. |
| 2003/0232066 A1 | 12/2003 | Aiache et al. |
| 2004/0015070 A1 | 1/2004 | Liang et al. |
| 2004/0015337 A1 | 1/2004 | Thomas et al. |
| 2004/0044295 A1 | 3/2004 | Reinert et al. |
| 2004/0068187 A1 | 4/2004 | Krause et al. |
| 2004/0077939 A1 | 4/2004 | Graumann |
| 2004/0078236 A1 | 4/2004 | Stoodley et al. |
| 2004/0096864 A1 | 5/2004 | Carroll et al. |
| 2004/0131150 A1 | 7/2004 | Pankratov et al. |
| 2004/0133979 A1* | 7/2004 | Newkirk ............... A61F 5/3761 5/600 |
| 2004/0171924 A1 | 9/2004 | Mire et al. |
| 2004/0254454 A1 | 12/2004 | Kockro |
| 2005/0043621 A1 | 2/2005 | Perlin |
| 2005/0065617 A1 | 3/2005 | Moctezuma de la Barrera et al. |
| 2005/0080333 A1 | 4/2005 | Piron et al. |
| 2005/0102159 A1 | 5/2005 | Mondshine |
| 2005/0159654 A1 | 7/2005 | Rao et al. |
| 2005/0177050 A1 | 8/2005 | Cohen |
| 2005/0177239 A1 | 8/2005 | Steinberg |
| 2005/0201450 A1 | 9/2005 | Volpi |
| 2005/0215867 A1 | 9/2005 | Grigsby et al. |
| 2005/0234740 A1 | 10/2005 | Krishnan et al. |
| 2005/0256390 A1 | 11/2005 | Laux et al. |
| 2005/0277913 A1 | 12/2005 | McCary |
| 2005/0280536 A1 | 12/2005 | Hamilton et al. |
| 2006/0025656 A1 | 2/2006 | Buckner et al. |

(56) References Cited

U.S. PATENT DOCUMENTS

| | | |
|---|---|---|
| 2006/0064017 A1 | 3/2006 | Krishnan et al. |
| 2006/0079752 A1 | 4/2006 | Anderl et al. |
| 2006/0084056 A1 | 4/2006 | Harbeck et al. |
| 2006/0085049 A1 | 4/2006 | Cory et al. |
| 2006/0111933 A1 | 5/2006 | Wheeler |
| 2006/0119621 A1 | 6/2006 | Krier |
| 2006/0176242 A1 | 8/2006 | Jaramaz et al. |
| 2006/0181482 A1 | 8/2006 | Iaquinto |
| 2006/0200010 A1 | 9/2006 | Rosales et al. |
| 2006/0206011 A1 | 9/2006 | Higgins et al. |
| 2006/0241405 A1 | 10/2006 | Leitner et al. |
| 2006/0241972 A1 | 10/2006 | Lang et al. |
| 2006/0247557 A1 | 11/2006 | Coates et al. |
| 2006/0265253 A1 | 11/2006 | Rao et al. |
| 2006/0270913 A1 | 11/2006 | Todd |
| 2006/0282020 A1 | 12/2006 | Bertagnoli et al. |
| 2007/0014452 A1 | 1/2007 | Suresh et al. |
| 2007/0015974 A1 | 1/2007 | Higgins et al. |
| 2007/0015999 A1 | 1/2007 | Heldreth et al. |
| 2007/0022535 A1 | 2/2007 | Yue |
| 2007/0061393 A1 | 3/2007 | Moore |
| 2007/0078678 A1 | 4/2007 | Disilvestro et al. |
| 2007/0080801 A1 | 4/2007 | Weismiller et al. |
| 2007/0106536 A1 | 5/2007 | Moore |
| 2007/0106537 A1 | 5/2007 | Moore |
| 2007/0106750 A1 | 5/2007 | Moore |
| 2007/0106751 A1 | 5/2007 | Moore |
| 2007/0106752 A1 | 5/2007 | Moore |
| 2007/0106753 A1 | 5/2007 | Moore |
| 2007/0106754 A1 | 5/2007 | Moore |
| 2007/0116036 A1 | 5/2007 | Moore |
| 2007/0116037 A1 | 5/2007 | Moore |
| 2007/0136218 A1 | 6/2007 | Bauer et al. |
| 2007/0156453 A1 | 7/2007 | Frielinghaus et al. |
| 2007/0167741 A1 | 7/2007 | Sherman et al. |
| 2007/0168461 A1 | 7/2007 | Moore |
| 2007/0169364 A1 | 7/2007 | Townsend et al. |
| 2007/0192143 A1 | 8/2007 | Krishnan et al. |
| 2007/0192960 A1 | 8/2007 | Jackson |
| 2007/0239491 A1 | 10/2007 | Rao et al. |
| 2007/0251011 A1* | 11/2007 | Matta ............... A61G 13/1205 5/624 |
| 2007/0270680 A1 | 11/2007 | Sheffer et al. |
| 2007/0282195 A1 | 12/2007 | Masini et al. |
| 2007/0287900 A1 | 12/2007 | Breen et al. |
| 2007/0288030 A1 | 12/2007 | Metzger et al. |
| 2008/0009945 A1 | 1/2008 | Pacheco |
| 2008/0040151 A1 | 2/2008 | Moore |
| 2008/0058837 A1* | 3/2008 | Steinberg .......... A61B 17/1671 606/130 |
| 2008/0065098 A1 | 3/2008 | Larkin |
| 2008/0077158 A1 | 3/2008 | Haider et al. |
| 2008/0084833 A1 | 4/2008 | Picard |
| 2008/0114490 A1 | 5/2008 | Jean-Pierre |
| 2008/0120296 A1 | 5/2008 | Kariathungal et al. |
| 2008/0162352 A1 | 7/2008 | Gizewski |
| 2008/0177203 A1 | 7/2008 | von Jako |
| 2008/0177570 A1 | 7/2008 | Craine |
| 2008/0183068 A1 | 7/2008 | Carls et al. |
| 2008/0183074 A1 | 7/2008 | Carls et al. |
| 2008/0188766 A1 | 8/2008 | Gertner |
| 2008/0208813 A1 | 8/2008 | Friedlander et al. |
| 2008/0214928 A1 | 9/2008 | Rosales et al. |
| 2008/0243142 A1 | 10/2008 | Gildenberg |
| 2008/0269596 A1 | 10/2008 | Revie et al. |
| 2008/0275731 A1 | 11/2008 | Rao et al. |
| 2008/0312041 A1 | 12/2008 | Schwabe et al. |
| 2008/0319275 A1 | 12/2008 | Chiu et al. |
| 2009/0008447 A1 | 1/2009 | Godlewski |
| 2009/0018808 A1 | 1/2009 | Bronstein et al. |
| 2009/0037470 A1 | 2/2009 | Schmidt |
| 2009/0105811 A1 | 4/2009 | Dinh et al. |
| 2009/0118714 A1 | 5/2009 | Teodorescu |
| 2009/0118816 A1 | 5/2009 | Kipshidze et al. |
| 2009/0129556 A1 | 5/2009 | Ahn |
| 2009/0172773 A1 | 7/2009 | Moore |
| 2009/0192360 A1 | 7/2009 | Riess et al. |
| 2009/0203973 A1 | 8/2009 | Donoghue et al. |
| 2009/0210383 A1 | 8/2009 | Seemann |
| 2009/0234628 A1 | 9/2009 | Yu et al. |
| 2009/0259487 A1 | 10/2009 | Rao et al. |
| 2009/0299766 A1 | 12/2009 | Friedlander et al. |
| 2009/0306480 A1 | 12/2009 | Protopsaltis |
| 2009/0307681 A1 | 12/2009 | Armado et al. |
| 2010/0013910 A1 | 1/2010 | Farr |
| 2010/0036253 A1 | 2/2010 | Vezina |
| 2010/0036384 A1 | 2/2010 | Gorek et al. |
| 2010/0049547 A1 | 2/2010 | Mirza et al. |
| 2010/0076563 A1 | 3/2010 | Otto et al. |
| 2010/0079356 A1 | 4/2010 | Hoellwarth |
| 2010/0086181 A1 | 4/2010 | Zug et al. |
| 2010/0088095 A1 | 4/2010 | John |
| 2010/0098744 A1 | 4/2010 | Ferris et al. |
| 2010/0109848 A1 | 5/2010 | Blair et al. |
| 2010/0121178 A1 | 5/2010 | Krishnan et al. |
| 2010/0152604 A1 | 6/2010 | Kaula et al. |
| 2010/0171611 A1 | 7/2010 | Gao et al. |
| 2010/0191071 A1 | 7/2010 | Anderson et al. |
| 2010/0191100 A1 | 7/2010 | Anderson et al. |
| 2010/0192300 A1 | 8/2010 | Tannoury et al. |
| 2010/0257674 A1 | 10/2010 | Beall et al. |
| 2010/0262239 A1 | 10/2010 | Boyden et al. |
| 2010/0262435 A1 | 10/2010 | Smith et al. |
| 2010/0274584 A1 | 10/2010 | Kim |
| 2010/0285438 A1 | 11/2010 | Kesavadas et al. |
| 2010/0286554 A1 | 11/2010 | Davis et al. |
| 2010/0312095 A1 | 12/2010 | Jenkins et al. |
| 2010/0324008 A1 | 12/2010 | Low et al. |
| 2010/0331649 A1 | 12/2010 | Chou |
| 2011/0029325 A1 | 2/2011 | Georgiev et al. |
| 2011/0047702 A1 | 3/2011 | Diao |
| 2011/0078145 A1 | 3/2011 | Chung et al. |
| 2011/0087117 A1 | 4/2011 | Tremper et al. |
| 2011/0098531 A1 | 4/2011 | To |
| 2011/0106749 A1 | 5/2011 | Krishnan et al. |
| 2011/0118089 A1 | 5/2011 | Ellis |
| 2011/0118603 A1 | 5/2011 | Suh et al. |
| 2011/0121049 A1 | 5/2011 | Malinouskas et al. |
| 2011/0125522 A1 | 5/2011 | Kaplan et al. |
| 2011/0125527 A1 | 5/2011 | Nair |
| 2011/0153356 A1 | 6/2011 | Kenedy et al. |
| 2011/0177998 A1 | 7/2011 | Shemesh et al. |
| 2011/0179068 A1 | 7/2011 | O'Brien |
| 2011/0184245 A1 | 7/2011 | Xia et al. |
| 2011/0190588 A1 | 8/2011 | McKay |
| 2011/0190772 A1 | 8/2011 | Saadat et al. |
| 2011/0191356 A1 | 8/2011 | Gazula |
| 2011/0196377 A1 | 8/2011 | Hodorek et al. |
| 2011/0200177 A1 | 8/2011 | Patton et al. |
| 2011/0202486 A1 | 8/2011 | Fung et al. |
| 2011/0208113 A1 | 8/2011 | Toma et al. |
| 2011/0251694 A1 | 10/2011 | Wasielewski |
| 2011/0290250 A1 | 12/2011 | Olson et al. |
| 2011/0295621 A1 | 12/2011 | Farooq et al. |
| 2011/0295622 A1 | 12/2011 | Farooq et al. |
| 2012/0004894 A1 | 1/2012 | Butler et al. |
| 2012/0006335 A1 | 1/2012 | Lee et al. |
| 2012/0011253 A1 | 1/2012 | Friedman et al. |
| 2012/0016422 A1 | 1/2012 | Hua |
| 2012/0016432 A1 | 1/2012 | Westendorp et al. |
| 2012/0022885 A1 | 1/2012 | Murayama et al. |
| 2012/0035948 A1 | 2/2012 | Borton et al. |
| 2012/0041784 A1 | 2/2012 | Farooq et al. |
| 2012/0041788 A1 | 2/2012 | Wons et al. |
| 2012/0047105 A1 | 2/2012 | Saigal et al. |
| 2012/0054150 A1 | 3/2012 | McQueen et al. |
| 2012/0056993 A1 | 3/2012 | Luqman et al. |
| 2012/0065640 A1 | 3/2012 | Metzger et al. |
| 2012/0065987 A1 | 3/2012 | Farooq et al. |
| 2012/0078236 A1 | 3/2012 | Schoepp |
| 2012/0101842 A1 | 4/2012 | Montano |
| 2012/0109004 A1 | 5/2012 | Cadwell |
| 2012/0116310 A1 | 5/2012 | Forsell |
| 2012/0117088 A1 | 5/2012 | Kawakami et al. |

(56) References Cited

U.S. PATENT DOCUMENTS

| | | |
|---|---|---|
| 2012/0123485 A1 | 5/2012 | Dehnad et al. |
| 2012/0123716 A1 | 5/2012 | Clark |
| 2012/0141034 A1 | 6/2012 | Iannotti et al. |
| 2012/0150243 A9 | 6/2012 | Crawford et al. |
| 2012/0154582 A1* | 6/2012 | Johnson ............. G16H 40/20 340/521 |
| 2012/0157984 A1 | 6/2012 | Thapliyal et al. |
| 2012/0165652 A1* | 6/2012 | Dempsey ............. A61B 34/25 600/411 |
| 2012/0172854 A1 | 7/2012 | Raymond et al. |
| 2012/0194419 A1 | 8/2012 | Osterhout et al. |
| 2012/0203070 A1 | 8/2012 | Crenshaw et al. |
| 2012/0232668 A1 | 9/2012 | Iannotti |
| 2012/0232919 A1 | 9/2012 | Wilson et al. |
| 2012/0255122 A1 | 10/2012 | Diel et al. |
| 2012/0264997 A1 | 10/2012 | Isham |
| 2012/0269841 A1 | 10/2012 | Sidhu et al. |
| 2012/0321168 A1 | 12/2012 | Deitz |
| 2013/0038707 A1* | 2/2013 | Cunningham ....... A61B 1/0005 348/65 |
| 2013/0066647 A1 | 3/2013 | Andrie et al. |
| 2013/0073306 A1 | 3/2013 | Shlain et al. |
| 2013/0085314 A1 | 4/2013 | Vilsmeier |
| 2013/0085779 A1 | 4/2013 | Vilsmeier |
| 2013/0088414 A1 | 4/2013 | Artsyukhovich et al. |
| 2013/0123582 A1 | 5/2013 | Xia et al. |
| 2013/0191154 A1* | 7/2013 | William R ............. G06F 3/0482 705/3 |
| 2013/0197529 A1 | 8/2013 | Metzger et al. |
| 2013/0218060 A1 | 8/2013 | Bushby |
| 2013/0239331 A1 | 9/2013 | Eaton et al. |
| 2013/0261433 A1 | 10/2013 | Daon |
| 2013/0288215 A1 | 10/2013 | Butler et al. |
| 2013/0307955 A1 | 11/2013 | Deitz et al. |
| 2014/0002492 A1 | 1/2014 | Lamb et al. |
| 2014/0047570 A1 | 2/2014 | Altiok |
| 2014/0081659 A1 | 3/2014 | Nawana et al. |
| 2014/0088990 A1 | 3/2014 | Nawana et al. |
| 2014/0204190 A1* | 7/2014 | Rosenblatt, III ......... H04N 7/14 348/77 |
| 2015/0127316 A1 | 5/2015 | Avisar |
| 2015/0157468 A1 | 6/2015 | Wakayama et al. |
| 2015/0261922 A1 | 9/2015 | Nawana et al. |
| 2015/0282796 A1 | 10/2015 | Nawana et al. |
| 2016/0287236 A1 | 10/2016 | Garcia-Bengochea et al. |
| 2016/0338685 A1 | 11/2016 | Nawana et al. |
| 2017/0231715 A1 | 8/2017 | Roger et al. |
| 2018/0344308 A1 | 12/2018 | Nawana et al. |
| 2018/0344309 A1 | 12/2018 | Nawana et al. |
| 2019/0104919 A1* | 4/2019 | Shelton, IV ........ A61B 90/361 |
| 2019/0216452 A1 | 7/2019 | Nawana et al. |

FOREIGN PATENT DOCUMENTS

| | | |
|---|---|---|
| EP | 1 406 203 A2 | 4/2004 |
| EP | 1 734 878 A2 | 12/2006 |
| EP | 1 769 771 A1 | 4/2007 |
| EP | 1 937 178 B1 | 12/2011 |
| EP | 2 538 885 A1 | 1/2013 |
| EP | 2 542 176 A1 | 1/2013 |
| JP | 2006-149560 A | 6/2006 |
| JP | 2007287027 A | 11/2007 |
| JP | 2008173159 A | 7/2008 |
| JP | 2008532104 A | 8/2008 |
| JP | 2008541281 A | 11/2008 |
| JP | 2010172559 A | 8/2010 |
| WO | WO-00/72452 A2 | 11/2000 |
| WO | WO-2004/030528 A1 | 4/2004 |
| WO | WO-2005/034001 A1 | 4/2005 |
| WO | WO-2006/138067 A2 | 12/2006 |
| WO | WO-2007/017642 A1 | 2/2007 |
| WO | WO-2007/145937 A2 | 12/2007 |
| WO | WO-20081021494 A2 | 2/2008 |
| WO | WO-2008/144551 | 11/2008 |
| WO | WO-20091039391 A1 | 3/2009 |
| WO | WO-2009/061883 A1 | 5/2009 |
| WO | WO-2010/014864 A1 | 2/2010 |
| WO | WO-2010/051323 A1 | 5/2010 |
| WO | WO-20121068223 A1 | 5/2010 |
| WO | WO-2010/111419 A1 | 9/2010 |
| WO | WO-2010/124137 A1 | 10/2010 |
| WO | WO-2010/126797 A1 | 11/2010 |
| WO | WO-20101144425 A1 | 12/2010 |
| WO | WO-2011/0018748 A2 | 2/2011 |
| WO | WO-2011159778 A2 | 12/2011 |
| WO | WO-2012/020429 A1 | 2/2012 |
| WO | WO-2012/044697 A1 | 4/2012 |
| WO | WO-2012080906 A1 | 6/2012 |

OTHER PUBLICATIONS

Armstrong et al., An Integrative Review of Pressure Relief in Surgical Patients, AORN Journal 73.3: 645. Association of Operating Room Nurses, Inc. (Mar. 2001).

[No Author Listed] Electronic Charting and Process Control. Features. Massachusetts General Hospital . 1 page. 2008. http://www2.massgeneral.org/anesthesia/index.aspx?page=research_biomedical&subpage=echarting3.

[No Author Listed] Electronic Charting and Process Control. Science. Massachusetts General Hospital . 3 pages. 2008 http://www2.massgeneral.org/anesthesia/index.aspx?page=research_biomedical&subpage=echarting2.

[No Author Listed] Electronic Charting and Process Control. Summary. Massachusetts General Hospital . 1 page. 2008 http://www2.massgeneral.org/anesthesia/index.aspx?page=research_biomedical&subpage=echarting2.

[No Author Listed] Operating Room of the Future. Massachusetts General Hospital . 1 page. 2008 http://www2.massgeneral.org/anesthesia/index.aspx?page=research_biomedical&subpage=orofthefuture.

Amnon, Is mobile health about to enter a patent thicket? mobi health news. Oct. 23, 2012. 41 pages. http:// le-health-about-to-enter-a-patent-thicket/.

Guerlain et al., Assessing team performance in the operating room: development and use of a "black-box" recorder and other tools for the intraoperative environment. J Am; Coll Surg. Jan. 2005;200(1):29-37.

Levine et al., Development of a vendor agnostic, full disclosure system for capture, display, and storage of operative data. AMIA Annu Symp Proc. 2006:1006.

Levine et al., Usability factors in the organization and display of disparate information; sources in the operative environment. AMIA Annu Symp Proc. 2005:1025.

Meyer et al., A computerized perioperative data integration and display system. Int J CARS. 2007;2:191-202.

Meyer et al., Integration of hospital information systems, operative and peri-operative; information systems, and operative equipment into a single information display. AMIA Annu Symp Proc. 2005:1054.

Petrov M.S., Vesnin A. Ya, Koltsova M.P. (2012) NLS-diagnostics of ankle joint damages. 3D computer NLS-graphy.54-56. http://www.uk.metatron-nls.ru/download/stat_a15_eng.pdf.

Privitera et al., "Visual Mapping of Clinical Procedures Using Ethnographic Techniques in Medical Device Design" from, An Ethnography of Global Landscapes and Corridors. Ed. Loshini Naidoo. 2012. Chapter 12. p. 223-232.

Rothman et al., Using information technology to improve quality in the OR. Anesthesiol Clin. Mar. 2011;29(1):29-55.

Stahl et al., Introducing new technology into the operating room: measuring the impact on job performance and satisfaction. Surgery. May 2005;137(5):518-26.

U.S. Appl. No. 13/488,827, filed Jun. 5, 2012.

Wacker et al., An augmented reality system for MR image-guided needle biopsy:; initial results in a swine model. Radiology. Feb. 2006;238(2):497-504.

Wilcox, Ethnographic field research for medical-device design. Biomed Instrum Technol. Mar.-Apr. 2012;46(2):117-21.

(56) References Cited

OTHER PUBLICATIONS

Day et al., The impact of a guideline-driven computer charting system on the emergency care of patients with acute back pain. Proc Annu Symp Comput Appl Med Care. 1995:576-80.
European Search Report for Application No. EP 08165092.1, dated Dec. 29, 2013. (9 pages).
International Search Report and Written Opinion for Application No. PCT/US2013/060030 dated Dec. 11, 2013 Pages).
Extended European Search Report for Application No. EP 13836834.5, dated Jul. 7, 2016. (6 pages).
Japanese Office Action for Application No. 2015-532130 dated May 30, 2017.
Alain Mottham et al.: "Event-Driven Data Integration for Personal Health Monitoring," Journal of Emerging Technologies in Web Intelligence: JETWI, vol. 1, No. 2, Nov. 1, 2009, XP054419031, Oulu, Finland, ISSN: 1798-0461, DOI: 10.4304/jetwi.1.2.110-118.
European Examination Report for Application No. EP 13836834.5, dated Jul. 19, 2018. (6 pages).
Sielhorst, Advanced Medical Displays: A Literature Review of Augmented Reality, Journal of Display Technology, vol. 4, No. 4, Dec. 2008.
Miller, "Shortened OR time and decreased patient risk through use of a modular surgical instrument with artificial intelligence," 2009, Surg Endosc 23, 1099.
Miyawaki, "Development of automatic acquisition system of surgical-instrument information in endoscopic and laparoscopic surgery," 2009 4th IEEE Conference on Industrial Electronics and Applications, 2009, pp. 3058-3063.
Wikipedia, "Augmented reality," 2012, https://web.archive.org/web/20120815203956/https://en.wikipedia.org/wiki/Augmented_reality.
Birkfellner et al., "Development of the Varioscope AR. A See-through HMD for Computer-Aided Surgery," Augmented Reality (ISAR 2000), Proceedings, IEEE and ACM International Symposium on Munich Germany, Oct. 5-6, 2000, pp. 54-59.
Extended European Search Report for Application No. EP 20203254.6, dated May 20, 2021. (7 pages).
Lamata et al., "Augmented Reality for Minimally Invasive Surgery: Overview and Some Recent Advances," In "Augmented Reality," Jan. 1, 2010, InTech, pp. 74-98.
(2005) "The robot should be able to do everything a nurse can," Dr. Treat said, truthaboutnursing.com, 9 Pages.
Agovic et al. (2011) "Computer Vision Issues in the Design of a Scrub Nurse Robot", IEEE International Conference on Robotics and Automation, 2921-2926.
Jacob et al. (2012) "Gestonurse: a Robotic Surgical Nurse for Handling Surgical Instruments in the Operating Room", Journal of Robotic Surgery, 6(1):53-63.
Lewin et al. (2007) "Intraoperative MRI With a Rotating, Tiltable Surgical Table: A Time Use Study and Clinical Results in 122 Patients", AJR. American journal of roentgenology, 189(5):1096-103.
Rosen et al. (Oct. 2006) "Doc at a Distance", IEEE Spectrum, 43(10):34-39.
Youngblut et al. (1996) "Review of Virtual Environment Interface Technology", Institute for Defense Analyses, 270 Pages.

\* cited by examiner

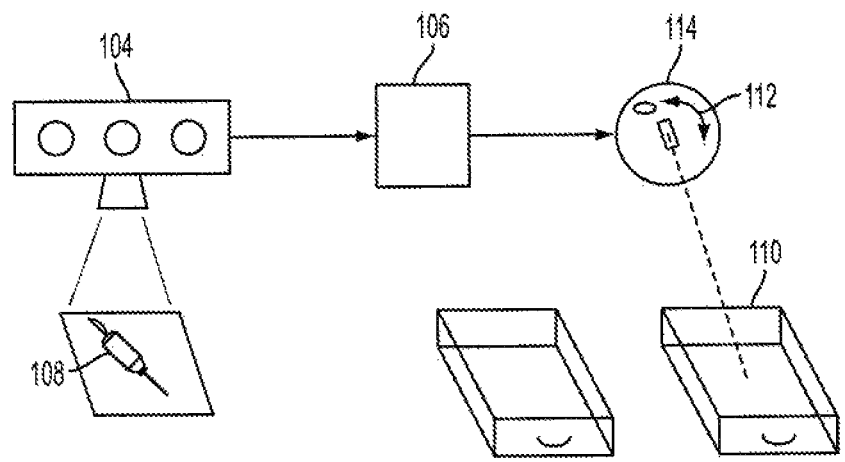
FIG. 26
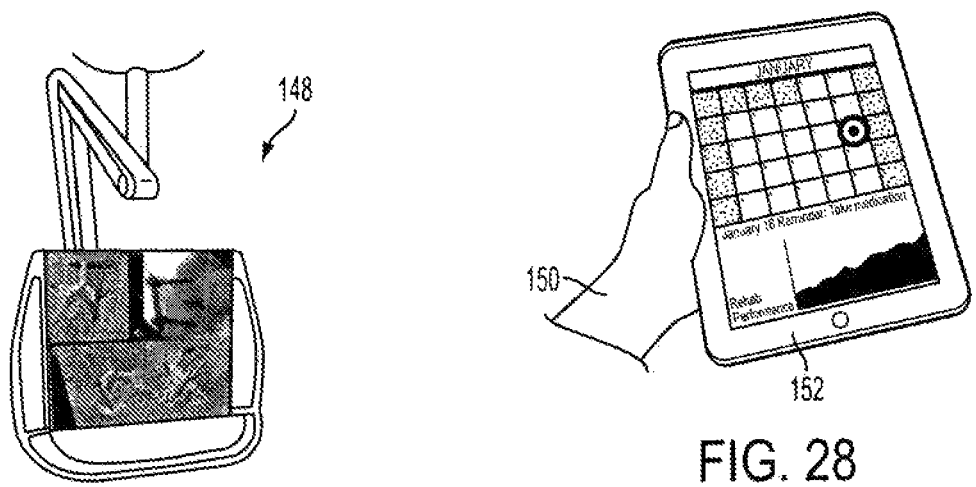
FIG. 27
FIG. 28

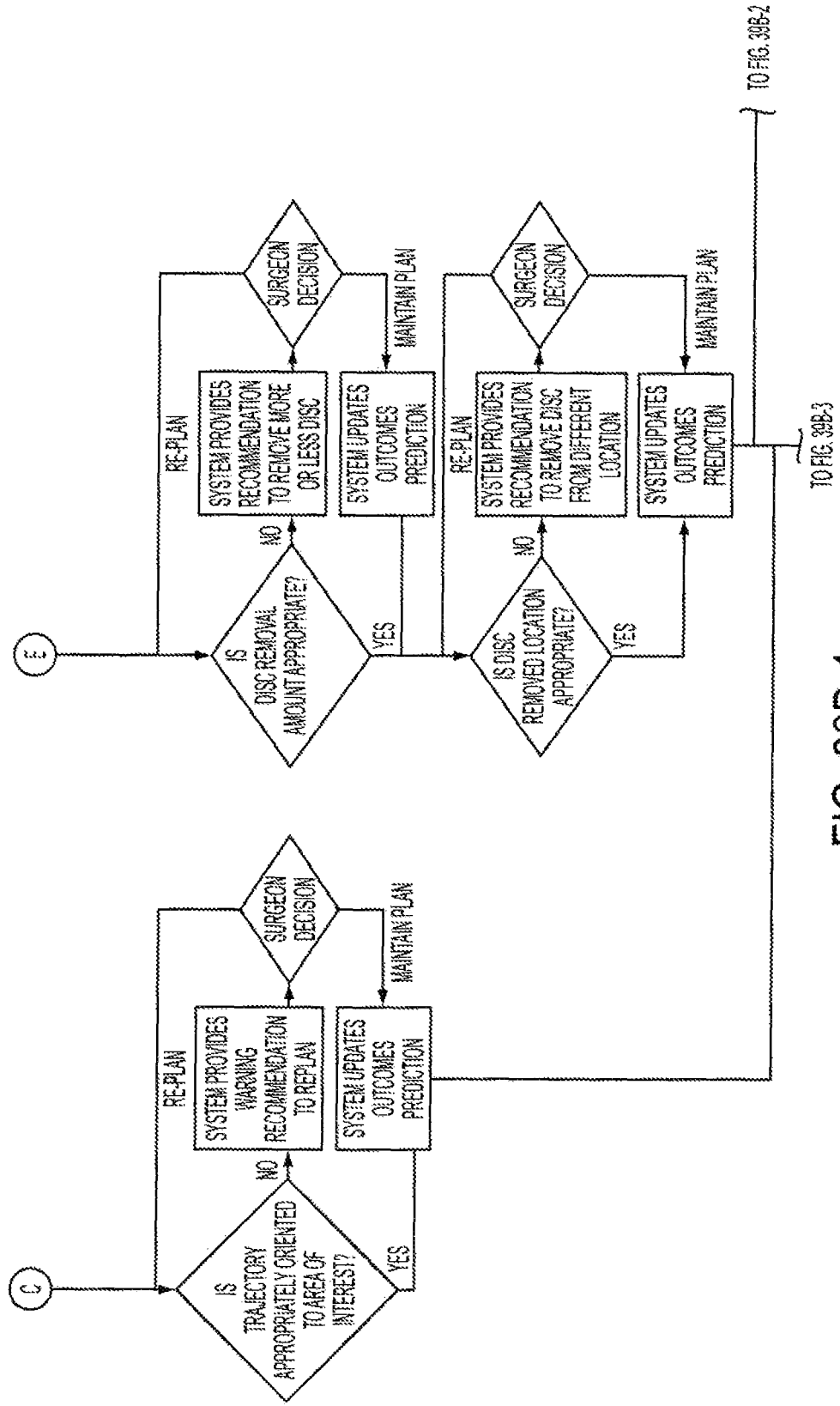

SYSTEMS AND METHODS FOR SURGICAL AND INTERVENTIONAL PLANNING, SUPPORT, POST-OPERATIVE FOLLOW-UP, AND FUNCTIONAL RECOVERY TRACKING

CROSS REFERENCE TO RELATED APPLICATIONS

The present application claims priority to U.S. patent application Ser. No. 14/734,359 entitled "Systems And Methods For Surgical And Interventional Planning, Support, Post-Operative Follow-Up, And, Functional Recovery Tracking" filed Jun. 9, 2015, which claims priority to U.S. patent application Ser. No. 14/031,761 (now U.S. Pat. No. 9,129,054) entitled "Systems And Methods For Surgical And Interventional Planning, Support, Post-Operative Follow-Up, And, Functional Recovery Tracking" filed Sep. 19, 2013, which claims priority to U.S. patent application Ser. No. 13/803,763 entitled "Systems And Methods For Surgical And Interventional Planning, Support, Post-Operative Follow-Up, And, Functional Recovery Tracking" filed Mar. 14, 2013, which claims priority to U.S. Provisional Patent Application No. 61/702,073 entitled "Systems And Methods For Surgical Planning, Support, And Review" filed Sep. 17, 2012 and to U.S. Provisional Patent Application No. 61/739,514 entitled "Systems And Methods For Surgical Planning, Support, And Review" filed Dec. 19, 2012, which are hereby incorporated by reference in their entireties.

FIELD

The present disclosure relates generally to systems and methods for surgical and interventional planning, support, post-operative follow-up, and functional recovery tracking. More particularly, the present disclosure relates to planning, supporting, and reviewing surgeries that involve medical devices, e.g., medical implants and instruments.

BACKGROUND

A traditional model for planning surgeries that involve medical devices includes several phases. These phases typically include wellness and prevention, diagnosis, and treatment.

The wellness and prevention phase typically involves a patient a monitoring their own health and having periodic check-up visits with a physician. The diagnosis phase typically involves the physician determining an ailment of the patient when the physician determines that the patient has a health problem. The physician can reach the diagnosis by consulting any one or more knowledge sources, such as their previous experience and knowledge, consultation with colleague(s), review of print and/or electronic literature, and review of diagnostic tests/procedures.

During the treatment phase, the physician typically determines a treatment plan for the patient to address the diagnosis, e.g., to relieve the patient of symptom(s). The treatment plan for many types of musculoskeletal and neurological diagnoses, for example, typically begins with a conservative, non-surgical treatment involving one or more therapies such as diet modification, exercise, medication, rest, limb elevation, limb mobilization, physical therapy, chiropractic care, etc. If the conservative, non-surgical treatment fails to adequately address the diagnosis, e.g., fails to adequately remedy the patient's symptom(s), or if the physician determines that the patient's condition is such that an approach more aggressive than a conservative, non-surgical treatment is needed to achieve desired results, the physician typically modifies the treatment plan to include a less conservative treatment. For diagnoses involving joint and/or bone ailments, e.g., spine ailments such as scoliosis, shoulder ailments such as injured rotator cuffs, knee ailments such as injured ACLs, etc., the less conservative treatment typically includes at least one invasive procedure such as injection therapy or a surgical procedure. Determining which surgical procedure to perform on the patient and determining which surgical techniques and medical devices to use in the selected surgical procedure typically involves a significant amount of time and planning by at least the performing surgeon.

Planning each surgical procedure also logistically typically involves coordination of numerous hospital resources. This planning also typically involves coordination with the patient for outpatient preparation and testing. A traditional model for supporting and managing surgeries that involve medical devices includes several phases. These phases typically include surgical planning, inventory planning, intra-operative support, post-surgery logistics, and charge capture or billing.

During the surgical planning phase, a surgeon or a staff member at the surgeon's office contacts the hospital where the surgery is to be performed to schedule resources such as operating rooms, equipment, and support staff. The hospital maintains a surgery schedule using a spreadsheet, whiteboard, or internal enterprise resource planning system that includes information such as the type of surgery, the name of the surgeon, the date the surgery is to be performed, and the supply and equipment needs of the surgery. A representative of a medical device company obtains the surgery schedule periodically and, for each surgery that involves a medical device provided by the medical device company, meets with the surgeon to discuss a plan for the surgery.

After establishing a plan for the surgery, the representative orders the various medical devices believed to be necessary for the surgery in the inventory planning phase. The medical devices are shipped from the medical device company or a distributor affiliated therewith to the representative, who is then responsible for providing the medical devices to the hospital for sterilization in advance of the surgery.

Prior to the surgery, the representative is typically relied upon to provide pre-surgery training on any new or modified medical devices or instruments. Such training can include use of hands-on demonstration equipment or review of surgical brochures provided by the medical device manufacturer. The representative is generally responsible for selecting and executing the appropriate training, based on the available supporting materials.

During the surgery itself, the representative is typically present in the operating room, regardless of the complexity of the surgery, to provide technical support to the surgeon and staff. The representative is also present to track consumption of inventory as well as components in need of maintenance or replacement.

After the surgery, the representative ensures that consumed inventory is replenished and that reusable instruments are sterilized and prepared for subsequent use.

Finally, the representative assists hospital staff in completing paperwork that identifies the patient and the inventory consumed. A purchasing group at the hospital reviews the paperwork and transmits it to the medical device company or its distributor. A manual reconciliation process occurs thereafter to determine billing amounts and to trigger inventory replenishment.

There are a number of inefficiencies associated with existing surgery planning, support, and management models. For example, by the time a patient consults a physician regarding self-detected symptom(s), the patient may have difficulty remembering the exact timing and/or intensity of symptom progression over a period of days, weeks, or months, which can adversely affect a physician's ability to accurately diagnosis a problem and/or determine the necessary aggressiveness of treatment.

For another example, during treatment, it can be difficult for a physician to monitor the patient's progress and compliance with the treatment, particularly during non-surgical treatment in which the patient is not under direct medical care, e.g., in a hospital, at physical therapy, etc, and more particularly when the patient is not under daily supervision of medical care. Additionally, the patient may provide inaccurate treatment progress information to the physician, such as by forgetting the exact timing of treatments performed at home or by being embarrassed to reveal failures in maintaining the suggested treatment and therefore not providing the physician with completely accurate information, and/or the patient may accidentally not perform a recommended treatment as instructed, such as by improperly performing an exercise, misunderstanding diet requirements, by forgetting to take medication at a recommended time, etc. The physician may therefore have difficulty determining whether and how to modify the patient's treatment plan, which can delay and/or hinder the patient's healing.

For example, during planning of a surgical procedure, a surgeon is typically more likely to perform a familiar, previously-performed procedures and use familiar, previously-used medical devices, e.g., to increase the surgeon's comfort and confidence in performing the surgery and to decrease the amount of time necessary to prepare for the surgery. However, the patient may thus not benefit from newer, improved surgical techniques and medical devices and/or from more effective treatments for specific symptoms.

For another example, a surgeon may plan a certain intervention but not fully execute the plan for any one or more reasons, e.g., wrong site surgery, unintended malposition of a device, and inadequate decompression of a nerve or alignment of anatomic elements.

For yet another example, a large portion of the representative's time is spent in the operating room during routine procedures in which the representative's assistance is rarely if ever necessary. The representative also spends a significant amount of time completing paperwork and performing surgical planning, inventory management, and other logistical tasks. This time could be better spent supporting more complex surgeries in which representative input is crucial, or generating new business for the medical device company. Furthermore, there are significant costs associated with employing a large staff of representatives.

These models also suffer from a number of inventory-related inefficiencies. For example, in the field of orthopedics, medical device kits are typically assembled so as to provide the necessary implants, tools, and instruments for any of a variety of types of surgery, ranging from the most routine to extraordinarily complex. As a result, many of the medical devices in the kit are not used during routine procedures, and are needlessly transported, inventoried, tracked, processed, sterilized, etc.

Accordingly, there remains a need for improved systems and methods for surgical and interventional planning, support, post-operative follow-up, and functional recovery tracking.

SUMMARY

The present invention generally provides systems and methods for surgical and interventional planning, support, post-operative follow-up, and functional recovery tracking.

In one aspect, a medical system is provided that in one embodiment includes a processor configured to receive treatment plan data regarding a plurality of patients. The treatment plan data includes a plan of medical treatment corresponding to each of the patients. Each of the plans have associated therewith at least one medical diagnosis in common with all of the plans. The processor is also configured to determine effectiveness of each of the plans and to determine a suggested plan of medical treatment for a patient based on the determined effectiveness. The patient has the at least one medical diagnosis. The processor is also configured to provide the suggested plan to a user.

The system can vary in any number of ways. For example, the processor can be configured to receive compliance data regarding compliance of the patients with their corresponding plans, and determining the effectiveness can include determining based on the compliance data an extent of each patient's compliance with their corresponding plans. Determining the suggested plan can include choosing at least a one of the plans having a highest level of compliance. For another example, the plans for a first subset of the patients can include a non-surgical treatment, the plans for a second subset of the patients can include a surgical treatment, and determining the suggested plan can include comparing outcomes of the non-surgical treatments with outcomes of the surgical treatments. Determining the suggested plan can include choosing at least a one of the plans having a best outcome among the surgical treatments and the non-surgical treatments. For still another example, determining the effectiveness can include determining an effect of each of the plans on the at least one medical diagnosis, and determining the suggested plan can include choosing at least a one of the plans having a most desired effect on the at least one medical diagnosis. For another example, the processor can be configured to receive performance data regarding performances of surgical procedures included in each of the plans that include performance of the surgical procedure as at least part of the medical treatment, and determining the effectiveness can include choosing at least a one of the plans based at least on the performance data. For another example, the system can include a display, and providing the suggested plan can include showing the suggested plan on the display.

In another embodiment, a medical system is provided in that includes a storage unit and a processor. The storage unit is configured to store a plurality of medical diagnoses and store a plurality of medical treatments. Each of the diagnoses has a plurality of patient-specific factors associated therewith. The patient-specific factors include at least symptoms. Each of the treatments having one or more of the medical diagnoses associated therewith. The storage unit also stores an effectiveness of each of the treatments as related to their associated one or more medical diagnoses. The processor is configured to receive symptom data indicating a plurality of symptoms experienced by a patient, determine which one or more of the stored medical diagnoses are associated with the received plurality of symptoms, provide the determined medical diagnoses to a user, determine which one or more of the treatments are associated with the determined medical diagnoses, and provide at least one of the determined treatments to the user. The at least one of the determined treatments has the highest effectiveness associated therewith.

The system can have any number of variations. For example, the stored effectiveness for each of the treatments can be based on any one or more of compliances of previous patients with a treatment plan associated with the treatment, an effect of the treatment on the one or more medical diagnoses associated therewith, an outcome a surgical procedure included as part of the treatment, and compliances of previous patients with a post-surgery treatment plan associated with the surgical procedure. For another example, the system can include a display. Providing the determined medical diagnoses can include showing the determined medical diagnoses on the display, and providing the at least one of the determined treatments can include showing the at least one of the determined treatments on the display.

In another embodiment, a medical system is provided that includes a processor configured to receive plan data regarding a virtual performance of a surgical procedure on a patient, and to receive performance data regarding an actual performance of the surgical procedure on the patient. The performance data is received in real time with the actual performance of the surgical procedure. The processor is also configured to determine if the plan data varies from the performance data. If the plan data is determined to vary from the performance data, the processor is configured to provide a warning to a user and to repeat the determining for subsequent performance data received in real time with the actual performance of the surgical procedure. The warning includes an indication of the determined variance. If the plan data is determined to not vary from the performance data, the processor is configured to repeat the determining for subsequent performance data received in real time with the actual performance of the surgical procedure.

The system can vary in any number of ways. For example, the processor can be configured to receive plan data regarding a plurality of virtual performances of the surgical procedure on a plurality of patients, and to receive performance data regarding a plurality actual performances of the surgical procedure on the plurality of patients. The performance data is received in real time with the actual performances of the surgical procedures. The processor can also be configured to determine if the plan data regarding the plurality of virtual performances varies from the performance data regarding the plurality actual performances, determine if any one or more of the determined variances are a same type of variance, and provide a recommendation to a user performing another virtual performance of the surgical procedure based on the one or more determined variances determined to be the same type of variance. For another example, the indication of the determined variance can include a recommended course of action to match the actual performance of the surgical procedure to the virtual performance of a surgical procedure. For yet another example, the processor can be configured to collate all of the determined variances of the plan data from the performance data and of the plan data for the subsequent performance data, and to provide the collated determined variances in a report. The report can be a paper report or an electronic report. For yet another example, a type of the received performance data can include at least one of data regarding movement of a surgical instrument being used in the actual performance of the surgical procedure, movement of staff present for the actual performance of the surgical procedure, patient vital signs, identification of a surgical instrument being used in the actual performance of the surgical procedure, identification of staff present in the actual performance of the surgical procedure, an amount of tissue retraction, a duration of tissue retraction, and one or more real time images of the patient acquired during the actual performance of the surgical procedure. A type of the received plan data can correspond to the type of the received performance data. For still another example, the determined variance can include at least one of a surgical instrument being moved relative to the patient than in the actual performance of the surgical procedure different than in the virtual performance of the surgical procedure, a surgical implant being used in the actual performance of the surgical procedure being implanted at a different location within the patient than the surgical implant used in the virtual performance of the surgical procedure, different radiation exposures in the actual performance of the surgical procedure and the virtual performance of the surgical procedure, different lengths of tissue retraction time in the actual performance of the surgical procedure and the virtual performance of the surgical procedure, different pharmaceutical administration to the patient in the actual performance of the surgical procedure than in the virtual performance of the surgical procedure, a different number of staff being present in the actual performance of the surgical procedure than a number of virtual staff present in the virtual performance of the surgical procedure, a different duration of a step in the actual performance of the surgical procedure than in the virtual performance of the surgical procedure, a different surgical instrument being used in a step of the actual performance of the surgical procedure than in the virtual performance of the surgical procedure, and a step performed in the virtual performance of the surgical procedure not having been performed in the actual performance of the surgical procedure. For another example, the warning can include at least one of an audible sound, an illuminated light, a flashing light, a vibration of a surgical instrument being used in the actual performance of the surgical procedure, and a text warning on a display.

In another embodiment, a medical system is provided that includes a processor configured to receive post-surgery treatment plan data regarding a plurality of patients. The post-surgery treatment plan data includes a plan of medical treatment corresponding to each of the patients. Each of the plans has associated therewith at least one surgical procedure in common with all of the plans. The processor is also configured to determine an effectiveness of each of the plans, and to determine a suggested plan of medical treatment for a patient based on the determined effectiveness. The patient has had the at least one surgical procedure performed thereon. The processor is also configured to provide the suggested plan to a user.

The system can have any number of variations. For example, the processor can be configured to receive compliance data regarding compliance of the patients with their corresponding plans, and determining the effectiveness can include determining based on the compliance data an extent of each patient's compliance with their corresponding plans. Determining the suggested plan can include choosing at least a one of the plans having a highest level of compliance. For another example, determining the effectiveness can include determining an effect of each of the plans on at least one medical diagnosis, and determining the suggested plan can include choosing at least a one of the plans having a most desired effect on the at least one medical diagnosis. The patient has been diagnosed with the at least one medical diagnosis. For yet another example, the system can include a display, and providing the suggested plan can include showing the suggested plan on the display.

In another embodiment, a medical system is provided that includes a diagnosis and treatment module, a pre-op module, an operation module, a post-op module, and a recovery module. The diagnosis and treatment module receives information regarding a plurality of symptoms of a patient from the patient, receives augmented information regarding the plurality of symptoms of the patient from a medical professional, provides a recommended non-surgical treatment for the patient based on at least the information regarding the plurality of symptoms and the augmented information, allows selection of a non-surgical treatment for the patient from a plurality of available non-surgical treatments including at least the recommended non-surgical treatment, receives information regarding compliance of the patient with the selected non-surgical treatment, provides a recommended invasive treatment for the patient based on at least one of the information regarding compliance, the information regarding the plurality of symptoms, and the augmented information, and allows selection of an invasive treatment for the patient from a plurality of available invasive treatments including at least the recommended invasive treatment. The pre-op module allows a three-dimensional electronic simulation of the selected invasive treatment to be performed on a virtual patient using a plurality of virtual instruments. The virtual patient is a model of the patient based on gathered medical data regarding the patient, and each of the plurality of virtual instruments are modeled on an actual instrument available for use in the selected invasive treatment. The pre-op module also stores the electronic simulation in a storage unit. The operation module compares an actual performance of the selected invasive treatment on the patient with the stored electronic simulation, provides electronic feedback regarding the comparison during the actual performance of the selected invasive treatment that indicates progress of the actual performance of the selected invasive treatment versus the stored electronic simulation, triggers an alarm if the comparison indicates that a step of the actual performance of the selected invasive treatment differs from the stored electronic simulation beyond a predetermined threshold amount of tolerable variance, and stores data regarding the actual performance of the selected invasive treatment in the storage unit. The post-op module compares the stored electronic simulation with the stored data regarding the actual performance of the selected invasive treatment, and, based on the comparison of the stored electronic simulation with the stored data regarding the actual performance of the selected invasive treatment, determines a variance between the stored electronic simulation and the stored data regarding the actual performance of the selected invasive treatment in the storage unit. The recovery module provides a recommended post-op treatment plan for the patient based on at least the stored data regarding the actual performance of the selected invasive treatment, allows selection of a post-op treatment for the patient from a plurality of available post-op treatments including at least the recommended post-op treatment, receives information regarding compliance of the patient with the selected post-op treatment plan, and provides a recommended follow-up treatment for the patient based at least on the information regarding compliance of the patient with the recommended post-op treatment plan.

The system can vary in any number of ways. For example, the system can include a processor configured to execute the functions performed by the diagnosis and treatment module, the pre-op module, the operation module, the post-op module, and the recovery module. The system can also include a storage unit storing the diagnosis and treatment module, the pre-op module, the operation module, the post-op module, and the recovery module. The processor and the storage unit can be included in a singular unit. The system can be provided with only a subset of the diagnosis and treatment module, the pre-op module, the operation module, the post-op module, and the recovery module. Each of the diagnosis and treatment module, the pre-op module, the operation module, the post-op module, and the recovery module can be modular components such that any one or more of the diagnosis and treatment module, the pre-op module, the operation module, the post-op module, and the recovery module can be selectively added to the system and removed from the system.

The diagnosis and treatment module can vary in any number of ways. For example, the diagnosis and treatment module can receive information regarding at least one of a plurality of patient-specific factors regarding the patient. The patient-specific factors can include any one or more of physical examination data, images of the patient, laboratory test results for the patient, demographic data for the patient, and/or on historical tests for the patient. Receiving the information regarding the at least one of the plurality of patient-specific factors can include receiving data from a plurality of sensors, e.g., a smartphone camera. The recovery module can receive information from the plurality of sensors after the actual performance of the selected invasive treatment. The recommended follow-up treatment can be based at least in part on the information from the plurality of sensors. The information regarding the at least one of the plurality of patient-specific factors can include receiving data regarding a scoliotic curve of the patient. The diagnosis and treatment module can provide modeling of potential curve progression to the patient based at least in part on the data regarding the scoliotic curve. The recovery module can provide modeling of potential curve progression to the patient based at least in part on the data regarding the scoliotic curve and on the stored data regarding the actual performance of the selected invasive treatment. The information regarding the at least one of the plurality of patient-specific factors can include receiving data regarding any one or more of mobility, gait, walking speed, flexibility, muscular strength, posture, range of motion, pain, neurologic tracking, joint movement tracking, bone density, and musculo-skeletal pain levels. For bone density, the diagnosis and treatment module can be configured to gather the bone density information using an image of the patient including an image of a bone density marker including a first material having a first density and a second material having a second density.

For another example, the diagnosis and treatment module receiving the information regarding the plurality of symptoms can include receiving data from a plurality of sensors, e.g., a smartphone camera. The recovery module can receive information from the plurality of sensors after the actual performance of the selected invasive treatment. The recommended follow-up treatment can be based at least in part on the information from the plurality of sensors. For yet another example, the diagnosis and treatment module receiving the information regarding the plurality of symptoms can include receiving data from a neural mapping device. The diagnosis and treatment module can measure a pain level of the patient by comparing the patient's neural map and associated self-described pain scores to a plurality of neural maps regarding a plurality of other patients and to a plurality of self-described pain scores of the plurality of other patients, thereby allowing the diagnosis and treatment module to normalize the self-described pain levels of the patient and the plurality of other patients. For another example, the diagnosis and treatment module can provide a historical success rate for each of the plurality of available surgical treatments. For yet another example, the diagnosis and treatment module can provide access to one or more knowledge sources regarding the recommended invasive treatment. The knowledge resources can include any one or more of print literature, electronic literature, training, and experts. For still another example, the diagnosis and treatment module can provide a suggested diagnosis for the patient based on at least the information regarding the plurality of symptoms and the augmented information. The diagnosis and treatment module can provide the suggested diagnosis comprises providing a plurality of suggested diagnoses. Each of the plurality of suggested diagnoses can be provided with a level of confidence based at least on historical accuracy of the diagnosis for patients having similar symptoms to the plurality of symptoms. The levels of confidence can be based at least on a comparison of a plurality of attributes associated with the patient and a plurality of attributes associated with the diagnosis. For another example, the diagnosis and treatment module providing the recommended non-surgical treatment can include providing a plurality of recommended non-surgical treatments. Each of the plurality of recommended non-surgical treatments can be provided with a level of confidence of success based at least on historical outcomes of the non-surgical treatment. The levels of confidence can be based at least on a comparison of a plurality of attributes associated with the patient and a plurality of attributes associated with the non-surgical treatment. For yet another example, the diagnosis and treatment module providing the recommended invasive treatment can include providing a plurality of recommended invasive treatments. Each of the plurality of recommended invasive treatments can be provided with a level of confidence of success based at least on historical outcomes of the invasive treatment. The levels of confidence can be based at least on a comparison of a plurality of attributes associated with the patient and a plurality of attributes associated with the invasive treatment.

The pre-op module can vary in any number of ways. For example, the pre-op module can monitor the patient in a hospital prior to performance of the actual performance of the selected invasive treatment at the hospital. The monitoring can include at least one of vital signs of the patient, pre-op preparations performed on the patient, and a location of the patient in the hospital. Based on the monitoring, the pre-op module can trigger at least one of an operating room preparation for the actual performance of the selected invasive treatment and a recovery room preparation for the actual performance of the selected invasive treatment.

The operation module can have any number of variations. For example, the operation module can track a number of instruments used in the actual performance of the selected invasive procedure. For another example, the operation module can track a number of times each of the instruments used in the actual performance of the selected invasive procedure have been used in a plurality of invasive procedures. The post-op module can trigger an alarm when the number of times for any one or more of the instruments exceeds a predetermined threshold number, the predetermined threshold number reflecting at least one of a maximum number of times an instrument can be used in invasive procedures before needing sharpening, a maximum number of times an instrument can be used in invasive procedures before needing lubrication, a maximum number of times an instrument can be used in invasive procedures before needing replacement, and a maximum number of times an instrument can be used in invasive procedures before needing calibration. For yet another example, the operation module can determine when any one or more of a non-sterile person and a non-sterile instrument enters an area in which the actual performance of the selected invasive treatment is being performed, and in response to the determination, trigger an alarm indicating breach of sterility in the area. For another example, the operation module can identify an instrument to be used in the actual performance of the selected invasive procedure and provide an indication of a position of the instrument in an instrument tray to be provided in an area in which the actual performance of the selected invasive procedure will be performed. The indication can include at least one of an audio signal and a visual signal. For another example, the operation module can gather data for a medical practitioner involved in the actual performance of the selected invasive procedure in a period of time following the invasive procedure. The data can include an energy level of the medical practitioner and nutrition of the medical practitioner. The post-op module can compare the gathered data for the medical practitioner with the stored data regarding the actual performance of the selected invasive treatment so as to determine recommended improvements in the energy level and the nutrition. For yet another example, the operation module can provide the electronic feedback on a display, and the operation module can provide additional electronic information regarding the actual performance of the selected invasive treatment on the display including any one or more of a fluoroscopic image of the patient, vital signs of the patient, neural monitoring outputs, surgical techniques videos, camera feeds from outside a room where the selected invasive treatment is being performed, power usage of instruments, and controls for any one or more devices that gather the additional electronic information and provide the additional electronic information to the operation module. For still another example, the operation module can provide feedback regarding a position of the patient in a room where the selected invasive treatment is to be performed. The feedback can provide guidance on movement of the patient such that the position of the patient matches a predetermined optimal position of the patient for performance of the selected invasive treatment. The feedback can be based at least one any one or more of images of the patient in the room and images of the patient acquired prior to the patient being located in the room. For another example, the operation module can allow for user selection of anatomy of the patient to be shown on a display in any one or more of a plurality of visualization options, e.g., 3D images, holograms, and projections. For yet another example, the operation module can show the electronic feedback on a display and allows user selection of different information to be shown on the display using a no-touch control operable by a user. The no-touch control can include at least one of a data board, a gesture-based control, and direct brain control. For still another example, the comparing of the operation module can include comparing an amount of spinal disc clearing of the stored electronic simulation with an actual amount of spinal disc clearing. For another example, the operation module can determine an instrument needed for an upcoming aspect of the actual performance of the selected invasive treatment and automatically trigger sterilization and retrieval of the determined instrument. For yet another example, the operation module can determine at least one of a time length of retraction of a tissue during the actual performance of the selected invasive treatment, an amount of the tissue retraction, and an amount of pressure being placed on at least one of tissue and nerves as a result of the retraction, and the operation module can trigger an alarm if any one or more of the time length reaches a predetermined threshold amount of time, the amount of tissue retraction reaches a predetermined amount of tissue, and the amount of pressure reaches a predetermined amount of pressure. For another example, the comparing of the operation module can include comparing a trajectory of an instrument in the stored electronic simulation with an actual trajectory of the instrument in the actual performance of the selected invasive treatment, and if the actual trajectory differs from the trajectory, the operation module can provide a warning indicating that the trajectories differ. For yet another example, the operation module can provide information regarding nerves of the patient during in the actual performance of the selected invasive treatment. The nerve information can include at least one of a visual overlay of nerves on the patient and an augmented reality view of the nerves.

The post-op module can have any number of variations. For example, the post-op module can gather data for each medical practitioner involved in the actual performance of the selected invasive procedure in a period of time following the invasive procedure. The invasive procedure can be performed in an operating room, and the data can include an energy level of the medical practitioner and nutrition of the medical practitioner. The post-op module can compare the gathered data with data stored in the storage unit regarding actual performance of invasive treatments in the operating room so as to determine recommended improvements in the energy level and the nutrition.

In another aspect, a medical method is provided that in one embodiment includes the functions performed by the diagnosis and treatment module, the pre-op module, the operation module, the post-op module, and the recovery module.

In another embodiment, a medical method is provided that includes receiving treatment plan data regarding a plurality of patients. The treatment plan data includes a plan of medical treatment corresponding to each of the patients. Each of the plans has associated therewith at least one medical diagnosis in common with all of the plans. The method also includes determining an effectiveness of each of the plans, and determining a suggested plan of medical treatment for a patient based on the determined effectiveness. The patient has the at least one medical diagnosis. The method also includes providing the suggested plan to a user.

The method can vary in any number of ways. For example, the method can include receiving compliance data regarding compliance of the patients with their corresponding plans, and determining the effectiveness can include determining based on the compliance data an extent of each patient's compliance with their corresponding plans. Determining the suggested plan can include choosing at least a one of the plans having a highest level of compliance. For another example, the plans for a first subset of the patients can include a non-surgical treatment, the plans for a second subset of the patients can include a surgical treatment, and determining the suggested plan can include comparing outcomes of the non-surgical treatments with outcomes of the surgical treatments. Determining the suggested plan can include choosing at least a one of the plans having a best outcome among the surgical treatments and the non-surgical treatments. For yet another example, determining the effectiveness can include determining an effect of each of the plans on the at least one medical diagnosis, and determining the suggested plan can include choosing at least a one of the plans having a most desired effect on the at least one medical diagnosis. For another example, the method can include receiving performance data regarding performances of surgical procedures included in each of the plans that include performance of the surgical procedure as at least part of the medical treatment, and determining the effectiveness can include choosing at least a one of the plans based at least on the performance data. For yet another example, providing the suggested plan can include showing the suggested plan on a display.

In another embodiment, a medical method is provided that includes storing a plurality of medical diagnoses and storing a plurality of medical treatments. Each of the diagnoses has a plurality of patient-specific factors associated therewith. The patient-specific factors include at least symptoms. Each of the treatments has one or more of the medical diagnoses associated therewith. The method also includes storing an effectiveness of each of the treatments as related to their associated one or more medical diagnoses, receiving symptom data indicating a plurality of symptoms experienced by a patient, determining which one or more of the stored medical diagnoses are associated with the received plurality of symptoms, providing the determined medical diagnoses to a user, determining which one or more of the treatments are associated with the determined medical diagnoses, and providing at least one of the determined treatments to the user. The at least one of the determined treatments has the highest effectiveness associated therewith.

The method can have any number of variations. For example, the stored effectiveness for each of the treatments can be based on any one or more of compliances of previous patients with a treatment plan associated with the treatment, an effect of the treatment on the one or more medical diagnoses associated therewith, an outcome a surgical procedure included as part of the treatment, and compliances of previous patients with a post-surgery treatment plan associated with the surgical procedure. For another example, providing the determined medical diagnoses can include showing the determined medical diagnoses on a display, and providing the at least one of the determined treatments can include showing the at least one of the determined treatments on the display.

In another embodiment, a medical method is provided that includes receiving plan data regarding a virtual performance of a surgical procedure on a patient, and receiving performance data regarding an actual performance of the surgical procedure on the patient. The performance data is received in real time with the actual performance of the surgical procedure. The method also includes determining if the plan data varies from the performance data. If the plan data is determined to vary from the performance data, a warning is provided to a user, and the determining is repeated for subsequent performance data received in real time with the actual performance of the surgical procedure. The warning includes an indication of the determined variance. If the plan data is determined to not vary from the performance data, the determining is repeated for subsequent performance data received in real time with the actual performance of the surgical procedure.

The method can have any number of variations. For example, the method can include receiving plan data regarding a plurality of virtual performances of the surgical procedure on a plurality of patients, and receiving performance data regarding a plurality actual performances of the surgical procedure on the plurality of patients. The performance data is received in real time with the actual performances of the surgical procedures. The method also includes determining if the plan data regarding the plurality of virtual performances varies from the performance data regarding the plurality actual performances, determining if any one or more of the determined variances are a same type of variance, and providing a recommendation to a user performing another virtual performance of the surgical procedure based on the one or more determined variances determined to be the same type of variance. For another example, the indication of the determined variance can include a recommended course of action to match the actual performance of the surgical procedure to the virtual performance of a surgical procedure. For yet another example, the method can include collating all of the determined variances of the plan data from the performance data and of the plan data for the subsequent performance data, and providing the collated determined variances in a report. The report can be a paper report or an electronic report. For yet another example, a type of the received performance data can include at least one of data regarding movement of a surgical instrument being used in the actual performance of the surgical procedure, movement of staff present for the actual performance of the surgical procedure, patient vital signs, identification of a surgical instrument being used in the actual performance of the surgical procedure, identification of staff present in the actual performance of the surgical procedure, an amount of tissue retraction, a duration of tissue retraction, and one or more real time images of the patient acquired during the actual performance of the surgical procedure. A type of the received plan data can correspond to the type of the received performance data. For still another example, the determined variance can include at least one of a surgical instrument being moved relative to the patient than in the actual performance of the surgical procedure different than in the virtual performance of the surgical procedure, a surgical implant being used in the actual performance of the surgical procedure being implanted at a different location within the patient than the surgical implant used in the virtual performance of the surgical procedure, different radiation exposures in the actual performance of the surgical procedure and the virtual performance of the surgical procedure, different lengths of tissue retraction time in the actual performance of the surgical procedure and the virtual performance of the surgical procedure, different pharmaceutical administration to the patient in the actual performance of the surgical procedure than in the virtual performance of the surgical procedure, a different number of staff being present in the actual performance of the surgical procedure than a number of virtual staff present in the virtual performance of the surgical procedure, a different duration of a step in the actual performance of the surgical procedure than in the virtual performance of the surgical procedure, a different surgical instrument being used in a step of the actual performance of the surgical procedure than in the virtual performance of the surgical procedure, and a step performed in the virtual performance of the surgical procedure not having been performed in the actual performance of the surgical procedure. For another example, the warning can include at least one of an audible sound, an illuminated light, a flashing light, a vibration of a surgical instrument being used in the actual performance of the surgical procedure, and a text warning on a display.

In another embodiment, a medical method is provided that includes receiving post-surgery treatment plan data regarding a plurality of patients. The post-surgery treatment plan data includes a plan of medical treatment corresponding to each of the patients. Each of the plans has associated therewith at least one surgical procedure in common with all of the plans. The method also includes determining an effectiveness of each of the plans, and determining a suggested plan of medical treatment for a patient based on the determined effectiveness. The patient has had the at least one surgical procedure performed thereon. The method also includes providing the suggested plan to a user.

The method can vary in any number of ways. For example, the method can include receiving compliance data regarding compliance of the patients with their corresponding plans, and determining the effectiveness can include determining based on the compliance data an extent of each patient's compliance with their corresponding plans. Determining the suggested plan can include choosing at least a one of the plans having a highest level of compliance. For another example, determining the effectiveness can include determining an effect of each of the plans on at least one medical diagnosis, and determining the suggested plan can include choosing at least a one of the plans having a most desired effect on the at least one medical diagnosis. The patient has been diagnosed with the at least one medical diagnosis. For yet another example, providing the suggested plan can include showing the suggested plan on a display.

In another aspect, a computer-readable medium is provided and has stored thereon a program that when executed can cause a computer to perform any of the methods.

BRIEF DESCRIPTION OF DRAWINGS

This invention will be more fully understood from the following detailed description taken in conjunction with the accompanying drawings, in which:

FIG. 26 is a perspective view of an embodiment of an instrument sorting system that communicates with the diagnosis, surgical planning, support, and management system of FIG. 2;

FIG. 27 is a perspective view of an embodiment of a client terminal showing post-op surgical procedure data received from the diagnosis, surgical planning, support, and management system of FIG. 2;

FIG. 28 is a perspective view of an embodiment of a client terminal showing post-op treatment plan data received from the diagnosis, surgical planning, support, and management system of FIG. 2;

FIG. 38-1 shows a portion of a flowchart of an exemplary embodiment of using a pre-op module of the diagnosis, surgical planning, support, and management system of FIG. 2;

FIG. 38-2 shows another portion of the flowchart of FIG. 38-1;

FIG. 39A-1 shows a portion of a flowchart of another exemplary embodiment of using a pre-op module of the diagnosis, surgical planning, support, and management system of FIG. 2;

FIG. 39A-2 shows another portion of the flowchart of FIG. 39A-1;

FIG. 39B-1 shows another portion of the flowchart of FIG. 39A-1;

FIG. 39B-2 shows another portion of the flowchart of FIG. 39A-1;

FIG. 39B-3 shows another portion of the flowchart of FIG. 39A-1;

FIG. 41B-1 shows another portion of the flowchart of FIG. 41A;

FIG. 41B-2 shows another portion of the flowchart of FIG. 41A;

DETAILED DESCRIPTION

Figure 1:
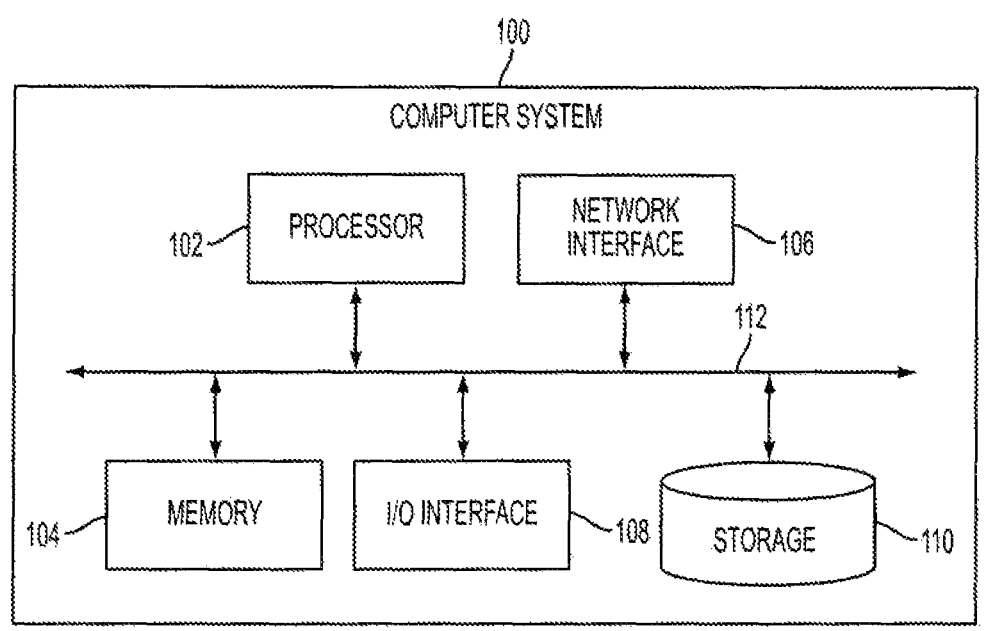
FIG. 1 is a schematic diagram of an embodiment of a computer system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Various systems and methods are provided for systems and methods for surgical and interventional planning, support, post-operative follow-up, and functional recovery tracking. In general, a patient can be tracked throughout medical treatment including through initial onset of symptoms, examination and diagnosis, non-surgical treatment, surgical treatment, and recovery from the surgical treatment. In one embodiment, a patient and one or more medical professionals involved with treating the patient can electronically access a comprehensive treatment planning, support, and review system, e.g., using one or more web pages. The system can provide recommendations regarding diagnosis, non-surgical treatment, surgical treatment, and recovery from the surgical treatment based on data gathered from the patient and the medical professional(s), thereby helping to improve accuracy in diagnosis and effectiveness of treatment. The system can manage the tracking of multiple patients, thereby allowing for data comparison between similar aspects of medical treatments, e.g., between similar non-surgical treatments, and for learning over time through continual data gathering, analysis, and assimilation to decision-making algorithms. The system can therefore help improve accuracy of diagnosis and effectiveness of treatment for multiple patients by considering previously gathered data, including, e.g., historic success rates as measured in Health-Related Quality of Life (HRQOL), utilization, and health/economic parameters, regarding similar diagnoses and treatments in providing suggested diagnoses and recommended treatments. The model can also facilitate various tasks associated with surgical planning, inventory planning, intra-operative support, post-surgery logistics, and billing phases of patient treatment. The system can allow for documentation and tracking of the progression of the patient throughout at least some phases of the patient's treatment, and in an exemplary embodiment all phases, which can be highly beneficial to non-surgical and surgical treatment of the patient as well as for informing decisions regarding non-surgical and surgical treatments of other patients.

Computer System

The systems and methods disclosed herein can be implemented using one or more computer systems, which are also referred to herein as digital data processing systems.

FIG. 1 illustrates one exemplary embodiment of a computer system 100. As shown, the computer system 100 can include one or more processors 102 which can control the operation of the computer system 100. The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 1 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing Hypertext Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The systems and methods disclosed herein can thus be provided as a singular unit configured to provide the various modules, display the various user interfaces, and capture the data described herein. The singular unit can be modular such that various aspects thereof can be swapped in and out as needed for, e.g., upgrade, replacement, maintenance, etc., without interrupting functionality of any other aspects of the system. The singular unit can thus also be scalable with the ability to be added to as additional modules and/or additional functionality of existing modules are desired and/or improved upon.

While some embodiments are described herein in the context of web pages, it will be appreciated that in other embodiments, one or more of the described functions can be performed without the use of web pages and/or by other than web browser software. A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Diagnosis, Surgical Planning, Support, and Management System Generally

Figure 2:
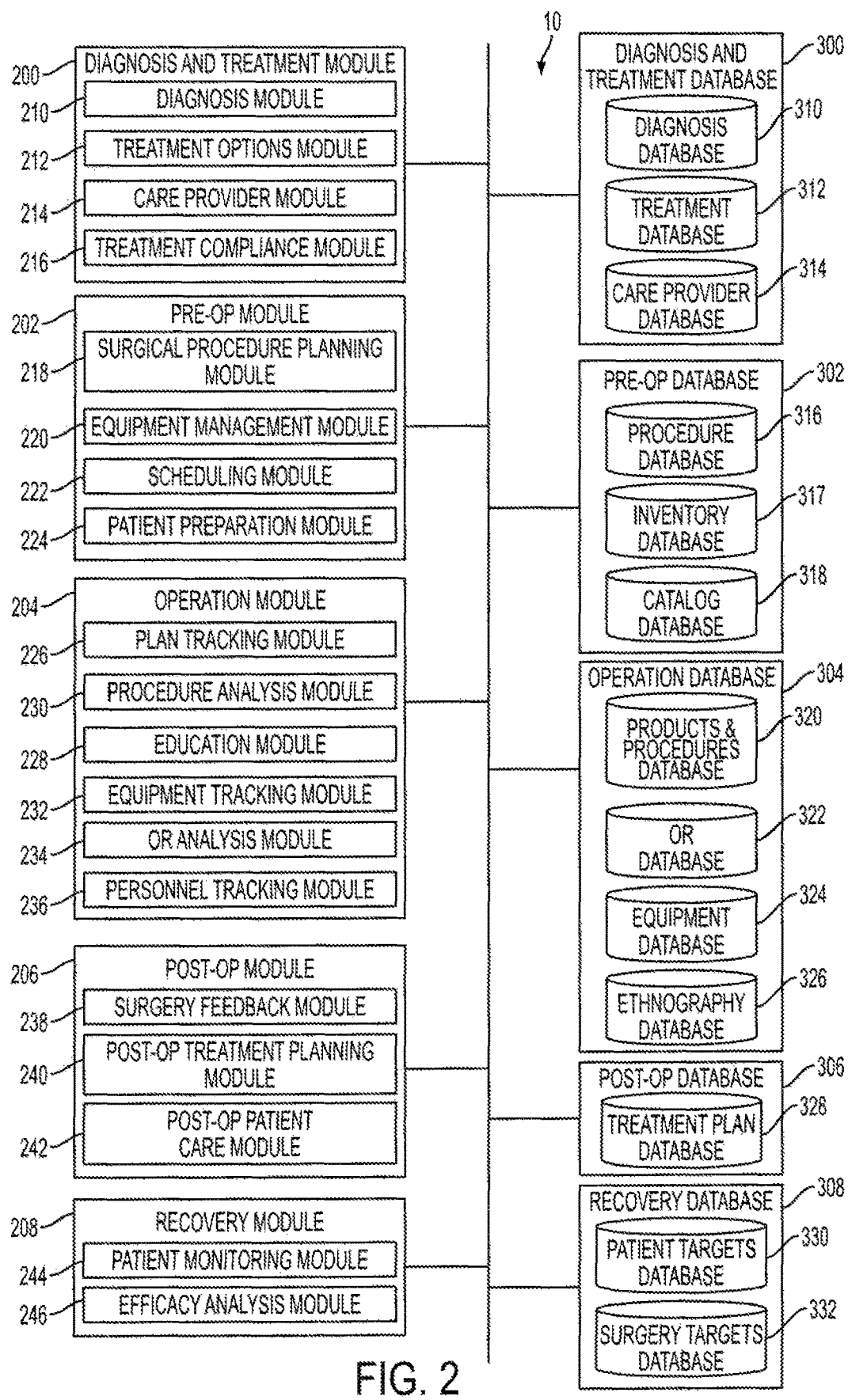
FIG. 2 is a schematic diagram of an embodiment a diagnosis, surgical planning, support, and management system.

FIG. 2 is a schematic block diagram of one exemplary embodiment of a diagnosis, surgical planning, support, and management system 10. The system 10 can includes a plurality of modules, discussed further below, which can each be implemented using one or more digital data processing systems of the type described above, and in particular using one or more web pages which can be viewed, manipulated, and/or interacted with using such digital data processing systems. The system 10 can thus be implemented on a single computer system, or can be distributed across a plurality of computer systems. The system 10 also includes a plurality of databases, which can be stored on and accessed by computer systems. It will be appreciated that any of the modules or databases disclosed herein can be subdivided or can be combined with other modules or databases.

Figure 3:
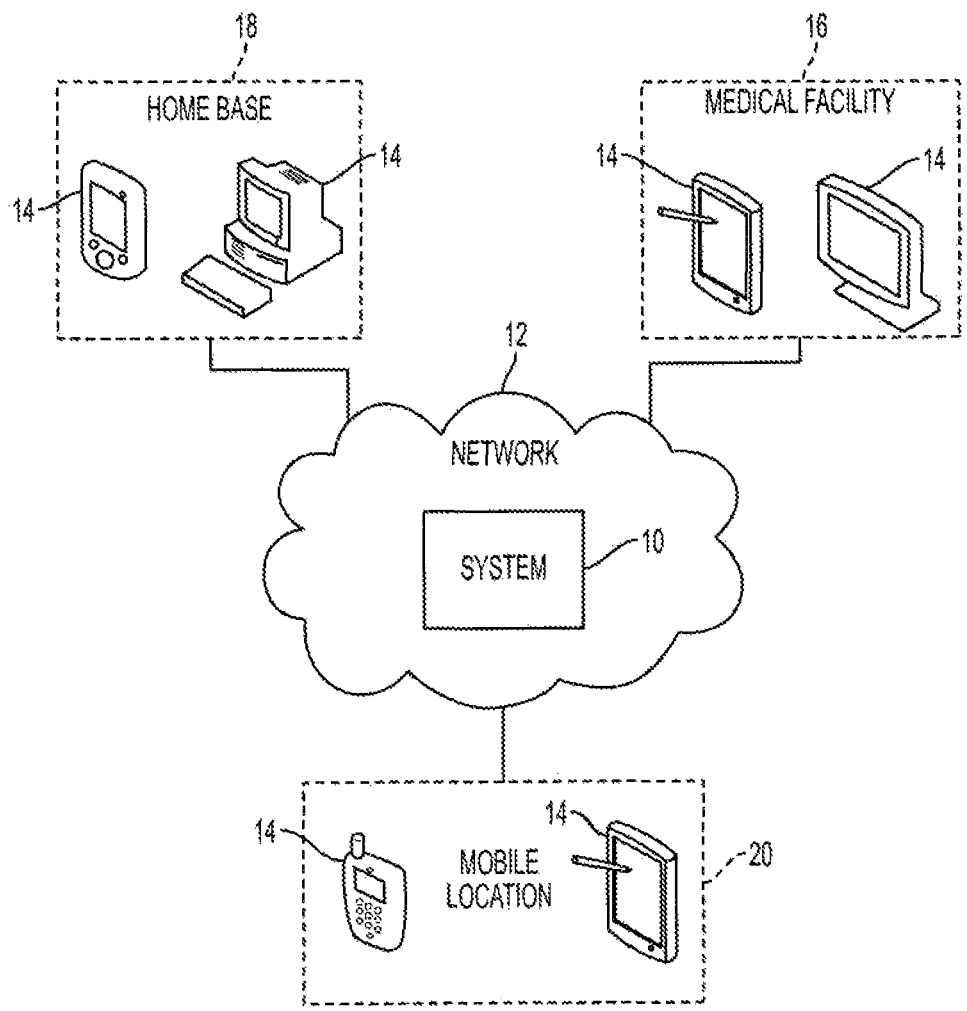
FIG. 3 is a schematic diagram of an embodiment of a network system including the diagnosis, surgical planning, support, and management system of FIG. 2.

Any of a variety of parties can access, interact with, control, etc. the system 10 from any of a variety of locations. For non-limiting example, as shown in an embodiment illustrated in FIG. 3, the system 10 can be accessible over a network 12 (e.g., over the Internet via cloud computing) from any number of client stations 14 in any number of locations such as a medical facility 16 (e.g., a hospital, an operating room (OR), a nurse's station, a medical device distribution facility, a medical device company, a hospital's sterilization, records, or billing departments, etc.), a home base 18 (e.g., a patient's home or office, a surgeon's home or office, etc.), a mobile location 20, and so forth. The client station(s) 14 can access the system 10 through a wired and/or wireless connection to the network 12. In an exemplary embodiment, at least some of the client terminal(s) 14 can access the system 10 wirelessly, e.g., through Wi-Fi connection(s), which can facilitate accessibility of the system 10 from almost any location in the world. As shown in FIG. 3, the medical facility 16 includes client stations 14 in the form of a tablet and a computer touch screen, the home base 18 includes client stations 14 in the form of a mobile phone having a touch screen and a desktop computer, and the mobile location 20 includes client stations 14 in the form of a tablet and a mobile phone, but the medical facility 16, the home base 18, and the mobile location 20 can include any number and any type of client stations. In an exemplary embodiment, the system 10 can be accessible by a client terminal via a web address and/or a client application (generally referred to as an "app").

It will be appreciated that the system 10 can include security features such that the aspects of the system available to any particular user can be determined based on the identity of the user and/or the location from which the user is accessing the system. To that end, each user can have a unique username, password, and/or other security credentials to facilitate access to the system 10. The received security parameter information can be checked against a database of authorized users to determine whether the user is authorized and to what extent the user is permitted to interact with the system, view information stored in the system, and so forth. Exemplary, non-limiting examples of parties who can be permitted to access the system 10 include patients, potential patients, significant others, friends, and family members of patients or potential patients, surgical technicians, imaging technicians (e.g., x-ray technicians, MRI technicians, etc.), surgeons, nurses, hospital administrators, surgical equipment manufacturer employees, insurance providers, and operating room directors.

Figure 4:
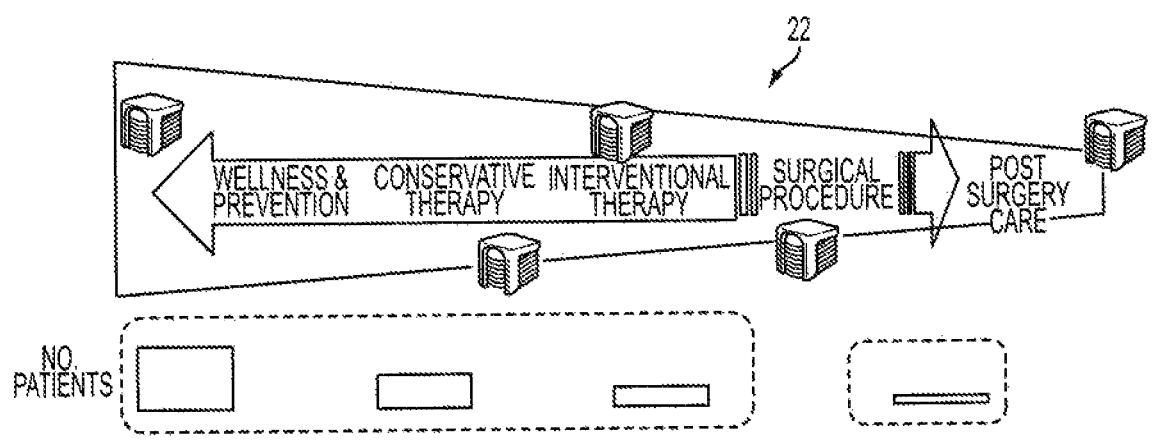
FIG. 4 is a schematic diagram of an embodiment of a continuum of patient care for the diagnosis, surgical planning, support, and management system of FIG. 2.

FIG. 4 illustrates an exemplary embodiment of a medical treatment continuum 22 throughout which the system 10 can facilitate diagnosis and treatment of patients. A patient can be tracked through a partial portion of the continuum 22 or through an entirety of the continuum 22. In this way, the system 10 can be effective for all patients, not just for patients treated with an invasive procedure such as surgery, needle procedures, biopsy, catheter based procedures, etc. As discussed herein, the system 10 can allow paths of an individual's medical treatment through all or part of the continuum 22 to be compared and consolidated then applied to patients with similar symptoms to diagnose and choose the treatment that previously produced a best outcome for similarly situated patients. The outcome can include technical, anatomic, functional, and patient reported parameters. FIG. 4 also illustrates how a number of patients in the continuum 22 is typically greatest in a wellness and prevention phase of the continuum 22, second greatest in a conservative therapy phase of the continuum 22, third greatest in an interventional therapy phase of the continuum 22, and least in surgical procedure and post-surgery phases of the continuum 22. Thus, by comparing and consolidating information regarding patients in the phases that typically involve a larger number of patients than invasively treated patients, the system 10 can help inform treatment of a larger number of patients than systems that focus only on surgical treatments and/or only on post-diagnosis. The continuum 22 also shows how data from all of the phases can be received by the system 10, thereby allowing pooling of data that can inform subsequent decisions in any one or more phases of the continuum 22, including phases different from where the data was originally collected.

The system 10 can include a diagnosis and treatment module 200, a pre-op module 202, an operation module 204, a post-op module 206, and a recovery module 208. Any of the diagnosis and treatment module 200, the pre-op module 202, the operation module 204, the post-op module 206, and the recovery module 208 can be used independently from one another and can be used in combination with any one or more of the other modules 200, 202, 204, 206, 208. In an exemplary embodiment, the diagnosis and treatment module 200, the pre-op module 202, the operation module 204, the post-op module 206, and the recovery module 208 can be provided as a comprehensive system that can track a patient throughout medical treatment including through initial onset of symptoms, diagnosis, non-surgical treatment, surgical and/or other invasive treatment, and recovery from the invasive treatment. Each of the modules 200, 202, 204, 206, 208 is discussed further below in turn. Although each of the modules 200, 202, 204, 206, 208 is illustrated in FIG. 2 as including a plurality of component modules, each of the modules 200, 202, 204, 206, 208 can include any number of component modules, e.g., one, two, three, etc., the same or different from any of the other modules 200, 202, 204, 206, 208. Further, as mentioned above, it will be appreciated that any of the modules 200, 202, 204, 206, 208, and any of their various component modules, can be subdivided or can be combined with other modules, including modules illustrated in FIG. 2 as being in different ones of the modules 200, 202, 204, 206, 208.

The system 10 can also include a diagnosis and treatment database 300 configured to be accessible by the diagnosis and treatment module 200 and to store diagnosis and treatment data, a pre-op database 302 configured to be accessible by the pre-op module 202 and to store pre-op data, an operation database 304 configured to be accessible by the operation module 204 and to store operation data, a post-op database 306 configured to be accessible by the post-op module 206 and to store post-op data, and a recovery database 308 configured to be accessible by the recovery module 208 and to store recovery data. Each of the databases 300, 302, 304, 306, 308 is discussed further below in turn with respect to their associated modules 200, 202, 204, 206, 208. Each of the databases 300, 302, 304, 306, 308 can include any number of component databases, e.g., one, two, three, etc., the same or different from any of the other databases 300, 302, 304, 306, 308. As mentioned above, it will be appreciated that any of the databases 300, 302, 304, 306, 308, and any of their various component databases, can be subdivided or can be combined with other databases, including databases illustrated in FIG. 2 as being in different ones of the databases 300, 302, 304, 306, 308. Any portion of any of the databases 300, 302, 304, 306, 308 can be configured to be accessed by any one or more of the modules 200, 202, 204, 206, 208. Although the system 10 in the illustrated embodiment stores data in database(s), any of the systems disclosed herein can store data in database(s) and/or in other data organization structure(s).

Users of the system 10 can include patients and medical practitioners involved with treating one or more of the patients. In some embodiments, the system 10 can be accessible by users other than patients and medical practitioners, such as by medical administrators, e.g., billing administrators, inventory controllers, etc. Different users can have access to different portions of the system 10, as mentioned above regarding security features. For non-limiting example, the system 10 can be configured to allow patients to access only the diagnosis and treatment module 200 and the recovery module 208, to allow medical administrators to access only the operation module 204, and to allow surgeons to access all of the modules 200, 202, 204, 206, 208. A user can have access to only a portion of a module, e.g., to only a subset of component modules within any one or more of the modules 200, 202, 204, 206, 208.

Diagnosis and Treatment Module

The diagnosis and treatment module 200 can generally provide users of the system 10 with an interface for managing patient wellness and prevention and for managing patient treatment at least until planning for any surgery begins. More particularly, the diagnosis and treatment module 200 can receive patient-specific data such as symptoms, provide diagnoses based on the patient-specific data, suggest medical practitioners experienced with particular diagnoses, provide conservative treatment options (e.g., non-surgical treatments) for particular diagnoses, provide coaching on reducing risk factors for pain through lifestyle changes, and provide interventional therapy treatment options (e.g., surgical treatments, needle procedures, biopsy, catheter based procedures, etc.) and/or pharmacological treatments for particular diagnoses. Indications of drugs and their potential interactions with existing medications can also be provided. In this way, the diagnosis and treatment module 200 can be configured to assist patient diagnosis and treatment through a continuum including patient onset of pain, patient arrival at a doctor, and a decision to pursue an invasive treatment such as surgery. In one embodiment, the diagnosis and treatment module 200 can be implemented using one or more web pages which are configured to receive user input and present information to a user. In an exemplary embodiment, both patients and medical practitioners can access at least a portion of the diagnosis and treatment module 200. In an exemplary embodiment, the diagnosis and treatment module 200 can be accessed by users via a web interface, e.g., by connecting to the Internet via a client terminal and accessing a specific web address, by launching an app on a client terminal that accesses the system 10, etc. As mentioned above, the users can wirelessly access the system 10, including the diagnosis and treatment module 200.

The diagnosis and treatment module 200 can include a diagnosis module 210, a treatment options module 212, a care provider module 214, and a treatment compliance module 216. Each of the modules 210, 212, 214, 216 is discussed further below in turn.

As mentioned above, the diagnosis and treatment module 200 can be configured to read information from and write information to the diagnosis and treatment database 300. The diagnosis and treatment database 300 can include a diagnosis database 310, a treatment database 312, and a care provider database 314. Various ones of the diagnosis and treatment module's component modules 210, 212, 214, 216 can be configured to access one or more of the diagnosis database 310, the treatment database 312, the care provider database 314, and/or various other databases, e.g., the pre-op database 302, the operation database 304, the post-op database 306, and the recovery database 308. Each of the databases 310, 312, 314 is discussed further below in connection with various ones of the diagnosis and treatment module's component modules 210, 212, 214, 216.

Diagnosis Module

The diagnosis module 210 can provide users of the system 10 with an interface for entering and evaluating symptoms and for receiving preliminary diagnoses based on the entered symptoms. The preliminary diagnoses can also be based on any one or more of prior treatments received by the patient, on physical examination data (e.g., signs noticed by a medical professional examining the patient), images of the patient, laboratory test results for the patient, patient demographic data, and/or on historical tests (e.g., genetic testing). Basing preliminary diagnoses on symptoms in addition to one or more other patient-specific factors can allow the diagnosis module 210 to provide more customized and better informed preliminary diagnosis information specific to a particular patient. The diagnosis module 210 can be configured to allow patients to enter their own symptoms for evaluation and possible diagnosis and to allow medical professionals to enter symptoms for their patients for evaluation and possible diagnosis. The diagnosis module 210 can also be configured to allow patients to enter previously received treatments for the symptoms, including self-treatments (e.g., over the counter medicine, etc.) and professionally-provided treatments. Each patient can be uniquely identified in the system 10, e.g., by name, identification code, etc., such that symptoms entered for a particular patient by the patient and by other user(s) can be stored in the diagnosis and treatment database 300, e.g., in the diagnosis database 310, as being associated with the patient. The patient's Electronic Medical Record (EMR) can be linked by their health care provider to the diagnosis and treatment database 300. The symptoms and historical treatments identified for a particular patient can be accessed at any time in the future using the system 10, which can help facilitate continued treatment and evaluation of the patient, e.g., by allowing severity of symptoms to be tracked over time as the patient and/or other user(s) updates the system 10. Symptoms for a patient can be stored in the diagnosis and treatment database 300, e.g., in the diagnosis database 310, with a date and time stamp, which can facilitate the continued treatment and evaluation of the patient. Similarly, other data discussed herein as being related to a particular patient can be stored in the diagnosis treatment database 300, the pre-op database 302, the operation database 304, the post-op database 306, and the recovery database 308 as being associated with the patient and as having a date and time stamp. The patient's EMR, historical treatments, images, lab results, physical exam results, symptoms, etc., to the extent they are provided to the system 10, can be compared to other patient data included in the diagnosis and treatment database 300 to compile outcome predictions based on retrospective results from treatment results of patients with similar indications. This compilation can allow medical care providers and patients to make more informed treatment and procedural decisions.

The system 10 can allow users to submit symptoms in a variety of ways. Other patient-specific factors can be submitted to the system 10 similar to that discussed herein regarding submission of symptoms. Patient-specific factors can be submitted to the system 10 by a patient or other user, e.g., the patient's primary care physician, a lab technician, etc. Additionally, the diagnosis module 210 and other modules discussed herein can be configured to consider patient-specific factors in making various determinations similar to that discussed herein regarding the modules' consideration of symptoms.

Figure 5:
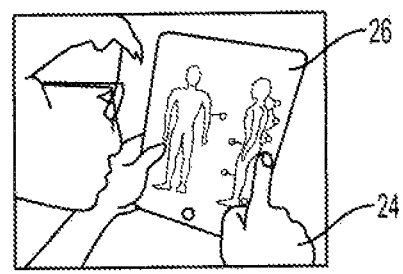
FIG. 5 is a perspective view of an embodiment of a client terminal that allows user input of data to the diagnosis, surgical planning, support, and management system of FIG. 2.

FIG. 5 illustrates one embodiment of symptom input to the system 10 by a user 24 via a client terminal in the form of a touch screen tablet 26. Although the touch screen tablet 26 is shown in the illustrated embodiment, the system 10 can allow for symptom selection in other ways, such as by other touch screen devices, by other client terminals, by mouse selection, by drop-down text menu, etc. The touch screen tablet 26 shows an interface allowing user selection of area(s) of a body in which symptom(s) manifest, but symptom(s) and their locations in the body can be identified and entered by a user in other ways, such as by text, pointer device selection (e.g., mouse clicking, touch via stylus pen, etc.), drop-down menu, etc. The diagnosis module 210 can be configured to provide the user with a variety of symptoms for selection based on the user's selected area(s) of the body in which symptom(s) manifest. The variety of symptoms can be stored in the diagnosis database 310 for selection based on a user's input and for display to the user. For non-limiting example, if a patient selects a hip area as having pain, the diagnosis module 210 can be configured to retrieve from the diagnosis database 310 one or more possible additional symptoms associated with hip pain, e.g., swelling, pain during movement, pain when stationary, stiffness following a period of inactivity, etc., that the user can further select to help better define the user's condition.

Figure 5A:
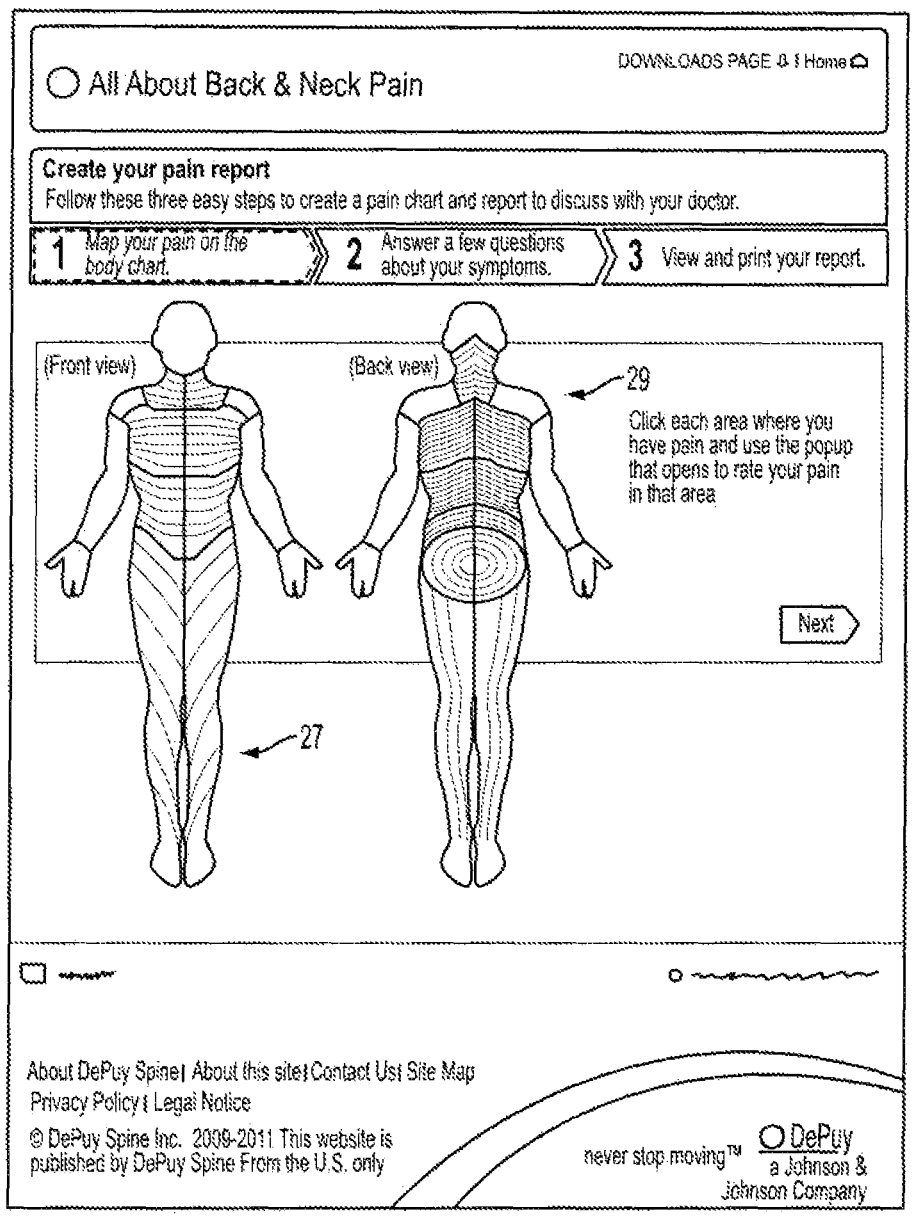
FIG. 5A is a schematic view of an embodiment of a user interface that allows user input of data to the diagnosis, surgical planning, support, and management system of FIG. 2.
Figure 5B:
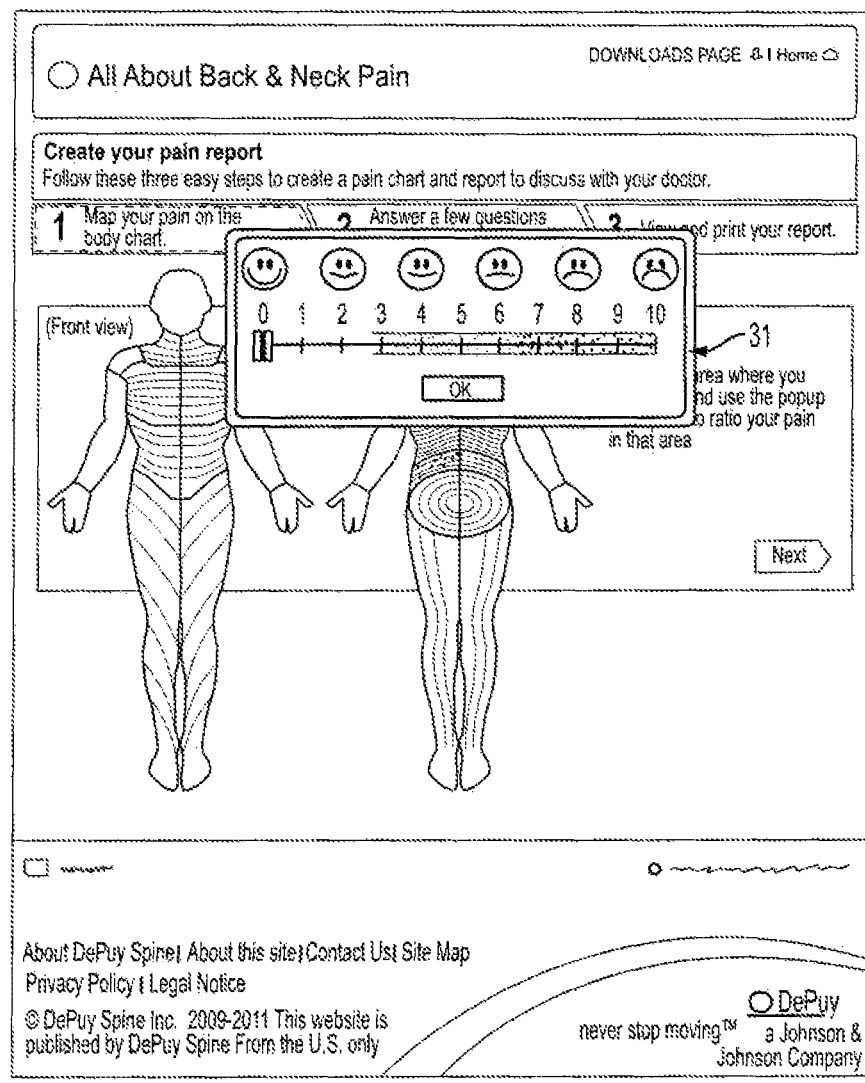
FIG. 5B is a schematic view of another embodiment of a user interface that allows user input of data to the diagnosis, surgical planning, support, and management system of FIG. 2.
Figures 5C, 6:
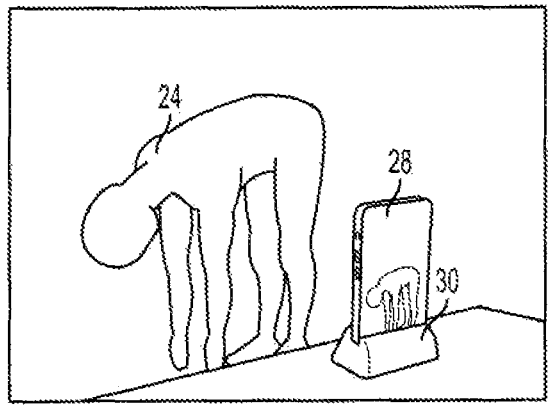
FIG. 5C is a schematic view of yet another embodiment of a user interface that allows user input of data to the diagnosis, surgical planning, support, and management system of FIG. 2.
FIG. 6 is a perspective view of another embodiment of a client terminal that allows user input of data to the diagnosis, surgical planning, support, and management system of FIG. 2.

FIGS. 5A-5C illustrate one embodiment of a user interface 25 configured to be provided on a client terminal and to allow user input of data to the system 10. The user interface 25 relates to entry of input of data regarding back and neck pain, but as mentioned above, data regarding any one or more symptoms can be input into the system 10. As shown in FIG. 5A, the user interface 25 can be configured to allow a user to select one or more portions of a body on a body chart where pain is being experienced. The body chart can include a front view body chart 27 and a back view body chart 29, each body chart 27, 29 providing predetermined areas that can be selected by the user. As shown in FIG. 5B, for each selected body portion, the user can be prompted to indicate a level of pain experienced in that selected body portion by using a sliding scale 31 ranging from zero (near a smiling face graphic) indicating no pain to ten (near a frowning face graphic) indicating extreme pain. Levels of pain can be input in any number of other ways, such as by entering a numerical level of pain from zero to ten in a text entry field, etc. The sliding scale 31 can be provided in a pop-up window, as shown in the illustrated embodiment, or can be a separate screen on the client terminal. The user can also be prompted to answer one or more questions about their symptoms, as shown in FIG. 5C. Examples of questions include identification data (e.g., name, birthdate, age, medical record number, etc.), "How long have you had your symptoms?", "Which one of the following best describes the amount of pain you have experienced during the past six months?" (none, mild, moderate, moderate to severe, severe), "Which one of the following best describes the amount of pain you have experienced during the past one month?" (none, mild, moderate, moderate to severe, severe), "During the past six months have you been a very nervous person?" (no, a little, some, most of the time, all of the time), "What is your current level of activity?" (bedridden, primarily no activity, light labor and light sports, moderate labor and moderate sports, full activities without restriction), "How do you look in clothes?" (very good, good, fair, bad, very bad), "Do you experience pain when at rest?", "What is your current level of work/school activity?", "Does your pain limit what you do around the house?", "Does your condition affect your personal relationships?" (no, slightly, mildly, moderately, severely), "Have you been a happy person in the past six months?", "Would you have the same pain management again if you had the same condition?" (definitely yes, probably yes, not sure, probably not, definitely not), etc. In an exemplary embodiment, the questions can help pinpoint location, quality, and duration of the symptoms; precipitating events or circumstances; exacerbating and relieving factors; and any changes over time.

FIG. 6 illustrates another embodiment of symptom input to the system 10 by the user 24 via electronic image collection by a client terminal in the form of a mobile phone 28. The user 24 can launch an app on the mobile phone 28 configured to electronically communicate with the diagnosis and treatment module 200, e.g., interface with the system 10 via the network 12 using electronic signals transmitted wirelessly and/or using wired connection(s). The app can be configured to capture data, e.g., one or more still images and/or one or more videos, indicating one or more physical characteristics of the patient 24, e.g., a range of motion of the patient 24, an amount of swelling, skin discoloration, etc. The captured data can be saved in the diagnosis database 310. The captured data can be helpful in evaluating symptoms involving, e.g., joint issues and back pain, and/or can be helpful in tracking changes in the patient over time, e.g., scoliosis curve progression can be monitored over time and/or predicted into the future as pediatric patients grow. The mobile phone 28 can be stably situated, e.g., via phone stand 30, to help provide stable images to the system 10. The diagnosis and treatment module 200 can be configured to prompt the user to collect specific images, e.g., one or more images of the user from a certain angle, a video of the user performing a certain task, a video of a user holding a certain position for a certain amount of time, etc. The prompt can be based on one or more factors, such as previously collected images of the patient (e.g., want to collect images over time with each image being from a same angle), preference of the user's primary care physician (e.g., always urge video collection over still image collection), the user's entered symptoms (e.g., ask the user to capture an image of the user attempting to touch their toes if back pain is submitted as a symptom), etc.

Although an app is used to collect data in the illustrated embodiment, a person skilled in the art will appreciate that data can be captured in other ways and that devices other than mobile phones can be used to collect the data with or without running an app. A person skilled in the art will appreciate that data can be captured in a variety of ways, e.g., using a camera (standalone or integrated into another device such as a mobile phone or tablet); a video camera (standalone or integrated into another device such as a mobile phone or tablet); one or more sensors (e.g., gyro, accelerometer, global position system (GPS), etc.) on a smartphone, in a skin patch (e.g., patches available from MC10 Inc. of Cambridge, MA), integrated into smart clothing, or in additional sensing or monitoring devices that can connect to the client terminal via wireless or wired connection, etc.; any of a variety of known motion capture apps or motion capture software; etc.

In another embodiment, a user, e.g., a patient, can use a head-mounted neural mapping device, e.g., an accelerometer, under medical supervision to collect and submit neural mapping data to the diagnosis database 210. Neural mapping data can be helpful in determining and quantizing pain levels of a patient. Over time, the neural mapping data and the patient's self-described pain can help the system 10 learn objective pain levels, e.g., normalize pain levels to allow a more objective evaluation of pain.

By being accessible over a network, the system 10 can allow users to enter symptom information to the diagnosis module 210 when a patient is remote from a medical setting (e.g., doctor's office, hospital, clinic, etc.) and when the patient is in a medical setting. Allowing a patient to submit their own symptoms to the system 10 can result in one or more benefits. A patient can better determine whether and when it would be appropriate to see a medical professional because the system 10 can provide a recommendation of whether and when to visit a medical professional in person based on the patient's specific symptoms, thereby saving both the patient's and the medical professional's time. If and when a patient visits a medical professional, the medical professional can access the system 10 to evaluate the patient's symptoms even before the patient personally discusses their symptoms with the medical professional, which can allow the medical professional to better focus their in-person time with the patient, e.g., ask more informed questions, be prepared to perform certain tests, etc. Having symptoms stored in the diagnosis and treatment database 300 can help prevent the patient from forgetting to mention certain symptoms to a medical professional in person and/or from forgetting particular onset and/or timing of certain symptoms because the symptoms will already be logged in the system 10. The medical professional can therefore be better able to provide diagnosis and treatment information to the patient because the information can be based on a more complete and accurate picture of the patient's condition. The system 10 can capture transient symptoms, e.g., hives, spasms, etc., that may not manifest when the patient is at a doctor's office or otherwise in direct observation of a medical professional. These captured transient symptoms, e.g., recorded and stored audio, video, and/or still image, can allow a medical professional to more fully evaluate a patient's condition by being able to directly observe the transient symptoms without having to rely solely on a patient's memory and/or on a patient's unintentionally inaccurate and/or medically imprecise description of transient symptoms.

By allowing users other than the patient to submit symptoms to the system 10 for a patient, the system 10 can allow for symptoms to be logged that may be overlooked by a non-medically trained person as not being significant and/or can ensure a more complete record of symptoms. The system 10 can therefore have more complete knowledge of a patient's symptoms and thus better analyze a patient's condition so as to provide a more accurate diagnosis and/or more effective treatment plan for the patient. The system 10 can allow users of the system other than the patient to link and/or upload previously collected patient data, e.g., prior medical history, demographics information, etc., to the system 10, which can allow the system 10 to better analyze information regarding a patient because more data can be taken into account for various analyses. Exemplary embodiments of uploading data such as images are described in more detail in U.S. patent application Ser. No. 13/603,452 entitled "Systems And Methods For Surgical Support And Management" filed Sep. 5, 2012, which is hereby incorporated by reference in its entirety.

The diagnosis module 210 can be configured to analyze symptoms entered by a patient, determine at least one possible diagnosis based on the entered symptoms, and provide the at least one possible diagnosis to the user, such as by causing a display screen (e.g., a screen of the same device the user used to enter the symptoms) to show a list of the diagnos(i/e)s. The possible diagnos(i/e)s can be provided to the user with a caution that the diagnos(i/e)s are preliminary only and that a user must consult a doctor for a complete evaluation and diagnosis.

The diagnosis module 210 can be configured to analyze the symptoms for a patient entered by one or more users and determine the at least one preliminary diagnosis in a variety of ways. In an exemplary embodiment, the diagnosis database 310 can include a plurality of possible diagnoses, each of the possible diagnoses being associated with a plurality of symptoms. This diagnosis data can be organized in any way, such as in a table. The diagnosis module 210 can be configured to compare user-entered symptoms with the plurality of possible diagnoses stored in the diagnosis database 310 and determine which of the plurality of possible diagnoses are associated with symptoms matching the user-entered symptoms. The diagnosis module 210 can be configured to compare gathered neural mapping data for a patient with pain level data about the patient previously entered by another user, e.g., by the patient, and/or with previously determined neural maps stored in the diagnosis database 310. The diagnosis module 210 can thus be configured to learn an objective way to measure pain, and to create a pain thermometer based on data from a plurality of patients, rather than rely on a particular patient's pain numbers. Additionally, as mentioned above, the diagnosis module 210 can be configured to analyze any one or more patient-specific factors in addition to symptoms in determining a diagnosis.

The diagnosis module 210 can be configured to determine a diagnosis based on a patient's entered patient specific-factors matching predetermined attributes or criteria. Each of the diagnoses in the diagnosis database 310 can be associated with predetermined criteria. Each of the criteria can include a plurality of attributes such that each of the diagnoses are associated with a combination of attributes that define patients having that diagnosis. In other words, the predetermined criteria can define patient-specific factors associated with a diagnosis such that if a patient's factors match the criteria, the diagnosis module 210 can identify that diagnosis for the patient. The predetermined criteria can also define patient-specific factors that exclude a particular diagnosis such that if a patient has a factor that matches the exclusion factor included in the criteria, the diagnosis module 210 can exclude that diagnosis for the patient. The predetermined criteria for a diagnosis can thus include inclusion criteria (e.g., attributes associated with the diagnosis) and exclusion criteria (e.g., attributes excluding the diagnosis). The diagnosis module 210 can be configured to provide a confidence level with a determined diagnosis based on the patient's factors matching with the predetermined criteria. The confidence level can reflect a number of the predetermined criteria that are matched for a particular patient. In an exemplary embodiment, the confidence level can be provided as a percentage of attributes matched for a patient (e.g., 75% match, 95% match, 80% match, etc.) and/or as a number of attributes matched (e.g., 7 of 8 attributes matched, 18 of 18 attributes matched, etc.). If a patient matches all a diagnosis's attributes, the diagnosis module 210 can be configured to indicate that the patient is a "perfect" match. Correspondingly, if a patient does matches most but not all a diagnosis's attributes, the diagnosis module 210 can be configured to indicate that the patient is not a "perfect" match but is a "possible" match or, if more attributes are matched, a "likely" match.

The diagnosis module 210 may determine that the user's entered symptoms do not match any of the stored plurality of possible diagnoses, e.g., no one of the plurality of possible diagnoses includes all of the user's entered symptoms. In such a case, the diagnosis module 210 can be configured to inform the user that no matching diagnoses were located and/or the diagnosis module 210 can be configured to determine one or more "best guess" diagnoses based on, e.g., which one or more of the stored possible diagnoses match a majority of the user's entered symptoms.

The diagnosis module 210 can therefore be configured as a preliminary diagnosis mechanism that collects various patient data, can help inform a patient of one or more possible causes of their symptoms, and can help inform medical practitioner(s) treating the patient of possible diagnoses to consider upon evaluation of the patient, either in person and/or upon review of the user's entered data. Thus, even before a patient visits a medical care practitioner in person, or even if a patient never visits a medical care practitioner in person, the patient can receive information regarding their symptoms, which can facilitate speedy treatment. The diagnosis module 210 can also help inform medical practitioners about conditions with which they have less familiarity with, which can help train the medical practitioners, make their job easier, and provide better outcomes through instant education of the medical practitioners. The diagnosis module 210 can be configured to determine and report differential diagnosis, with ranked appropriate diagnoses and confidence levels for each assigned diagnosis, which can help a medical professional make more informed decisions regarding patient diagnosis and/or treatment. The diagnosis module 210 can be configured to capture a plurality of coexisting diagnosis, e.g. metastatic tumor and fracture, scoliosis and myelopathy, etc. Since the diagnosis module 210 can capture all ongoing treatments, therapies and medicines to which the patient has been exposed, the potential for dangerous drug interaction or hazardous interactions with different therapies can be avoided through automated warnings provided by the system 10 to, e.g., a surgeon, nurse, pharmacist, and/or patient.

The diagnosis module 210 can allow a medical practitioner to manually enter diagnosis information for a patient to be stored in the diagnosis database 310 for the patient. This manually entered diagnosis information can be based on symptom data input to the system 10 or can be based on other data and analysis, e.g., data collected outside the system 10 and analyzed by the medical practitioner. By allowing diagnosis information to be directly entered into the system 10, the system 10 can help manage treatment of the patient through a continuum of treatment following an initial diagnosis. The system 10 can therefore be seamlessly integrated into a medical practitioner's current practice, a hospital setting, etc. in which at least some patients already have diagnoses for various illnesses, injuries, and diseases. Similarly, the system 10 can allow manual entry of other information mid-way through a patient's diagnosis and/or treatment, such as a patient's treatment plan, so as to allow seamless integration of the system 10 into a patient's medical care.

By way of example, the system 10 can be used in a spinal context, such as to test for the presence of cytokines (such as Fibronectin-aggrecan complex, FAC) and growth factors (such as TNF-alpha or IL-8) in the intervertebral disc of patients, in specifically DDD or herniated disc cases in the lumbar, thoracic, or cervical spine. The system 10 can prompt a physician to run this test as a result of the system's review of a patient's symptoms. The result of the test can be stored in the diagnosis database 310 and used in the diagnosis of the patient and in recommending the use of certain treatments such as epidural steroid injections, e.g., Enbrel or Remicade (TNF antagonists). As the system 10 continually runs these tests on more patients, and then subsequently tracks the test's validity in diagnosing the patient's condition by relating it to the patient outcome of the chosen surgical treatments for DDD and/or herniated disc, the system 10 will gain a more refined intelligence of when to prescribe the test, and when to prescribe certain medications and/or treatments (invasive or non-surgical) based on the results of the test. The system 10 can also be configured to receive the raw data of the test, and through the statistical power created by continually comparing these granular results with chosen treatments and patient outcomes, the system 10 can further refine the analysis of the chemical components of the test and more accurately relate them to diagnoses, treatments, and outcomes. Alternately, the system 10 can be configured to record the DNA data for each patient in the diagnosis database 310, provided by a sequencing test, and run an algorithm that analyzes and compares the DNA markers for patients with similar pain diagnoses. Over time, this continual comparison will result in the system 10 identifying markers that predict patients to be at a higher risk for certain spinal disorders. This identification will help in the initial diagnosis phase to develop an appropriate treatment plan based on the existence of these high-risk markers in combination with the patient's symptoms. For example, if there are clear markers that indicate that the condition will only worsen with time and that surgical intervention will be necessary, then a less invasive surgery can be done early before the condition worsens and results in more pain and disability. If the patient is lacking high risk markers, then a more conservative treatment would be recommended as a first course of action.

For another example, the diagnosis module 210 can include an algorithm, alone or in combination with the treatment options module 212, that can be configured to analyze inputs such as an MRI or CT scan of a patient so as to automatically detect specific features contained in inputs that are related to specific pathologies. Based on the analysis, this auto diagnosis algorithm can provide feedback to the user of the pathologic issue that has been discovered for consideration in determining diagnosis, along with treatment recommendations, as determined in concert with the other system inputs. In an exemplary embodiment, the algorithm can have pre-programmed pathologies to look for, such as collapsed disc space (shorter than a determined height) and a loss of signal in the spinal cord. These pre-programmed pathologies can have related treatment methods predefined in the diagnosis module 210 and/or the treatment options module 212. As the system 10 collects more data, the system 10 can be able to compare these analyses and recommendations to the functional outcomes across patients, and can learn how accurate pre-programmed inputs to the system 10 were, and adjust as necessary to increase the accuracy of the auto diagnosis based on this result. The system 10 can be configured to perform further analysis to autonomously develop its own criteria for assessing the inputs (e.g., the MRI or CT scans) by using the data collected in the diagnosis and treatments database 300 and/or the recovery database 308 to find common anomalies between patients and the treatments that are most successful in addressing them.

Treatment Options Module

The treatment options module 212 can provide users of the system 10 with an interface for receiving one or more treatment options based on the preliminary one or more diagnoses determined by the diagnosis module 210. A user can receive treatment option(s) for each of the determined preliminary diagnoses, or the treatment options 212 module can allow the user to particularly select one or more of the preliminary diagnoses to receive treatment option(s) therefor from the system 10.

The treatment options module 212 can determine the treatment option(s) in a variety of ways. In an exemplary embodiment, the treatment database 312 can include a plurality of possible treatment options, each of the possible treatment options being associated with at least one possible diagnosis. This treatment options data can be organized in any way, such as in a table. The treatment options module 212 can be configured to assemble composite patient data points in real time, until the search crosses a predetermined threshold for meeting an optimal constellation of findings that most perfectly match with a certain treatment option. The treatment options module 212 can be configured to screen for all known contraindications and relative contraindications simultaneously. If key elements of these are found to be unknown, the treatment options module 212 can be configured to query the user to provide the missing data before suggesting any treatment. The treatment options module 212 can be configured to compare a possible diagnosis with the plurality of treatment options stored in the treatment database 312 and determine which of the plurality of possible treatment options are associated with the possible diagnosis based on prior treatments and outcomes that have been uploaded to and stored in the treatment database 312. This comparison can be performed automatically by automatically reviewing the stored data. The information loaded to the system 10 regarding prior patients can include a plurality of specific variables or attributes for each patient and treatment type that can be compared and grouped in numerous combinations automatically by the system 10. Examples of the variables include patient age, height, weight, pain levels, scan images (e.g., MRI, CT, x-ray, etc.), range of motion, lifestyle behaviors (e.g., smoking, exercise, etc.), bone density, disc degeneration, pain locations, type of procedure performed, bone removed, disc removed, implants used, pharmaceuticals administered, reduction in pain, return to work, fusion rate, and functional outcome. Collection of the specific variables for each patient can allow the system 10 to automatically and continually review the data and discover trends in the variables between patients and relate these trends to patient type, procedure type, and functional outcomes. These relationships can be evaluated by the system 10 through multiple algorithms in the diagnosis and treatment module 210 to provide more accurate recommendations of treatments for the patient and their symptoms to result in an optimized outcome.

The treatment options module 212 can be configured to determine a treatment using predetermined criteria similar to that discussed above regarding the diagnosis module 210 using predetermined criteria to determine a diagnosis.

The treatment options module 212 can be configured to cause a display screen (e.g., a screen of the same device the user used to enter the symptoms) to show a list of the possible treatment option(s). The possible treatment option(s) can be provided to the user with a caution that the possible treatment option(s) are preliminary only and that a user must consult a doctor for a complete evaluation and treatment plan. The possible treatment option(s) can be provided to the user with historic success rates of each of the possible treatment option(s). The historic success rates can be stored in the treatment database 312 for each of the treatment options and can be manually entered. Alternatively or in addition, the historic success rates can be based on data collected by the system 10 regarding a plurality of patients, e.g., HRQOL, health economic data, etc., such that the system 10 can act as a feedback loop system in which previously collected data regarding treatments received by actual patients can inform treatment options suggested to future patients. The possible treatment option(s) can be provided to the user with educational resources for at least one of the options, e.g., links to informational web pages stored in the system 10 (e.g., in the treatment database 312), links to third party educational websites, lists of or links to journal articles or books, educational video of a surgical procedure that is stored in the system 10 (e.g., in the treatment database 312), links to medical device product brochures (e.g., brochures stored electronically in the system 10), etc.

In some embodiments, the treatment options module 212 can provide coding and reimbursement information for each of the suggested treatment options. Providing such information can facilitate educated decision-making about which of the treatment options to pursue (if any).

In some embodiments, the treatment options module 212 can be configured to consider one or more factors other than patient symptoms in determining treatment option(s) to suggest for a patient. Considering such factors can allow a potential success rate of various treatment options to be considered by the treatment options module 212 in suggesting particular treatment options for a patient. Such factors can include any one or more of a patient's age, medical practitioner treatment preferences previously logged in the treatment database 312, a patient's bone density, a patient's medical history, prior surgery performed on the patient, discography, a compliance rate of the patient with prior non-surgical treatments, leak rate studies, patient images (e.g., x-rays, magnetic resonance imaging (MRI) images, x-ray computed tomography (CT) scans, etc.), test results data from lab tests, etc.

Figure 7:
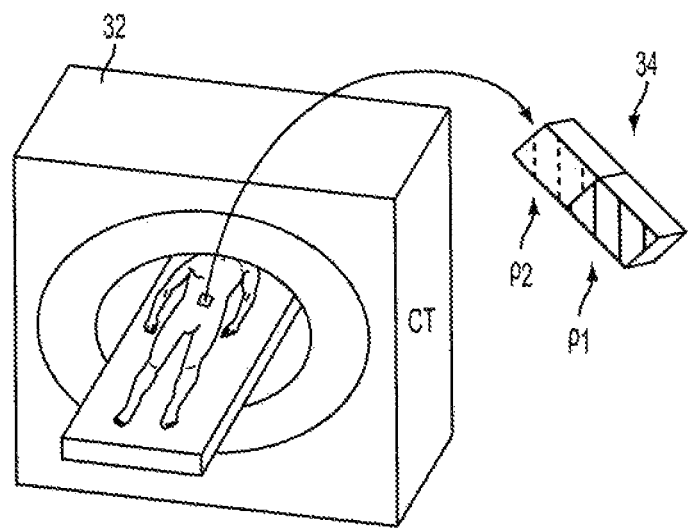
FIG. 7 is a perspective view of an embodiment of a bone density marker system that provides bone density information to diagnosis, surgical planning, support, and management system of FIG. 2.

FIG. 7 illustrates an embodiment of obtaining accurate bone density information for a patient using a CT scanning machine 32 and a bone density marker 34. The bone density marker 34 can include a first material having a first density $\rho_1$ on one side, e.g., right side, of the marker 34 and a second material having a second density $\rho_2$ next to the first material on an opposite side, e.g., left side, of the marker 34. The marker 34 can be placed on and/or under a patient scanned by the CT machine 32. By knowing the densities $\rho_1$, $\rho_1$ of the marker 34, a correlation can be made to the grey scale output of the CT scan. Densities of any pixel in the CT scan can therefore be determined. The patient's bone density can therefore be determined by analyzing pixels showing bone in the CT scan. The treatment options database 210 can be configured to consider the patient's bone density data in determining suggested treatment options for the patient, e.g., suggest treatment options with very low impact exercise if a patient has very low bone density, suggest no surgical treatments if bone density is too low, etc.

The possible treatment options suggested by the treatment options module 212 can include non-surgical treatment options (e.g., diet adjustments, exercise regimens, medications, etc.) and invasive treatment options such as surgical treatment (e.g., specific surgical procedures), needle procedures, biopsy, and catheter based procedures. In an exemplary embodiment, only non-surgical treatment(s) can be initially suggested to a user of the system 10. In this way, a conservative treatment can be pursued before a more radical, typically more costly treatment such as surgery is pursued. If one or more of the non-surgical treatments are pursued and are determined to unsatisfactorily address a patient's problem(s), then the treatment options module 212 can be configured to suggest one or more invasive treatment options. The suggestion invasive treatment options can each include procedure type and, if appropriate, implant options. The treatment options module 212 can be configured to suggest the one or more invasive treatment options upon request by a user, e.g., when a medical practitioner requests non-conservative treatment options for a particular patient, and/or can be configured to suggest the one or more invasive treatment options when a trigger event occurs, e.g., after a predetermined threshold amount of time passes from commencement of a non-surgical treatment for a patient after which the patient has not shown a predetermined amount of improvement. By way of non-limiting example, the treatment options module 212 can be configured to analyze data gathered by the diagnosis module 210 and/or the treatment compliance module 216, discussed further below, and determine whether the patient's mobility has improved by a certain degree after a certain amount of time as indicated by reported pain levels and/or analysis of captured images. Before the treatment options module 212 suggests one or more invasive treatment options following determination that a non-surgical treatment is not achieving a desired outcome, the treatment options module 212 can be configured to first suggest one or more other non-surgical treatments.

By suggesting treatment option(s) to a user, the diagnosis and treatment module 200 can allow the user to receive and analyze information that may be outside their area of medical expertise. For non-limiting example, a general medical practitioner such as a patient's primary care physician (PCP) may not be very familiar with specific spine injuries or deformities. The diagnosis and treatment module 200 can allow the PCP to enter a patient's spinal symptoms (e.g., to the diagnosis module) and receive a suggested treatment (e.g., from the treatment options module 212) for the spine-related symptoms. The PCP can therefore provide speedier, more detailed diagnosis information to the patient, as well as direct the patient to a specialist and/or advise appropriate care, more quickly, and likely more accurately, than if the PCP had to rely on traditional diagnosis and treatment assistance tools such as print or electronic books, print or electronic articles, and consultation with colleagues. The PCP can still consult the traditional diagnosis and treatment assistance tools. Additionally, the PCP can become better informed about spinal issues through use of the diagnosis and treatment module 200 for the patient with spine-related symptoms, which can help the PCP train residents, educate colleagues, educate patients, and treat future patients having similar symptoms.

The treatment options module 212 can include a patient consent of treatment form where password protected signature approval is obtained from the patient noting a full understanding of options and agreement to provider prescribed treatment(s). This form and signature can be stored in the patient record of the diagnosis and treatment database 300 and can be linked to the patient's EMR.

Care Provider Module

The care provider module 214 can provide users of the system 10 with an interface for receiving a recommendation of one or more medical practitioners to treat a patient based on one or more of the preliminary one or more diagnoses determined by the diagnosis module 210, the one or more treatment option(s) determined by the treatment options module 212, and the patient's geographic location. The care provider database 314 can include data regarding a plurality of medical practitioners, each of the medical practitioners being associated with at least one geographic location, at least one area of medical practice, at least one previously performed surgical procedure, and/or at least one previously provided medical treatment. This care provider data can be organized in any way, such as in a table.

The care provider module 214 can be configured to compare at least one of the preliminary diagnoses determined by the diagnosis module 210, the treatment option(s) determined by the treatment options module 212, and the patient's geographic location with the data stored in the care provider database 314 to determine one or more medical practitioners associated with the preliminary diagnoses determined by the diagnosis module 210, the treatment option(s) determined by the treatment options module 212, and/or the patient's geographic location so as to be appropriate for the patient to consult for further medical information and/or treatment. The care provider module 214 can be configured to cause a display screen (e.g., a screen of the same device the user used to enter the symptoms) to show a list of the possible care provider(s). The list can include information regarding the care provider(s) such as name, address, gender, phone number, affiliated hospital, any accepted insurance plans, website, and/or area of medical specialty. The care provider module 214 can be configured to provide access to outcomes for affiliated hospitals and for physicians performing the potential treatments. The outcomes can be stored in the care provider database 314. The outcomes can be provided for review by, e.g., the patient, the patient's family, the patient's caregiver, the patient's primary care physician, etc. The care provider module 214 can therefore assist patients in locating a medical practitioner near the patient and/or with particular skill related to the patient's possible diagnosis and/or possible treatment.

Treatment Compliance Module

The treatment compliance module 216 can provide users of the system 10 with an interface for tracking patient compliance with a treatment plan. The treatment plan can be one of the suggested treatment options suggested by the treatment options module 212, can be one of the suggested treatment options suggested by the treatment options module 212 as modified by a medical practitioner, or can be a treatment plan entered into the system 10 by a medical practitioner without assistance of the treatment options module 212. The treatment plan can be stored in the treatment database 312. The treatment compliance module 216 can thus allow monitoring and management of a patient's treatment, which can help the patient's doctor evaluate the patient's progress and/or can help determine whether and when modifications to the treatment plan may be necessary, such as by adjusting the treatment plan (e.g., changing dietary requirements, changing a frequency of doctor check-ups, etc.) or replacing the treatment plan (e.g., a non-surgical treatment) with another treatment plan (e.g., a surgical treatment).

Patients and users other than patients can submit data to the treatment compliance module 216 for storage in the treatment database 312. Data can therefore be received by the treatment compliance module 216 whether the patient is or is not in a medical setting and can be received throughout the patient's treatment, including times other than when the patient visits or consults a medical practitioner. More accurate and more timely data regarding treatment plan compliance can therefore be gathered and analyzed.

Patient compliance response to medicinal treatments can be monitored, e.g., by a patient's treating physician, by viewing compliance data stored in the treatment database 312, which can allow dose level changes to be made more readily by, e.g., the treating physician. Simple at-home diagnostic tools can be used to monitor components within blood, urine or other fluids. This at-home diagnostic tool information can allows the patient's physician to adjust medicinal dosages to the individual patient. The treating physician can change the dose of the medicine to the needs of the patient based upon the information tracked and recorded. Other at home tools can be additionally or alternatively monitored; such as results of self-administered ultrasound images, photographs of incision sites, microscopic photos of areas of concern, etc. These other at-home tools can be uploaded to the patient's record in the treatment database 312, where the data can be accessed and reviewed by, e.g., the patient's surgeon.

Users can submit data to the treatment compliance module 216 similar to that discussed above regarding submission of data to the diagnosis module 210. Non-limiting examples of compliance data that can be gathered by the treatment compliance module 216 include exercise performed, medication taken, daily diet, physical therapy attended/performed, physiological data such as heart rate, patient geographic location, pain, neurologic tracking, bone alignment (e.g., spine curvature, etc.), and patient movement (e.g., mobility, gait, walking speed, flexibility, muscular strength, posture, range of motion, joint movement, etc.). The treatment compliance module 216 can be configured to accept manual entry of compliance data by a user, e.g., submission of types and lengths of physical therapy, and to accept automatically gathered compliance data, e.g., smartphone or bracelet location and movement tracking data. The treatment compliance module 216 can be configured to automatically gather data at predetermined time intervals, e.g., every sixty minutes, every twenty-four hours, every Sunday morning, etc., which can help allow for more accurate comparison of data gathered at different times and/or on different days. Additionally or alternatively, the treatment compliance module 216 can be configured to automatically gather data upon detection of a trigger event, such as use of a pedometer, e.g., automatically gather pedometer data when the patient walks/runs so as to increase the pedometer's count. The treatment compliance module 216 can be configured to prompt a user for specific compliance data and/or prompt the user to enter compliance data at specific dates and/or times. The treatment compliance module 216 can be configured to allow for scanning of medications taken and patient compliance data acquisition at times correlated with medication intervals, e.g. directly before, one hour after, two hours after, four hours after, eight hours after, etc.

The treatment compliance module 216 can be configured to analyze received compliance data to determine a compliance level and/or a success rate of the treatment overall and/or per symptom. The compliance level and/or the success rate can help a medical practitioner and/or the treatment compliance module 216 determine whether modification of a patient's treatment plan is necessary.

The treatment compliance module 216 can be configured to compare received treatment compliance data for a patient with historic compliance data for other patients who underwent similar treatment to help determine the effectiveness of the treatment for the patient. The comparison can allow the treatment compliance module 216 to determine whether a patient is adequately following the treatment plan or is lagging behind historical benchmarks achieved by other patients undergoing the treatment. The comparison can also allow the treatment options module 212 to evaluate treatment options for future patients because if a treatment is historically shown to be problematic for any one or more reasons (e.g., difficulty in achieving patient compliance, slow progress in addressing symptoms, expensive, lack of insurance payments, etc.) or shown to be particularly effective for any one or more reasons (e.g., patient mobility consistently increases, non-surgical treatment usually not followed by surgery, etc.), the treatment options module 212 can be more likely (for particularly effective treatments) or less likely (for problematic treatments) to recommend the treatment for future patients.

Because the treatment compliance module 216 can be configured to simultaneously and continuously receive information regarding multiple patients, the diagnosis and treatment module 200 can continually analyze received data to help determine efficacy of a particular patient's treatment plan. The diagnosis and treatment module 200 can thus determine that a particular patient's treatment plan should be modified based on another set of patients' data indicating low or high effectiveness for a particular treatment aspect, such as a specific exercise performed daily. In other words, the diagnosis and treatment module 200 can learn from other patients' experiences that the present patient's treatment could benefit from a modification, e.g., perform a specific exercise once every other day instead of once daily, cease performance of a particular exercise, decrease salt intake, wear a knee brace 24/7 instead of only while sleeping, etc. The diagnosis and treatment module 200 can be configured to suggest the modification of the patient's treatment plan to the patient's care provider, e.g., by providing an alert (e.g., email message, text message, instant message, phone call, etc.) to the care provider indicating that modification of the patient's treatment plan is recommended. The care provider can review the modification, e.g., by logging onto the system 10, and determine whether to modify the patient's treatment plan. Alternatively, the diagnosis and treatment module 200 can be configured to automatically modify the patient's treatment plan and inform the patient via an alert as to the modified treatment plan. Usually, however, a care provider would review a modification to check its appropriateness for the particular patient before the diagnosis and treatment module 200 automatically modifies the patient's treatment plan and informs the patient of the change.

The treatment compliance module 216 can be configured to provide feedback to the patient regarding their compliance, which can help ensure that a patient complies with the plan as much as possible and/or can help show the patient that the plan is effectively treating the symptom(s) or that the symptom(s) are not dissipating, in which case the patient can be prompted to contact their care provider for consultation. The compliance feedback can be provided in a variety of ways. Non-limiting examples of compliance feedback include a percentage indicating degree of compliance with all plan aspects; a model of bone alignment over time; a graph of mobility over time; connection with or comparison to other patients with similar symptoms, diagnoses, and treatment plans as a way to compare progress and provide motivation to the patient to comply with their treatment plan by being inspired by the progress of others in their peer group; etc.

Pre-Op Module

The pre-op module 202 can generally provide users of the system 10 with an interface for planning surgery, e.g., doctor's office pre-op planning, operating room (OR) pre-op planning, and patient pre-op planning. More particularly, the pre-op module 202 can allow surgeons to electronically perform three-dimensional (3D) simulated surgeries on virtual models of patients to test surgical ease and/or potential surgical outcomes before actually performing the surgical procedure. The simulated surgeries can include variations of the same surgical procedure on a patient so as to try different surgical instruments and/or different surgical strategies. The pre-op module 202 can also facilitate logistical surgical planning such as equipment ordering and supply, OR scheduling, and personnel scheduling. The pre-op module 202 can also facilitate the logistics of preparing the patient for surgery, such as by managing patient pre-op requirements and activities before and after the patient arrives at the hospital. In this way, the pre-op module 202 can be configured to assist pre-op planning and management through a continuum from a decision to pursue surgery to the patient's arrival at an OR for surgery. In one embodiment, the pre-op module 202 can be implemented using one or more web pages which are configured to receive user input and present information to a user. In an exemplary embodiment, both patients and medical practitioners can access at least a portion of the pre-op module 202.

The pre-op module 202 can include a surgical procedure module 218, an equipment management module 220, a scheduling module 222, and a patient preparation module 224. Each of the modules 218, 220, 222, 224 is discussed further below in turn.

As mentioned above, the pre-op module 202 can be configured to read information from and to write information to the pre-op database 302. The pre-op database 302 can include a procedure database 316, an inventory database 317, and a catalog database 318. Various ones of the pre-op module's component modules 218, 220, 222, 224 can be configured to access one or more of the procedure database 316, the inventory database 317, the catalog database 318, and/or various other databases, e.g., the diagnosis and treatment database 300, the operation database 304, the post-op database 306, and the recovery database 308. Each of the databases 316, 317, 318 is discussed further below in connection with various ones of the pre-op module's component modules 218, 220, 222, 224.

Surgical Procedure Planning Module

The surgical procedure planning (SPP) module 218 can provide users of the system 10 with an interface for electronically performing 3D simulated surgeries. In an exemplary embodiment, only surgeons authorized to perform surgery can access the SPP module 218. The procedure database 316 can be configured to store a record of a performed simulated surgery, e.g., a video of the simulated surgery, an inventory of surgical instruments used in the simulated surgery, statistics regarding the simulated surgery (e.g., a total length of surgery time, a length of a particular portion of the procedure, an amount and/or exact location of bone and/or soft tissue removed from the virtual patient, etc.), annotations or notes added by the user performing the simulated surgery, etc. The simulated surgery can therefore be used in the future for reference and/or analysis by the performer of the simulated surgery, by residents for training purposes, by staff involved with an actual surgical procedure corresponding to the simulated surgery, and/or by other users of the system 10, such as during and/or after performance of an actual surgical procedure corresponding to the simulated surgical procedure, as discussed further below regarding the operation module 204 and the post-op module 206.

The SPP module 218 can allow a user to select a surgical procedure to simulate. The user can simulate any number of surgical procedures, thereby allowing the user to experiment with procedures that the user may never have performed before or may only rarely perform. The procedure database 302 can include a collection of surgical procedures from which the user can select the surgical procedure. The procedure database 302 can include data related to each of surgical procedures in the collection, which can allow the SPP module 218 to provide suggestions and options to the user based on the user's selection of a particular surgical procedure. The SPP module 218 can be configured to recommend an optimized plan for the selected surgical procedure. In an exemplary embodiment, the optimized plan can be provided to the user before commencement of the simulated surgery and can be accessible by the user throughout performance of the simulated surgery. The SPP module 218 can be configured to develop the optimized plan based on a plurality of factors, e.g., data stored in the procedure database 316 (and/or in any other database) regarding previously performed actual surgical procedures and outcomes corresponding to the selected surgical procedure performed by the user and/or other users, data regarding the patient on which the simulated surgery will be actually performed, one or more goals identified by the user as being a surgical outcome goal, etc.

By way of non-limiting example, the SPP module 218 can be configured to provide a menu of surgical instruments to the user customized to the surgical procedure selected by the user (e.g., a menu including surgical instruments used in actual surgical procedures of a same type as the selected simulated procedure previously performed by the user and/or other users in the past), an estimated cost of the selected surgical procedure based on previously performed actual surgical procedures of a same type as the selected simulated procedure, one or more professional educational resources about the selected simulated surgical procedure (e.g., links to external websites; an estimated costs of the selected surgical procedure for each different equipment and/or staff selection made by the user; links to manuals, videos, images, and/or other informational data stored in the catalog database 318; and identification of colleagues of the user (e.g., surgeons working in the same hospital as the user) who have previously performed an actual surgical procedure of a same type as the selected simulated procedure and are available for consultation; etc.); identification of surgical support staff associated with the user (e.g., staff working in the same hospital as the user) who have assisted with an actual surgical procedure of a same type as the selected simulated procedure. Exemplary embodiments of providing educational support to users are described in more detail in U.S. patent application Ser. No. 13/603,452 entitled "Systems And Methods For Surgical Support And Management" filed Sep. 5, 2012.

The SPP module 218 can be configured to allow a user to save a selected list of surgical instruments, implants, and/or auxiliary equipment including hardware (e.g., monitors, scope, fluoro, etc.), and disposables (e.g., tubing, drapes, sensors, sharps, etc.) in the procedure database 316 that can be displayed to the user each time the user decides to perform a simulated surgery of a selected type or of any type. In some embodiments, a selected list of surgical instruments in the procedure database 316 can be saved for use by a plurality of users, e.g., users who all work at the same hospital, which can help ensure that only instruments actually available for use by surgeons at the hospital are selected for use in a simulation. Any lists saved in the procedure database 316 can be modified or deleted at any time.

The SPP module 218 can be configured to suggest one or more alternates s for one or more selections by the user for use in the selected surgical procedure. Using surgical instruments as an example, the suggested alternate(s) can be instrument(s) similar to the selected instrument as determined by previous correlations made between different surgical instruments, e.g., categorizing each surgical instrument by type, size, which actual surgical procedures the instrument was previously used in by the user and/or other users, etc. The suggested alternate(s) may be previously unused or unknown to the user. The user can thus be informed of newly available instruments, of instruments that may make the procedure easier to perform, and of instruments that may be less costly than the selected instrument. The inventory database 317 can store data (e.g., a table) regarding a plurality of actual surgical instruments available for use by the user in an actual surgery. The suggested one or more alternate surgical instruments can be based on the actual availability of instruments as indicated in the inventory database 317.

Figure 8:
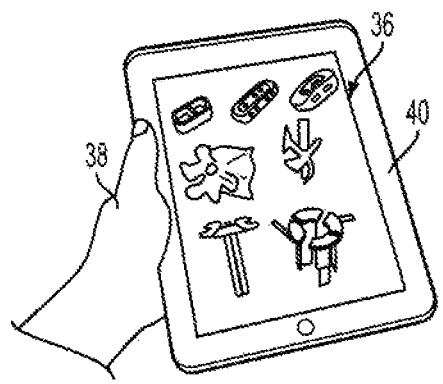
FIG. 8 is a perspective view of yet another embodiment of a client terminal that allows user input of data to the diagnosis, surgical planning, support, and management system of FIG. 2.

FIG. 8 illustrates an embodiment of a menu including surgical instruments and implants 36 used in actual surgical procedures of a same type as the selected simulated procedure that the SPP module 218 can display to a user 38. A client terminal on which the menu is displayed and on which the simulated procedure can be performed by the user 38 is shown in the illustrated embodiment as a tablet 40, but as mentioned above, any client terminal can be used to access the system 10. Each of the surgical instruments and implants 36 can be a 3D model of an actual surgical instrument available for use in an actual surgical procedure. Information about each of the instruments and implants 36 can be shown on the display and/or available by selecting one of the instruments and implants 36, e.g., by clicking on or hovering a selection tool over an instrument. The instrument information can be stored in the catalog database 318. Non-limiting examples of information about instruments, implants, and auxiliary equipment include cost, size, availability in the user's hospital inventory, manufacturer, indication as to whether the user previously used the instrument in a previous actual surgical procedure, and whether additional views of the instrument are available. Although the menu is shown in FIG. 8 as a pictorial menu, the menu can be presented in any way, such as all text, all pictorial, or a combination of text and images. Additionally, one or more informational resources, e.g., links to product brochures, links to educational videos of products in use, identification of previous surgical procedure(s) using the menu item that were performed by the user, etc., can be provided for any one or more of the menu items.

The SPP module 218 can be configured to model the patient on which the selected simulated surgical procedure is to be performed. In other words, the SPP module 218 can be configured to create a virtual patient modeled on an actual patient. The virtual patient can be based on data stored in the system 10 (such as data regarding the actual patient stored in the diagnosis and treatment database 300, e.g., patient weight, x-ray images, CT images, MRI images, ultrasound images, BMI, genetic test results, visual images of the patient, etc.) and/or based on typical patient data stored in the system 10. The simulated surgery can thus be performed on a model as close to the actual patient as possible, helping to allow the simulation to train the user as much as possible and helping to provide reliable outcomes of the surgery.

Figure 9:
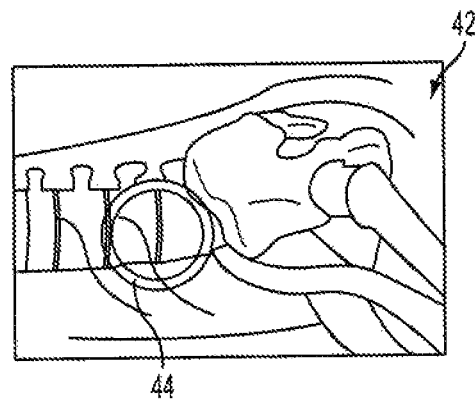
FIG. 9 is a perspective view of an embodiment of a simulated surgical procedure display provided by the diagnosis, surgical planning, support, and management system of FIG. 2.

FIG. 9 illustrates an embodiment of a simulated surgical procedure display 42. A vertebra is circled in the display 42 for ease of identification of a surgical target 44.

Figure 10:
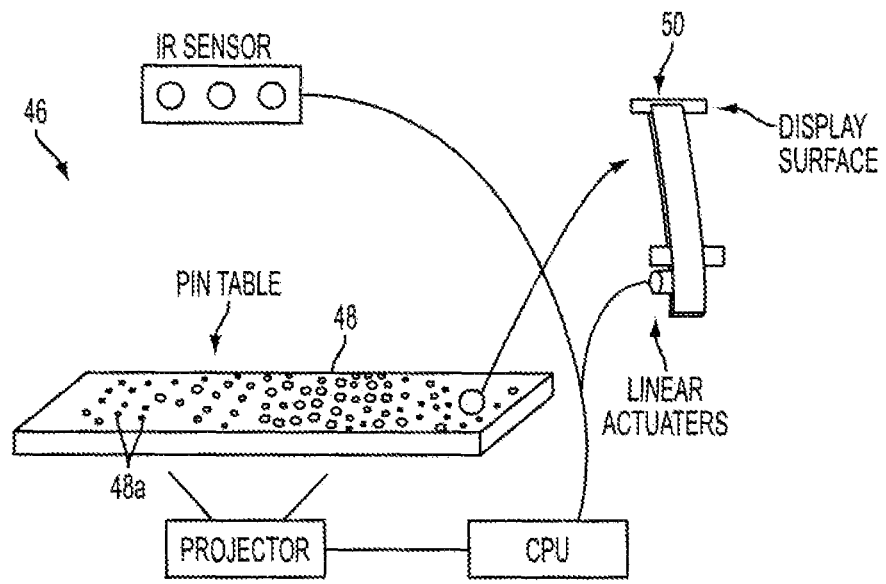
FIG. 10 is a perspective view of an embodiment of a topographical mapping system that provides topographical mapping information to the diagnosis, surgical planning, support, and management system of FIG. 2.

A simulated surgical procedure display can include one or more user options configured to provide enhanced visualization of the procedure. Non-limiting examples of such options include 3D (e.g., the user can choose 3D display and wear 3D glasses to properly see the 3D display), holograms, and topographical maps. FIG. 10 illustrates an embodiment of a topographical mapping system 46 including a pin table 48 configured to facilitate visualization of 3D data on a 2D display device 50. The pin table 48 can include a plurality of pins 48a each configured to automatically adjust in height to show 3D data based on the 3D model of the patient in the SPP module 218, thereby allowing, e.g., visualization of the deformity and correction. The pins 48a can be covered in a flexible sheet to enhance visualization of the preoperative, intra, and post operative 3D geometry.

The simulated surgery can allow the user to simulate the selected surgical procedure from beginning to end. Aspects of the selected surgical procedure that can be simulated can include one or more of an access point on the patient, surgical instruments used in the procedure, a path through and/or retraction of tissue and nervous structures, bone removal, soft tissue removal, tissue and structure movement, correction, movement due to indirect decompression, and placement of all implants. The user can save the simulated procedures at various points throughout the simulation, which can allow the user to repeat aspects of the procedure more than once to perfect technique, to test performance of different surgical products, to test the suitability of different access points, and/or to achieve other goals.

The SPP module 218 can be configured to analyze various aspects of the simulated surgical procedure in real time with performance of the simulation. For non-limiting example, the SPP module 218 can be configured to monitor an amount of radiation the patient, surgeon, and OR staff could be exposed to during the surgery and, optionally, tally a cumulative total radiation exposure for the patient including the simulated surgery and actual prior radiation exposure as well as future predicted exposures. Monitoring radiation exposure can help encourage reduction of the patient's radiation exposure and help ensure that the patient is not exposed to radiation beyond an acceptable level within a certain period of time. For non-limiting example, the SPP module 218 can be configured to compare drug use during the simulated procedure with known allergies of the patient and with known drug interactions, thereby helping to reduce chances of drugs adversely affecting the patient during or after surgery. For yet another non-limiting example, the SPP module 218 can be configured to perform predictive volumetric modeling of soft tissue movement, stretch, removal (e.g., of a herniated disc), and change based on each step of the simulated procedure. The user can thus be able to see in real time with the simulation how tissue and other structures will move based on each step of the procedure. During the simulated procedure, the SPP module 218 can be configured to use this predictive modeling to show where tissue and other structures are predicted to be, allowing for navigation around them. The SPP module simulation can utilize historical surgical and literature data to predict neural responses and/or changes based upon a predicted amount of retraction and/or decompression preformed. When the simulation is complete, the SPP module 218 can be configured to analyze the procedure for projected results, e.g., potential healing, potential increase in patient mobility after "X" amount of time, amount of correction, etc. The user can thus consult the projected results and decide whether to revise the surgery, such as if the projected results are less than the user would like and/or expect.

The SPP module 218 can facilitate the planning of revision surgeries. Using a spinal surgical procedure as an example, patient information regarding initial implant product, position, bony ingrowth or ongrowth, etc. can be reviewed prior to surgery. The approach to remove the initial implant, the optimal sizing of the replacement implant, and the need for additional instrumentation (e.g., instrument set of the initial product or bone removal tools) can be incorporated in the surgical plan for the implant revision.

When the user completes a simulated surgical procedure, the user can mark the procedure as being complete. Marking the simulation as being complete can signal to the SPP module 218 that pre-op planning by the system 10 for an actual surgical procedure corresponding to the simulated surgical procedure can begin. Throughout performance of the simulated surgical procedure, the SPP module 218 can allow the user to save progress of the simulation, but these saves can be marked as incomplete simulations in the procedure database 316. The user can choose to perform a simulation all at once, or the user can save a partially complete simulation and resume the saved simulation at a later date/time. A user can choose to never complete a partially finished simulation. The SPP module 218 can be configured to incorporate historical patient growth data to further depict structural changes over patient's lifetime. This incorporation can be especially helpful with patients having variable and changing anatomies, e.g., young scoliosis patients with variable and changing curvatures. Users of the system 10 can run a predicted life changes module to assess potential future changes and assist in planning and refining the surgical procedure.

Figure 11:
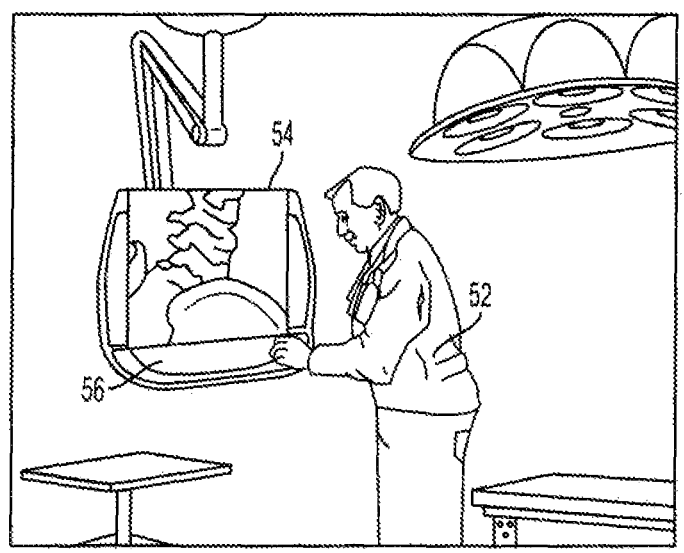
FIG. 11 is a perspective view of an embodiment of a client terminal in an OR setting that communicates with the diagnosis, surgical planning, support, and management system of FIG. 2.

The SPP module 218 can be available to users inside and outside the OR. In other words, a user can perform a simulation using the SPP module 218 outside the OR, e.g., before surgery is even scheduled, and/or inside the OR, e.g., as immediate prep before a scheduled surgery. FIG. 11 illustrates an embodiment of a user 52 accessing the system 10 in an OR via a client terminal in the form of a computer including a processor (not shown), a display screen 54, and a keyboard 56. In the illustrated embodiment, the user 52 is simulating performance of a spinal procedure, but as mentioned above, the system 10 can be used to simulate other types of surgical procedures.

Equipment Management Module

The equipment management module 220 can provide users of the system 10 with an interface for managing equipment used in surgery, such as surgical implants and surgical instruments. In an exemplary embodiment, only medical administrators (e.g., hospital inventory managers, etc.) and medical personnel (e.g., surgeons authorized to perform surgery, etc.) can access the equipment management module 220.

The equipment management module 220 can be configured to determine whether actual inventory as reflected in the inventory database 317 can meet the needs of actual surgery based on the completed simulated surgery (e.g., a simulation marked as complete). In alternative (e.g., if no simulated surgery has been performed) or in addition to basing the determination on the completed simulated surgery, the equipment management module 220 can be configured to determine whether actual inventory as reflected in the inventory database 317 can meet the needs of actual surgery based on typical requirements for the selected surgical procedure and/or on specific requirements input by a user for the surgical procedure, e.g., a surgeon's preference to use medical devices manufactured by a specific company. The equipment management module 220 can be configured to compare virtual surgical instruments used by a user in a completed simulated surgery with actual surgical instruments available for use by the user in an actual surgical procedure corresponding to the simulation. As mentioned above, the inventory database 317 can store data regarding a plurality of actual surgical instruments available for use in actual surgeries. The equipment management module 220 can determine whether each of the virtual surgical instruments used in the completed simulated surgery is available in actual inventory as indicated in the inventory database 317. The SPP module 218 can be configured to allow a user to indicate that one or more extra surgical instruments need to be available in an OR during performance of an actual surgical procedure corresponding to a simulated surgical procedure, e.g., an additional implantable screw, a plurality of additional sutures, etc. The equipment management module 220 can be configured to include these requested extra surgical instruments in its determination of available actual inventory.

The equipment management module 220 can be configured to reserve actual surgical instruments and actual auxiliary equipment in inventory for use in the actual surgical procedure by marking the actual surgical instruments corresponding to the used virtual surgical instruments, the actual auxiliary equipment corresponding to the used virtual auxiliary equipment, and the requested extra surgical instruments as "reserved" in the inventory database 317. Inventory available to the user, e.g., inventory of a hospital, can thus be kept up to date for upcoming surgeries performed by the user and by any other medical professionals working from the same inventory as the user.

The equipment management module 220 can be configured to order actual surgical instruments and auxiliary equipment (e.g., from a medical device distributor or a medical device company) for use in the actual surgical procedure if the actual surgical instruments or actual auxiliary equipment are not available in inventory as indicated by the inventory database 317. The equipment management module 220 can be configured to order custom implants (e.g., from a medical device company) that are manufactured for use with a specific patient. Any pre-configuration of surgical supplies such as surgical instruments (e.g., contouring of spinal rods in accordance with the pre-op plan) and graft material (e.g., volume and type of a specific graft material) can be ordered by the equipment management module 220. As will be appreciated by a person skilled in the art, custom implants can be designed and ordered in a variety of ways. For non-limiting example, methods and apparatuses for customizing an intervertebral implant including an initial step of obtaining a 3D anatomy are described in further detail in U.S. application Ser. No. 11/150,468 (published as U.S. Pat. Pub. No. 2006/0282020) entitled "Customizing An Intervertebral Implant" filed Jun. 13, 2005. Generally, pre-op 3D anatomy of a patient can be obtained in a variety of ways, e.g., using a CT scanning machine, and can be stored in the system 10, e.g., in the diagnosis database 310 as discussed further below. The 3D image(s), e.g., a plurality of images from different angles, can be subsequently evaluated at any time by a surgeon or other medical staff to determine an appropriate custom implant for the patient, which can then be ordered for availability during surgery.

The equipment management module 220 can also be configured to track the status of open orders for actual surgical instruments, for custom implants, and for pre-configuration. The equipment management module 220 can thus help ensure that instruments are available when needed for surgery and that surgery need not be rescheduled and/or delayed merely due to surgical tools being unavailable. Exemplary embodiments of ordering and managing inventory are described in more detail in U.S. patent application Ser. No. 13/603,452 entitled "Systems And Methods For Surgical Support And Management" filed Sep. 5, 2012.

Scheduling Module

The scheduling module 222 can provide users of the system 10 with an interface for managing personnel (e.g., surgical support staff, sales representatives, etc.) and hospital space used in relation to the surgery (e.g., an OR, a patient prep room, a patient hospital recovery room, etc.). In an exemplary embodiment, only medical administrators (e.g., hospital inventory managers, etc.) and medical personnel (e.g., surgeons authorized to perform surgery, etc.) can access the scheduling module 222.

The scheduling module 222 can be configured to determine whether available personnel and available hospital space as reflected in the inventory database 317 can meet the needs of actual surgery based on the completed simulated surgery (e.g., a simulation marked as complete). In alternative (e.g., if no simulated surgery has been performed) or in addition to basing the determination on the completed simulated surgery, the scheduling module 222 can be configured to determine whether actual inventory as reflected in the inventory database 317 can meet the needs of actual surgery based on typical requirements for the selected surgical procedure and/or on specific requirements input by a user for the surgical procedure, e.g., a surgeon's preference to work with specific support personnel. The scheduling module 222 can be configured to determine if available inventory has been autoclaved and sterile. The scheduling module 222 can determine whether each of the hospital rooms needed for the surgery (e.g., an OR, a prep room, a patient recovery room, etc.) are available in actual inventory as indicated in the inventory database 317, and/or the scheduling module 222 can determine whether each of the surgical staff members needed for the surgery (e.g., a sales representative, an anesthesiologist, etc.) are available in actual inventory as indicated in the inventory database 317. The SPP module 218 can be configured to allow a user to indicate specific hospital space and/or personnel preferences for performance of an actual surgical procedure. The scheduling module 222 can be configured to include these specific preferences in its determination of available actual inventory. The SPP module 218 can be configured to store a user's preferences so the user does not have to repeatedly enter the same preferences.

The scheduling module 222 can be configured to reserve one or more hospital spaces (e.g., rooms) for use in the actual surgical procedure by marking the hospital spaces as "reserved" for a specific date and time in the inventory database 317. Similarly, the scheduling module 222 can be configured to schedule one or more medical staff members to be present for the actual surgical procedure by marking the one or more medical staff member's schedule (e.g., in one or more electronic calendars accessible to the medical staff members) as being "reserved" for a specific date and time in the inventory database 317. Hospital space and personnel available to the user can thus be kept up to date for upcoming surgeries performed by the user and by any other medical professionals working from the same hospital space and/or personnel pool as the user.

Exemplary embodiments of scheduling personnel and hospital space are described in more detail in U.S. patent application Ser. No. 13/603,452 entitled "Systems And Methods For Surgical Support And Management" filed Sep. 5, 2012.

Patient Preparation Module

The patient preparation module 224 can provide users of the system 10 with an interface for preparing a patient for a scheduled surgical procedure. The patient preparation module 224 can prepare the patient through a continuum of at-home patient preparation to arrival at the OR for the surgical procedure. In this way, the patient preparation module 224 can help the patient prepare at home for the surgery so the patient is more likely to arrive at the hospital on time and with any necessary pre-surgery requirements met, and can help ensure that the patient is appropriately prepared for the surgery while at the hospital prior to the patient's arrival at the OR.

The patient preparation module 224 can be configured to provide at-home, pre-surgery patient preparation to a user, e.g., to a patient scheduled for surgery. In an exemplary embodiment, the patient preparation module 224 can be configured to provide at least one reminder to the user regarding any pre-surgery requirements, such as a start day and time for fasting, day(s) and time(s) to ingest particular medication(s), day and time to arrive at the hospital, any preoperative blood test which must be completed, bodily samples taken, etc. The reminder(s) can be provided to the user in any number of ways, as will be appreciated by a person skilled in the art, such as by email, phone call, a mobile device app, etc. The patient preparation module 224 can be configured to allow the user to select one or more modes of reminder delivery. In an exemplary embodiment, the system 10 can prompt the user to select one or more modes of reminder delivery when the user initially establishes an account with the system 10, such as by prompting the user to enter at least one of an email address, a home phone number, a mobile phone number, an instant message account, etc. to which the system 10 can provide reminders, notifications, alerts, etc. If the user used the system 10 during treatment, the user can receive surgery prep reminders in the same way the user received treatment reminders, e.g., alerts from the treatment compliance module 216. In this way, by the time the user is preparing for a scheduled surgery, use of the system 10 can be familiar to the user, which can help ease the stress of surgery and help ensure that the patient is appropriately informed and reminded of any necessary pre-surgery procedures to be undertaken by the patient when medical personnel may not necessarily be with the patient to provide guidance.

The patient preparation module 224 can be configured to provide pre-surgery patient support by monitoring a patient scheduled for surgery from when the patient arrives at the hospital to when the patient arrives at the OR for the surgery. In an exemplary embodiment, the patient preparation module 224 can be configured to monitor the patient. The patient can be monitored in a variety of ways, such as by a smart chip embedded in a bracelet, necklace, gown, ID tag, etc. that the patient can wear. The patient preparation module 224 can be configured to monitor the patient's vital signs, location in the hospital, and status. This monitored information can allow the patient preparation module 224 to, e.g., trigger preparation of a room for the patient (e.g., using the patient's current location to trigger preparation of a next room for the patient), to alert medical personnel if the patient requires immediate attention (e.g., due to change in vital signs), and to allow for scheduling and/or inventory adjustments in the inventory database 317 if the patient's surgery is determined to be delayed based on the patient's presence in a certain location a certain amount of time before a scheduled surgery start time. This monitored information can allow the patient preparation module 224 to perform an automated pre-op check to ensure that the surgery to be performed matches the planned surgery, e.g., surgery on the correct side or correct spinal level(s). The monitoring performed by the patient preparation module 224 can be continued intra-operatively as needed to record vital signs, and can be combined with a multitude of other monitors that are conventionally used in an OR. All of these outputs can be collected by the operation database 304 of the system 10 throughout the procedure in order to be added to the patient's record for inclusion in analysis.

Operation Module

The operation module 204 can generally provide users of the system 10 with an interface for enhancing performance of a surgical procedure in an OR (or other location) and for gathering data for future analysis. More particularly, the operation module 204 can allow surgeons to consult a 3D simulated surgery performed and saved via the pre-op module 202, which can help an actual surgical procedure efficiently and effectively achieve predetermined outcomes. The operation module 204 can provide feedback regarding performance of the actual surgical procedure versus the previous simulated surgical procedure during performance of the actual surgical procedure, which can allow for mid-course corrections and/or can help inform surgical staff of their surgical duties. The operation module 204 can also provide informational materials during performance of the surgical procedure, such as instrument use manuals or videos, which can help ensure that the surgical procedure is performed properly. The operation module 204 can also track various aspects of the surgical procedure, e.g., instrument use, personnel activity, patient radiation exposure without the patient having to wear a radiation monitoring device such as a dosimeter. patient vital signs, etc., which can allow for mid-course corrections, help inform surgical staff of their surgical duties, and/or facilitate post-op analysis of the surgical procedure by the post-op module 206, as discussed further below. The information tracked by the operation module 204 can also be used by the system 10, e.g., by the recovery module 208, to facilitate patient recovery and continued treatment post-surgery, as discussed further below. The information tracked by the operation module 204 can also be used by the system 10, e.g., by the diagnosis and treatment module 200 and/or the pre-op module 202, in recommending and/or planning future surgeries involving the patient and/or other patients in circumstances similar to the patient on which the surgical procedure was performed. In this way, the system 10 can become smarter over time in various ways, such as by analyzing and recommending effective treatments in view of historical surgical outcomes, by providing recommended surgical strategies in view of a particular surgeon's historical performance in certain types of surgeries and/or with certain types of surgical instruments, and/or by providing recommended surgical strategies in view of multiple different surgeons' historical performance in certain types of surgeries and/or with certain types of surgical instruments.

In one embodiment, the operation module 204 can be implemented using one or more web pages which are configured to receive user input and present information to a user. In an exemplary embodiment, medical practitioners can access at least a portion of the operation module 204 while patients cannot access the operation module 204 at all.

The operation module 204 can include a plan tracking module 226, a procedure analysis module 230, an education module 228, an equipment tracking module 232, an OR analysis module 234, and a personnel tracking module 236. Each of the modules 226, 228 230, 232, 234, 236 is discussed further below in turn.

As mentioned above, the operation module 204 can be configured to read information from and to write information to the operation database 304. The operation database 304 can include a products and procedures database 320, an OR database 322, an equipment database 324, and an ethnography database 326. Various ones of the operation module's component modules 226, 228 230, 232, 234, 236 can be configured to access one or more of the products and procedures database 320, the OR database 322, the equipment database 324, the ethnography database 326, and/or various other databases, e.g., the diagnosis and treatment database 300, the pre-op database 302, the post-op database 306, and the recovery database 308. Each of the databases 320, 322, 324, 326 is discussed further below in connection with various ones of the pre-op module's component modules 226, 228 230, 232, 234, 236.

Figure 12:
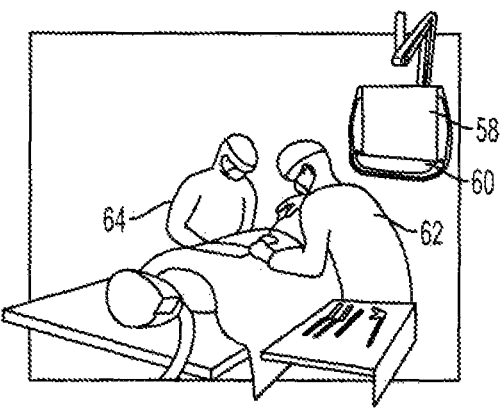
FIG. 12 is a perspective view of another embodiment of a client terminal in an OR setting that communicates with the diagnosis, surgical planning, support, and management system of FIG. 2.
Figure 13:
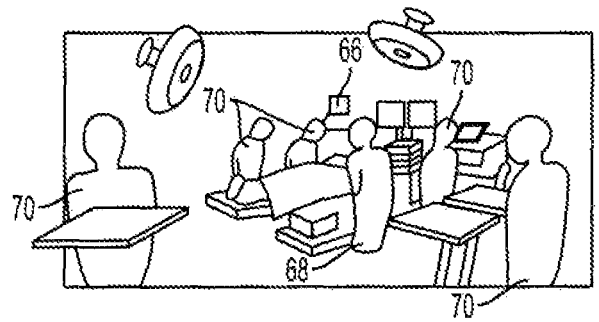
FIG. 13 is a perspective view of yet another embodiment of a client terminal in an OR setting that communicates with the diagnosis, surgical planning, support, and management system of FIG. 2.

In an exemplary embodiment, an OR has a single user interface configured to display information from the system 10 for consultation during a surgical procedure performed in the OR. The user interface can be located in the OR, or can be in a nearby area visible from the OR. FIG. 12 illustrates an embodiment of an OR setting in which the system 10 can be accessed via a client terminal in the form of a computer including a processor (not shown), a display screen 58, and a keyboard 60. In the illustrated embodiment, a surgeon 62 and medical support personnel 64 can all view the display screen 58, which can help all OR personnel track the procedure, be better informed of their duties, and help quickly notice any anomalies. FIG. 13 illustrates another embodiment of an OR setting in which the system 10 can be accessed via a client terminal in the form of a computer including a processor (not shown) and a display screen 66 located at a position easily seen from all or nearly all positions within the OR by a surgeon 68 and medical support personnel 70.

Various types of data gathered and/or analyzed by the system 10 can be displayed on a user interface and/or otherwise made available to medical personnel in the OR, such as by other visual indicator (e.g., by blinking light on a surgical instrument, etc.), motion (e.g., by vibration of a surgical instrument, etc.), or sound (e.g., by audio beep from a speaker in communication with the system 10, etc.). By providing non-auditory feedback alone or in combination with visual feedback, the feedback can be less likely to be lost or overlooked in a noisy OR environment.

Figure 14:
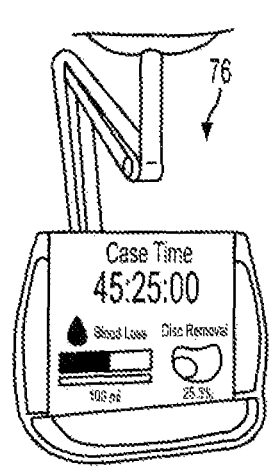
FIG. 14 is a perspective view of an embodiment of a client terminal showing surgical progress data received from the diagnosis, surgical planning, support, and management system of FIG. 2.
Figure 15:
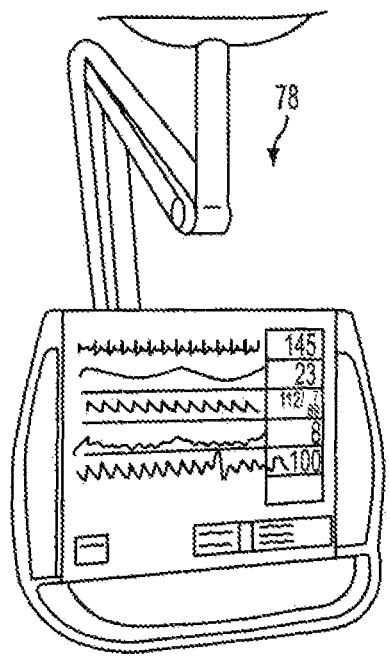
FIG. 15 is a perspective view of an embodiment of a client terminal showing patient data received from the diagnosis, surgical planning, support, and management system of FIG. 2.
Figure 16:
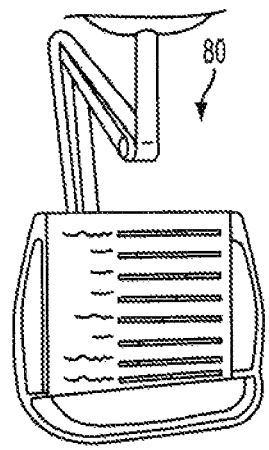
FIG. 16 is a perspective view of an embodiment of a client terminal showing surgical instrument data received from the diagnosis, surgical planning, support, and management system of FIG. 2.

FIGS. 14-16 illustrate embodiments of various types of data that can be selectively displayed on a user interface accessible in the OR. FIG. 14 illustrates a user interface 76 showing data indicating a progress of the surgery as gathered by the system 10 including a running total case time (e.g., a continually updated time length of the surgery), a total amount of patient blood loss, and a running total amount of spinal disc removal (e.g., a continually updated amount of spinal disc removed from the patient during the surgery). The progress data can help the surgery stay on schedule, help ensure safety of the patient (e.g., by considering whether the patient's blood loss reaches an unsafe level), and help the surgery meet its goals (e.g., by considering whether a desired amount of tissue is removed from the patient). Other, non-limiting examples of data indicating a progress of the surgery as gathered by the system 10 include an amount of bone removed from the patient, an amount of tissue and/or bone needed to be removed for graft (e.g., as indicated in a pre-op plan), endplate preparation (e.g., through endoscopic view and/or smart tools), implant placement (e.g., computer guided rod contouring in-situ), an amount of correction achieved, and pain/health of nerves. FIG. 15 illustrates a user interface 78 showing data indicating patient information, thereby helping to ensure patient safety. The patient information includes patient vital signs in the illustrated embodiment. Other, non-limiting examples of patient information that the system 10 can be configured to display in the OR include pre-op patient images (e.g., x-rays, CT scans, etc.). FIG. 16 illustrates a user interface 80 showing instrument information in the form of a list of instruments used in the surgical procedure and a running total amount of time each of the instruments has been used in the surgical procedure. Other, non-limiting examples of instrument information that the system 10 can be configured to display in the OR include camera views of one or more instruments, instrument navigation, and instrument specifications and/or manuals stored in the equipment database 324. The system 10 can be configured to display other types of information in the OR, such as education materials, as discussed further below with respect to the education module 228.

Although the illustrated embodiments of FIGS. 12 and 13 each include only one display for the system 10 in an OR, any number of displays for the system 10 can be provided in an OR. Providing a plurality of displays can allow more information to be easily accessible to medical personnel in the OR at any given time, can help focus medical personnel by allowing for different medical personnel to have dedicated displays providing information most useful for their particular job, and/or can reduce surgeon fatigue by allowing the surgeon to position themselves differently than if the displays were not available. Additionally, any one or more displays for the system 10 in the OR can be configured to display a plurality of views, e.g., have picture-in-picture capability (e.g., two different camera angles of the same surgical site) and/or provide overlays of data (e.g., overlaid tissue layers that can be peeled away one or more at a time to expose underlying layer(s)).

The system 10 can be configured to allow different data displays to be accessed on demand in the OR, e.g., a data display of a saved simulation plan and/or a comparison of a saved simulation with the actual procedure being performed, patient vital sign data, surgical procedure metrics, etc. In an exemplary embodiment, the system 10 can be configured to project digital keys (e.g., a keypad projected on or near the patient including keys) configured to be tapped to change display on the user interface and/or effect other system controls such as requesting that a specific medical staff member be paged to the OR, requesting an instrument from an instrument tray, rewind a simulation shown on a display, etc.

Figure 17A:
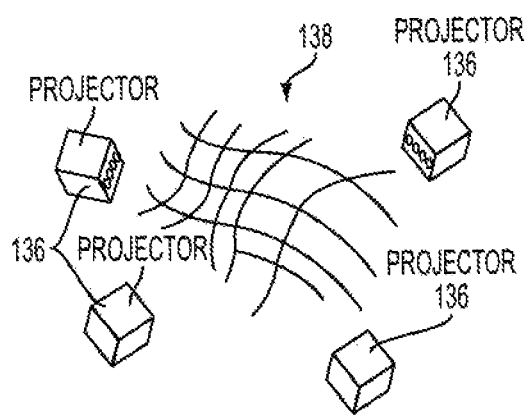
FIG. 17A is a perspective view of an embodiment of projection system that communicates with the diagnosis, surgical planning, support, and management system of FIG. 2.
Figure 17B:
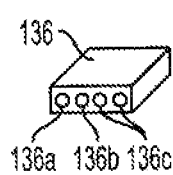
FIG. 17B is a perspective view of one of the projectors of the projection system of FIG. 17A.

FIG. 17A illustrates an embodiment of a projection system configured to facilitate projection onto an irregular screen surface such as on a patient in the OR or on another irregular surface such as an instrument tray or a drape. The projection system can include a plurality of projectors 136 configured to project an image onto an irregular screen surface 138. Each of the projectors 136 can be configured to be in communication with a CPU (not shown) of the system 10 so as to be configured to transmit information to and receive information from the CPU. The CPU can be in communication with at least one cloud server of the system 10 such that the CPU and/or a processor in communication with the cloud server(s) can perform data processing. Other CPUs discussed herein can be similarly configured to communicate with cloud server(s). Each of the projectors 136 in the illustrated embodiment is identical to one another, although projectors in the system can vary from one another. FIG. 17B illustrates one of the projectors 136 in closer detail. The projector 136 can include an RGB projector 136a configured to project RGB images, an IR sensor 136b configured to sense infrared signals, and an IR projector (dot and rectangle) 136c configured to project infrared images. Using IR can allow the projectors 136 to constantly align with one another and track the surface 138, which can allow for constant updating and good quality projection. Single viewer perspective tracking the surface 138 can allow for sub-surface projection allusions. The dot projection of the IR projector 136c can be used for surface mapping, and the rectangle projection of the IR projector 136c can be used for multi-projection overlap seaming. All of the projectors 136 can be synchronized to be in rectangle projection mode at once and then each take a turn in dot mode for surface mapping. The CPU can be configured to control the rectangle and dot modes of the projectors 136.

In another exemplary embodiment, the system 10 can be configured to allow selective switching between the different displays via no-touch controls. In this way, medical personnel can quickly receive data without compromising sterility and without having to change their position relative to the patient and without having to free their hands from instrument(s) and/or other surgical duties. No-touch controls can be similarly used for other system instructions, e.g., begin projection of digital keyboard, requesting that a specific medical staff member be paged to the OR, requesting an instrument from an instrument tray, rewind a simulation shown on a display, etc. Non-limiting examples of no-touch controls include motion sensing (e.g., swiping a hand in the air mimicking a page turn to cause a next display screen to be displayed on the user interface as if turning a page in a book), eye movement tracking (e.g. looking at a specific location or combination of locations in the spatial field either alone), voice recognition (e.g., speaking a certain key term or key phrase to cause a certain display to be shown on the user interface), and direct brain interface (e.g., via electroencephalography (EEG) sensors and event related potential ERP techniques including but not limited to use of P300, slow cortical response, and neural network based training methods). No-touch controls can also be used in any combination, e.g., looking at a specific location in a spatial field room and speaking a specific activation word. A specific activating location in the visual field can be dynamic and part of a computer controlled display device.

Figure 18:
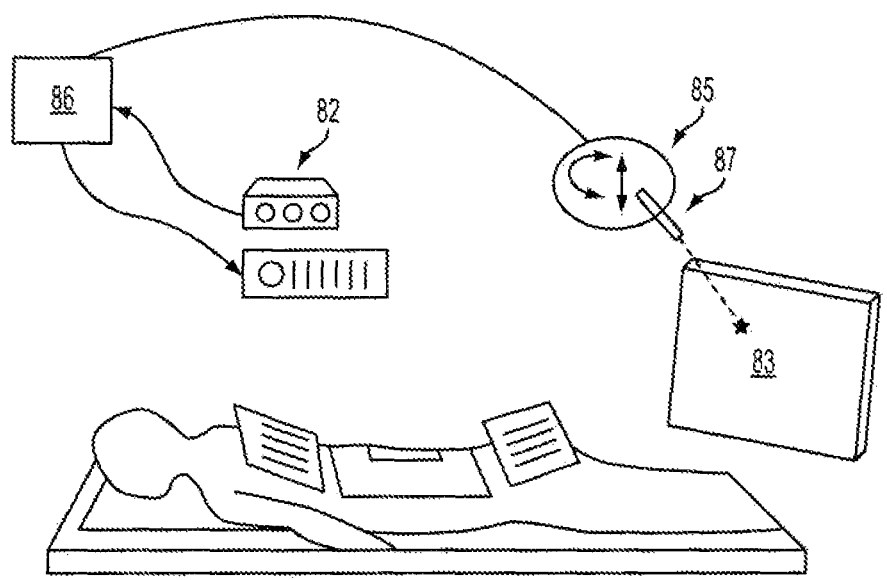
FIG. 18 is a perspective view of an embodiment of a motion sensing system that communicates with the diagnosis, surgical planning, support, and management system of FIG. 2.

FIG. 18 illustrates an embodiment of a motion sensing system configured to allow no-touch control of the system 10. The motion sensing system can include a projector 82 and an infrared (IR) and RGB camera 84 configured to gather data related to movement of a person in the OR. The gathered data can be transmitted to a central processing unit (CPU) 86 that is part of the system 10, the CPU 86 being configured to analyze the received data to determine if display on a user interface, such as a data board 83, should change. The data board 83 can include a flat surface that can be tracked for position by the camera 84, and can have selected images displayed on the surface thereof. The user can touch the projection on the data board 83 of a virtual input device, such as a button, to which the system can respond as having read the user's finger motion, position, and projected image as a command. The no-touch controls can facilitate communication of orders from a surgeon to OR staff. In the illustrated embodiment, the CPU 86 can be coupled to a laser pointer 87 configured to communicate orders to OR staff by directing OR staff to a specific needed instrument from among a plurality of instruments on a tray 89 by laser pointing to the needed instrument. The laser pointer 87 can be coupled to a movement mechanism, e.g., a rotation mount 85, configured to move in response to instructions received from the CPU 86, e.g., instructions to rotate a certain amount in a certain direction to cause the laser pointer 87 to point to the needed instrument on the tray 89. The laser pointer 87 can include a camera (not shown) configured to provide visual confirmation on the user interface that the laser pointer 87 has pointed to the needed instrument, which can allow the user providing the instruction to visually confirm the instruction.

Figure 19:
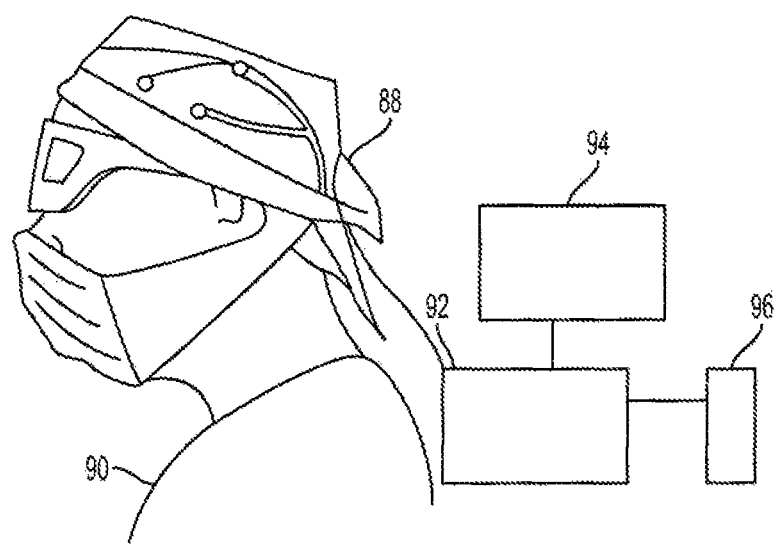
FIG. 19 is a perspective view of an embodiment of a direct brain interface system that communicates with the diagnosis, surgical planning, support, and management system of FIG. 2.

FIG. 19 illustrates an embodiment of a direct brain interface system, such as the EPOC Neuroheadset (available from Emotiv Systems of San Francisco, CA), configured to allow no-touch control of the system 10. The direct brain interface system can include a plurality of EEG sensors 88 configured to be position on a head of a user 90, e.g., a surgeon. The EEG sensors 88 can be configured to transmit data to a CPU 92 that is part of the system 10, the CPU 92 being configured to analyze the received data to determine if display on a user interface 94 should change. Additionally or alternatively, the CPU 92 can be configured to analyze the received data to determine if one or more pieces of OR equipment 96 (e.g., surgical tools, lights, tables, etc.) need adjustment and, if so, to cause such adjustment to occur (e.g., dim a light, turn on a light, zoom in a camera, adjust table height, etc.). OR equipment can be connected to the direct brain interface system by a programmable processor, such as an Arduino.

Figure 20:
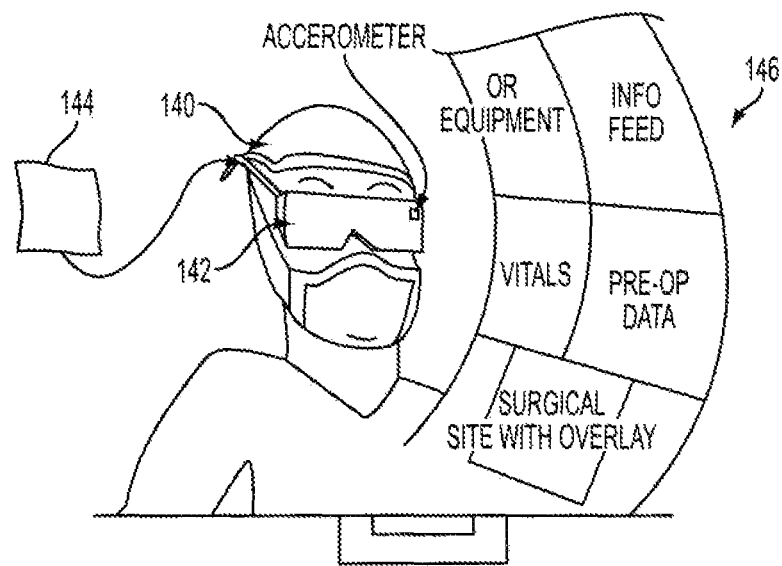
FIG. 20 is a perspective view of an embodiment of a no-touch data communication system that communicates with the diagnosis, surgical planning, support, and management system of FIG. 2.

FIG. 20 illustrates an embodiment of a no-touch data communication system configured to provide information hands-free to a user 140 of the system 10. The no-touch data communication system can be configured to allow the user 140 to control receipt of information from the system 10 through movement. In other words, the system 10 can transmit different information to the user 140 based on the movement of the user 140. Additionally, the no-touch data communication system can be configured for single-person use so as to allow the selected information to be transmitted uniquely to the user 140 such that one or more other users of the system 10 in the OR can have their own no-touch data communication system, which can allow each user to select the information that would be most helpful for their particular task at hand. The no-touch data communication system can, however, be configured to transmit the same information to a plurality of users based on movement control of the one user 140. The no-touch data communication system can include a transparent lens head mounted display 142 configured to be mounted on a head of the user 140. The transparent lens head mounted display 142 can be equipped with orientation tracking such that when the transparent lens head mounted display 142 is mounted on the head of the user 140, the user's head movements can control which information is displayed to the user 140. The transparent lens head mounted display 142 can be configured to communicate with a CPU 144 of the system 10, thereby allowing the information displayed by the transparent lens head mounted display 142 to be up to date in real time. In an exemplary embodiment, the motion of the user's head, e.g., turning and/or raising of the head, can allow the user 140 to see different data in different spherical zones 146. Each of the spherical zones 146 can display a different type of data, e.g., information regarding OR equipment, pre-op data, patient vital signs, informational feed regarding surgical steps, visualization of the surgical site with tissue layer(s) overlay, etc. In another embodiment, the motion of the user's head, e.g., turning and/or raising of the head, can cause the CPU 144 to cause projection of different data onto the patient and/or other surface.

Plan Tracking Module

The plan tracking module 226 can provide users of the system 10 with an interface for tracking progress of an actual surgical procedure in a surgical setting, e.g., in an OR. The progress of an actual surgical procedure can be tracked against a typical performance of the surgical procedure stored in the products and procedures database 320 and/or tracked against a 3D simulated surgery performed via the pre-op module 202 and saved in the procedure database 316. The typical performance of the surgical procedure can be pre-programmed, e.g., a saved demonstration version of the surgical procedure performed under laboratory or test conditions, or the typical performance of the surgical procedure can be aggregated from previous actual performances of the surgical procedure tracked by the system 10 and stored in the products and procedures database 320. The previous actual performances of the surgical procedure can be by a specific surgeon (e.g., the surgeon performing the actual surgical procedure), by surgeons at a specific hospital (e.g., the same hospital as where the actual surgical procedure is being performed), or by surgeons at multiple hospitals registered with the system 10. In an exemplary embodiment, the progress of an actual surgical procedure can be tracked against a 3D simulated surgery performed via the pre-op module 202 and can be saved in the procedure database 316 to allow the surgeon performing the procedure to follow previously-made decisions regarding the surgery, e.g., timing of the procedure's steps, medical devices used in the procedure, amount of patient tissue to remove, etc., since, as discussed above, the surgeon performing the actual surgical procedure can electronically simulate the surgery using the system 10. The system 10 can allow a user to pull up a simulation saved in the procedure database 316, thereby allowing the simulation to be visible and/or accessible in an OR.

The plan tracking module 226 can be configured to assist with surgical setup of a patient and one or more instruments to be used in surgery on the patient. The plan tracking module 226 can be configured to facilitate positioning of a patient for surgery. Because a patient's inner anatomy does not always align with spatial references of an operating room (or other area in which surgery is performed), and usually does not so align, it can be difficult for surgical staff to align the patient in a desirable position relative to the surgeon for performance of a specific surgical procedure. Numerous angles and asymmetries of the patient's inner anatomy, which differ between different patients, can result in lengthy pre-surgery evaluation of a specific patient's inner anatomy using techniques such as x-ray, fluoroscopy C-arm, and MRI, lengthy pre-surgery planning for the patient's position during surgery based on the evaluation, and lengthy manual positioning of the patient in the operating room (or other surgical area) based on the pre-surgery plan. Hidden anatomical structures, such as spinal elements, cannot be easily seen in an orthogonal sense as there are no cornerstones to align or columns to true. Repeated x-rays, and hence repeated radiation exposure, and/or invasive dissections are often traditionally needed to establish a frame of reference for a surgical task to use as its substructure during surgery. Traditional alignment using a gravity vector reference using robotics and image guidance are expensive, time consuming, and require steep learning curves and/or specialized user operators. Additionally, although apparatuses exist that can be used by surgical staff to assist in positioning a patient, these apparatuses are traditionally complicated and require a high level of user involvement. The plan tracking module 226 can be configured to automate patient positioning, which can reduce complexity of patient processing, reduce chances of surgical instruments being advanced into a patient at an unsafe and/or undesired trajectory, improve access to a surgical site by optimizing a patient's position, save time over manual patient adjustment, and/or reduce an amount of pre-surgery radiation and/or invasive pre-surgery dissections to determine proper patient positioning. Positioning the patient using the plan tracking module 226 can thus provide enhanced safety, enhanced ergonomics, and unfettered patient positioning with enhanced patient comfort, pressure relief, and surgical staff ease of use.

Figure 29A:
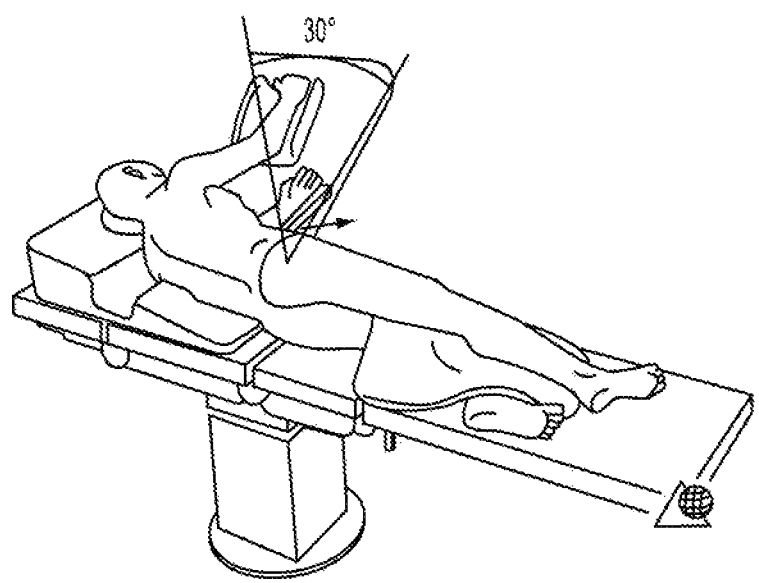
FIG. 29A is a perspective view of an embodiment of a patient on a bed in a surgical setting.
Figure 29B:
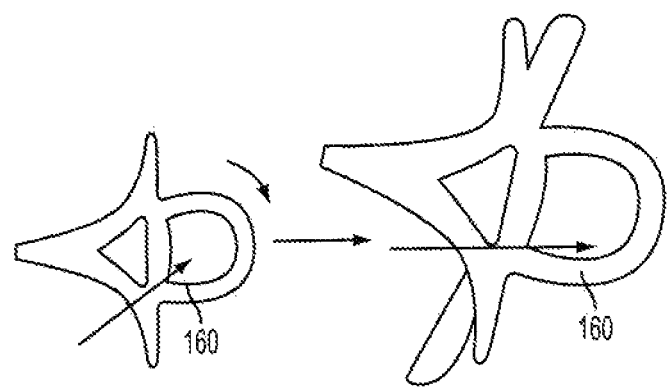
FIG. 29B is a series of perspective views of an embodiment of a pedicle demonstrating vertebral body translation which converts a pedicle trajectory from a first position to a second horizontal or plumb position.

For some surgical procedures, such as spinal surgeries in which a trajectory of lateral approach can be very precisely determined so as to access a target vertebra while avoiding nerve damage, a patient's position can be of particular importance to the surgery's duration and ultimate success. During lateral interbody surgery, for non-limiting example, it can be advantageous to align a representative plane of a superior endplate of a patient's inferior vertebra to vertical plumb, and it can be advantageous to align a mid frontal plane of the patient's interbody space to vertical plumb. In other words, it can be advantageous to position a center of the patient's vertebral disc, as well as endplates of the vertebrae, straight down from a perspective of a surgeon performing the surgery. Implantation of one or more percutaneous screws while a patient remains in a lateral position is a non-limiting example of a spinal surgical procedure in which precise patient positioning is important. Lining up a patient's pedicle 160 for direct horizontal pedicle screw placement can be at about a 30° rotation, as shown in FIGS. 29A and 29B. FIG. 29B shows the pedicle 160 in an initial position, e.g., at 30°, on the left, and in a rotated position, e.g., at 0° (horizontal), on the right.

The plan tracking module 226 can be configured to match the patient's position with a pre-surgery plan, e.g., a plan indicated in a saved simulated surgery or a plan for a typical procedure of a same type as the surgery being performed. The matching can be achieved in a variety of ways, such as through patient mapping/registration and/or through video tutorials. In an exemplary embodiment, the plan tracking module 226 can be configured to begin patient positioning assistance with a video tutorial saved in the products and procedures database 320. The patient positioning assistance can continue using positioning/navigation technology, e.g., Microsoft Kinect, that can track actual position of the patient versus the pre-surgery plan. As the patient is moved, the plan tracking module 226 can be configured to compare the patient's actual position to images of the patient and to the pre-surgery plan and can be configured to provide feedback on how to move the patient to the proper position as defined in the pre-op plan. The images of the patient can include previously gathered images, e.g., fluoroscopy, MRI, or CT images stored in the diagnosis database 310, and/or images gathered in real-time with the positioning, e.g., skin surface mapping, fluoroscopy, ultrasound, or intraoperative CT images. The patient can be imaged throughout the procedure in real time to help ensure that the patient is properly positioned during the procedure. Because the system 10 can help the patient be properly positioned according to surgeon instructions as indicated in the saved simulation, the surgeon need not necessarily be present in the OR when the patient is positioned by one or more medical personnel. The positioning time can be tracked by the plan tracking module 226 and can be recorded by the product and procedures database 320, which can help show improvements in efficiency over time and/or after additional training of OR staff.

Figure 21:
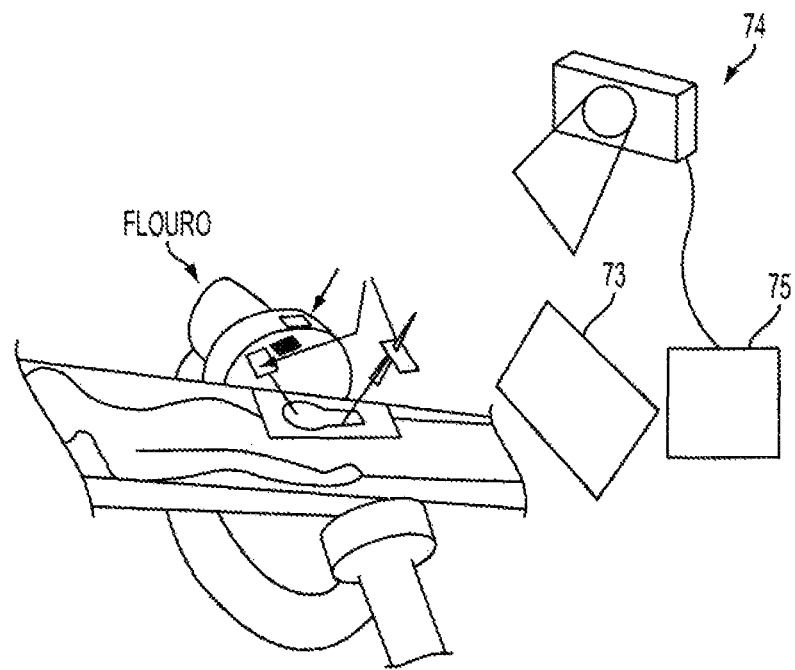
FIG. 21 is a perspective view of an embodiment of a visual position and orientation tracking system that communicates with the diagnosis, surgical planning, support, and management system of FIG. 2.

FIG. 21 illustrates an embodiment of a visual position and orientation tracking system configured to gather real time images of a patient in an OR. The illustrated system includes a fluoroscopy system, but as will be appreciated by a person skilled in the art, other visual position and orientation tracking systems can be used. The system can include one or more augmented reality markers 72 configured to be recognized by an RGB (red, green, and blue) or RGB-D (red, green, and blue plus depth) camera 74. The marker(s) 72 can be positioned on and/or near the patient to track position of the patient and fluoroscopy frame. The camera 74 can be configured to communicate with a CPU 75 of the system 10, which can cause image(s) gathered by the camera 74 to be displayed on a display 73.

The plan tracking module 226 can be configured to continually provide feedback to the one or more medical personnel positioning the patient, such as instruction as to how much to move a patient in a certain direction and an indication when the patient is in a position matching the pre-surgery plan, which can help ensure that the patient is properly positioned in the OR prior to start of the surgery. Because the system 10 can allow electronic tracking and positioning of patients, numerous different patient positions can be accommodated, such as more traditional recumbent positions and less traditional standing positions.

Figure 30:
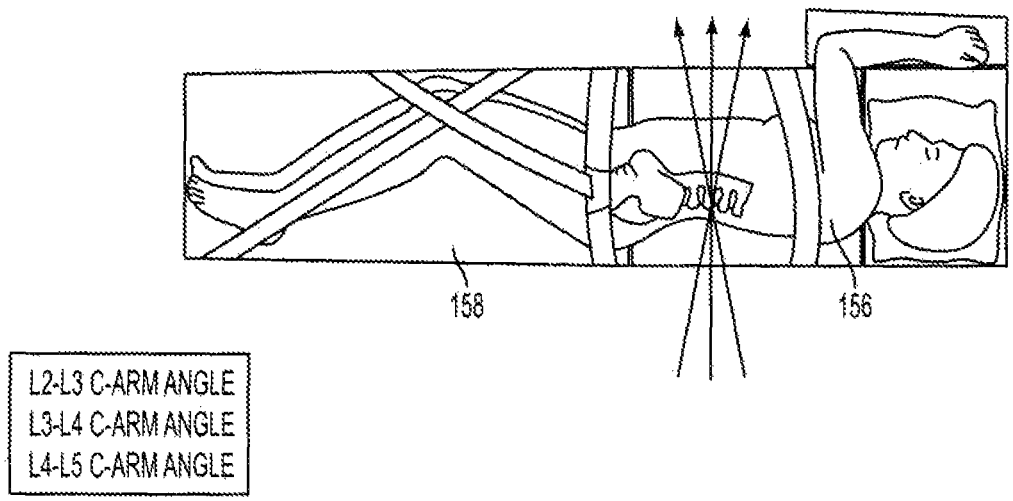
FIG. 30 is a top, partially transparent view of an embodiment of a patient on a bed in a surgical setting with desired vertebral angles.

In another exemplary embodiment, the plan tracking module 226 can be configured to facilitate patient positioning using automated bed movement. A person skilled in the art will appreciate that movement of a "bed" discussed herein includes movement of any operating surface on which a patient can be positioned for surgery, such as a table, a platform, etc., and is not necessarily a traditional bed. The plan tracking module 226 can be configured to cause translation and/or rotation of the bed, with the patient thereon, to position the patient in a desired position for surgery. FIG. 30 illustrates an embodiment of a patient 156 on a bed 158 at desired L2-L3, L3-L4, and L4-L5 angles, shown with arrows, as positioned using the plan tracking module 226. As shown, the bed 158 can include a plurality of discrete sections each configured to move relative to the other discrete sections, which can allow for more precise positioning of various portions of the patient 156 on the bed 158.

The plan tracking module 226 can be configured to cause the bed translation and/or rotation in a variety of ways. In an exemplary embodiment, X-Y-Z axis data for the bed can be transmitted to the system 10, and the plan tracking module 226 can be configured to use the received X-Y-Z data to determine an amount and direction of movement for the bed to position the patient thereon in a desired position for surgery. The X-Y-Z axis data for the bed can be gathered in a variety of ways. For non-limiting example, a plurality of two-dimensional (2D) and/or 3D images can be gathered using one or more types of imaging, e.g., imaging capable of rendering spatial coordinates such as radiograph, ultrasound, commuted tomography, magnetic resonance, etc., using one or more electromagnetic capture devices. The plan tracking module 226 can be configured to process the 2D images and/or the 3D images to derive X-Y-Z movement commands for bed positioning. The plan tracking module 226 can be configured to process the images in a variety of ways, such as by establishing a relation between the image data and coordinates of the bed. The relation can be established in any number of ways, as will be appreciated by a person skilled in the art, such as by using a calibration frame positioned within the imaging area combined with real time measurements of the frame's orientation to a known coordinate on the bed's frame and image capture device frame. Additionally, the plan tracking module 226 can be configured to compare image capture data to previously received data such as a known CT data set.

A majority of desired coordinates are vector quantities. The vector quantities, such as planar endplate orientations, midpoints, and trajectory angles, are independent of scalar calibration. Thus, the plan tracking module 226 can be configured to accurately process coordinate data without accurate unit values within the image frames of reference because angles (vectors) do not change based on scale.

As will be appreciated by a person skilled in the art, the plan tracking module 226 can determine how to repeatedly and accurately spatially position the bed in a variety of ways, such as by using motion control processing or software. For non-limiting example, for a spinal surgery using a trajectory of lateral approach that begins on the L3/L4 spinal level, the surgeon and/or other surgical staff can input this level to the plan tracking module 226, e.g., using an input device such as a keyboard in communication with a processor in communication with the plan tracking module 226. The plan tracking module 226 can then analyze an initial image of the patient and initial bed coordinates to cause the bed to be moved so as to position the patient in a desired position for the surgeon to begin the procedure on the L3/L4 spinal level. Then, if the surgeon desired to move to another area of the patient, such as the L4/L5 level, an updated input can reposition the patient in position for the surgeon to begin the procedure on the L4/L5 spinal level, as patient position is different for different lateral approaches. The updated input can be input to the plan tracking module 226 after the patient has been positioned in the first position, which can allow for the surgeon to make in-surgery decisions as appropriate, or the updated input can be input at the same time as the first input, which can help save time after the patient has been partially operated on and is more vulnerable to surgical complications than prior to being incised. Additionally, in surgery using a lateral approach, it can be advantageous to back up laterally-performed surgery with posterior instrumentation. If two sets of implants are to be implanted in the patient, a surgeon and/or other surgical staff traditionally must remove the patient from the lateral position in which the lateral surgery was performed and reposition the patient in a prone position in which the posterior surgery can be performed. Physically repositioning the patient mid-surgery in this way can be time consuming and can be awkward for surgical staff due to surgical instrumentation, surgical accessories, etc. on or in the patient during the repositioning. The plan tracking module 226 can allow for the patient to be automatically repositioned from the lateral position to a modified lateral position where posterior instrumentation trajectories are of a direct horizontal nature, or conversely to a modified prone position where desired trajectories are plumb, thereby saving time and reducing complexity of the surgical procedure. The plan tracking module 226 can thus be configured to move the patient to an initial position for surgery and to move the patient to one or more subsequent positions during the surgery, thereby allowing for different aspects of the surgical procedure to be performed on the patient at different angles that are each safe, appropriate, and convenient for the performing surgeon.

The plan tracking module 226 can be pre-programmed with a desired patient position for one or more specific surgical procedures, e.g., spine procedures such as anterior lumbar interbody fusion (ALIF), extreme lateral interbody fusion (XLIF), etc. The plan tracking module 226 can thus be programmed to "know" a desired position for a patient when a specific surgical procedure is input to the system 10 by a user as being for the patient. The plan tracking module 226 can thus be configured to automatically position the patient in the pre-programmed desired patient position using real time images of the patient indicating a current position of the patient, which the plan tracking module 226 can analyze in spatial coordinates relative to the desired patient position to determine an amount of translational and/or rotational movement of the bed to desirably position the patient.

Figure 31:
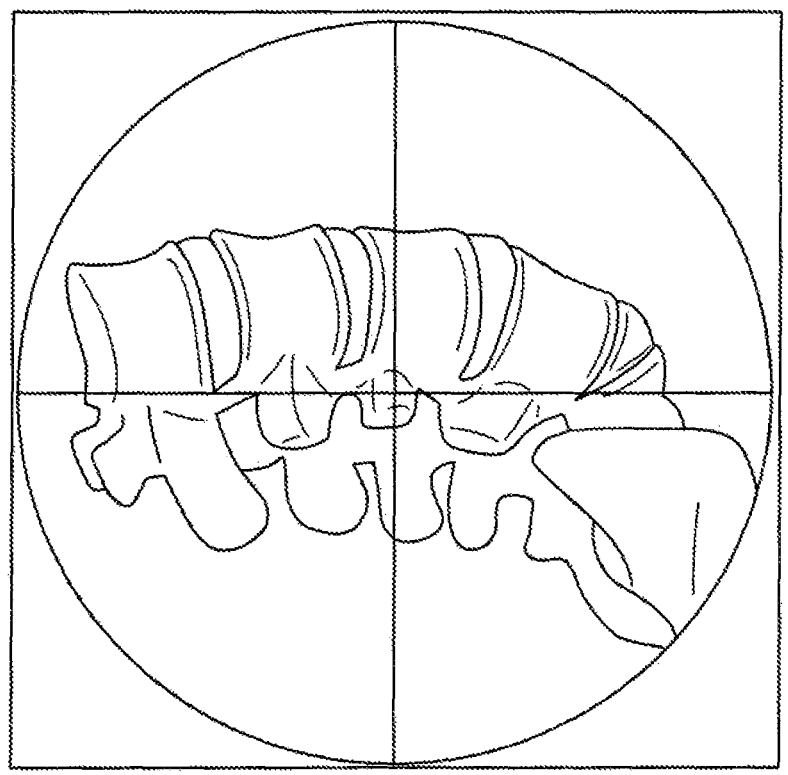
FIG. 31 is a perspective view of an embodiment of a fluoroscopic image of a lumbar spine of a patient in a baseline position.
Figure 32:
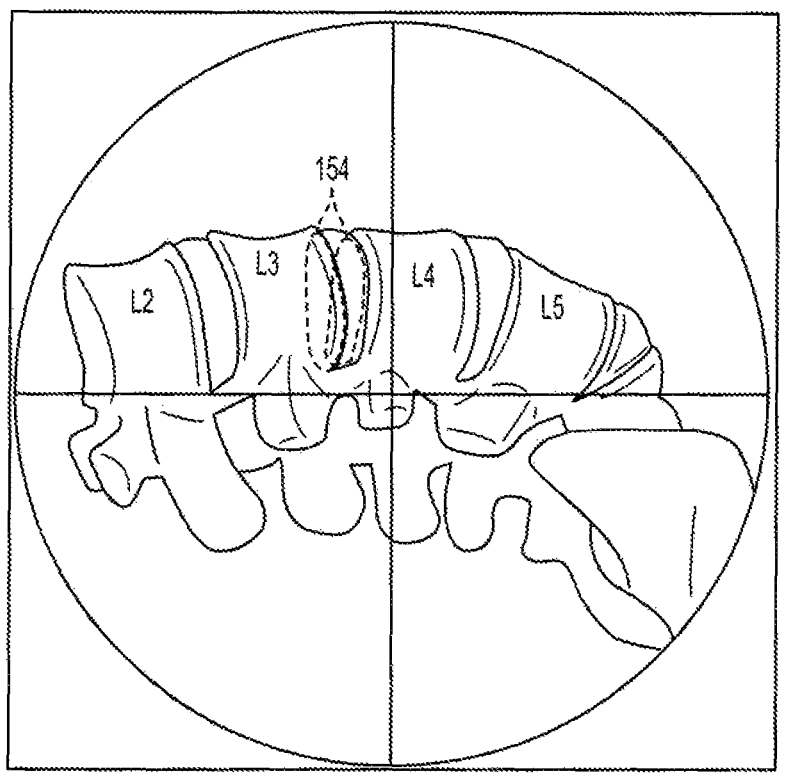
FIG. 32 is a perspective view of an embodiment of a fluoroscopic image of the lumbar spine of the patient of FIG. 31, the lumbar spine being in an initial surgical position.
Figure 33:
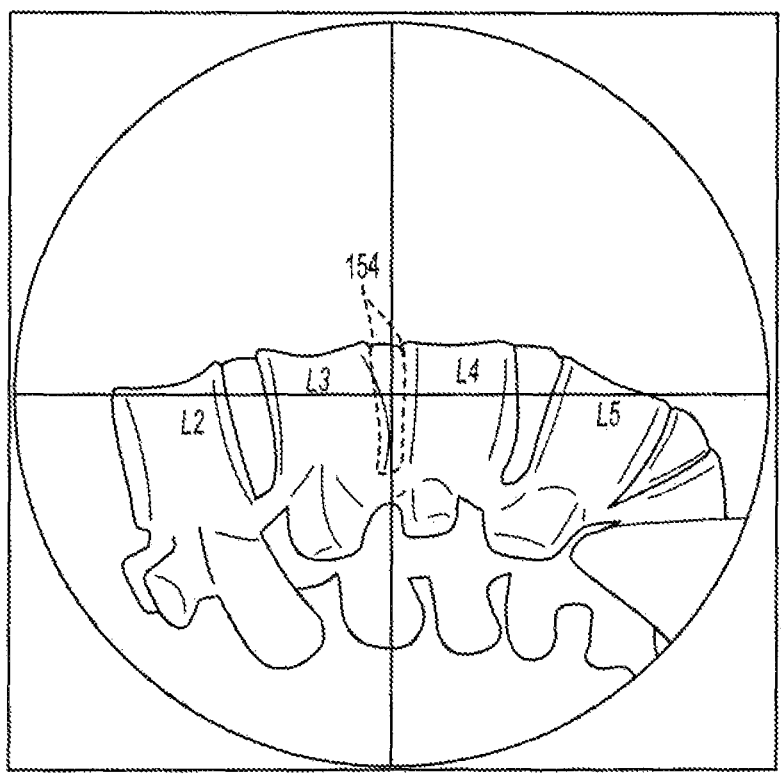
FIG. 33 is a perspective view of an embodiment of a fluoroscopic image of the lumbar spine of the patient of FIG. 32, the lumbar spine moved from the initial surgical position to an adjusted surgical position.

FIGS. 31-33 illustrate an embodiment of pre-surgery images that can facilitate automatic patient positioning using the plan tracking module 226. The images of FIGS. 31-33 are fluoroscopy images, but as discussed above, other types of images can be obtained to assist with patient positioning in the OR (or other surgical area). Fluoroscopic images can be gathered in real time in an OR using a C-arm, as will be appreciated by a person skilled in the art. Although the images of FIGS. 31-33 are spinal images that can assist in automatic positioning a patient for spinal surgery, the plan tracking module 226 can be configured to analyze images and automatically position a patient for surgeries on other parts of the body.

FIG. 31 illustrates an embodiment of a baseline image as a fluoro image of a patient's lumbar spine without an attempt to align the patient on a bed in any particular position relative to an operative center. In other words, the surgical staff can initially position the patient on the bed in a generally lateral position without careful precision as to the patient's position because the patient's position will be subsequently, automatically adjusted, unless the unlikely situation occurs where the patient is accurately initially positioned. The baseline image can facilitate anatomical recognition by the plan tracking module 226, as discussed further below. FIG. 32 illustrates an embodiment of a fluoro image including anatomical recognition performed by the plan tracking module 226 for a first input position. The anatomical recognition in FIG. 32 includes vertebral levels, e.g., L2, L3, etc., and endplate perimeter geometry 154. The endplate perimeter geometry is shown in FIG. 32 at the L3/L4 level to reflect an initial level for surgery input to the plan tracking module 226 as being the L3/L4 level. The plan tracking module 226 can also be configured to identify high crest for any of the vertebral levels. The plan tracking module 226 can perform the anatomical recognition in a variety of ways. For non-limiting example, the plan tracking module 226 can compare the baseline image of FIG. 30 with pre-stored anatomical data stored in the operation database 304 (and/or any other database). The pre-stored anatomical data can be data for a generic patient, e.g., anatomical textbook data, or can be actual anatomical data aggregated from a plurality of previously gathered images of actual patients. The plan tracking module 226 can be configured to filter the baseline image to create outlines, which can facilitate comparison of the baseline image with the pre-stored anatomical data to determine features in the baseline image, e.g., an endplate, a pedicle, etc. For non-limiting example, algorithms to perform such analysis include image guided surgery calibration algorithms, such as those discussed in U.S. Pat. No. 7,130,676 entitled "Fluoroscopic Image Guided Orthopaedic Surgery System With Intraoperative Registration" issued Oct. 31, 2006, and European Pat. No. 1028659 entitled "Virtual Representation Of A Bone Or Bone Joint" issued Feb. 18, 2004. Based on the pre-stored data in which various anatomical parts, e.g., levels of vertebra, are pre-identified, the plan tracking module 226 can be configured to identify various anatomical parts in the first input position. FIG. 33 illustrates an embodiment of a fluoro image post-positioning, e.g., with the patient having been automatically moved to the initial position, e.g., the bed has been translated and/or rotated as discussed above. In the illustrated embodiment, the bed has been moved to position the patient slightly anterior of the disc center at L3/L4. The post-positioning fluoro image can, as shown in FIG. 33, include the anatomical recognition performed by the plan tracking module 226 including the vertebral levels, e.g., L2, L3, etc., and the endplate perimeter geometry 154. The plan tracking module 226 can be configured to repeatedly adjust the patient's position to arrive at the desired patient positioning, with repeated fluoro images being gathered in real time to assist the plan tracking module 226 in analyzing the patient's actual position on the bed.

Movement of the bed can be performed in any one or more of the X, Y, and Z dimensions depending on the initial position of the bed and the desired position of the bed relative to the initial position of the bed. Additionally, the movement can be translational and/or rotational in any of the X, Y, and Z dimensions.

The bed can be configured to move in a variety of ways. In an exemplary embodiment, one or more servo motors and one or more positioning sensors can be coupled to the bed. The plan tracking module 226 can be configured to transmit instructions to the servo motor(s) to translate and/or rotate the bed in a certain amount in any one or more of the X, Y, and Z dimensions to align desired targets with vertical plumb or horizontal level or an angle therebetween, and to place the desired targets on center. By adjusting position of the patient by adjusting position of something on which the patient rests (the bed), the system 10 can help reduce chances of accidental patient repositioning during surgery because the bed can provide a stable surface on which the patient rests without straps, slings, supports, etc. holding up part(s) of the patient that could accidentally loosen, shift, or otherwise slip during surgery. The servo motor(s) can be coupled to one or more jigs coupled to the bed such that actuation of one or more of the motor(s) can cause movement of one or more the jig(s), thereby adjustment an alignment of the bed, and hence an alignment of a patient on the bed. The sensor(s) can sense position of the bed and/or the jig(s) and transmit the sensed data to the system 10, which can analyze the data to ensure that the bed, and hence the patient, has been properly positioned. In an embodiment of spinal surgery, a center of a disc can be moved directly on target, or a center of a pedicle can be aligned on axis and with a user input, e.g., a user's push of a key on a keypad in communication with the system 10, a center of an opposite pedicle.

In another exemplary embodiment, one or more inflatable braces can be coupled to the bed. The brace(s) can be configured to be selectively inflated and deflated independent of any other braces coupled to the bed. The brace(s) can be coupled to the bed in locations in which the brace(s) can interact with a patient on the bed such that inflating any of the braces can cause movement of the patient. The brace(s) can thus be configured to facilitate positioning of the patient on the bed. Depending on an amount of inflation/deflation, inflating/deflating the brace(s) can cause the patient to move different amounts, thereby allowing for relatively precise adjustment of the patient's position on the bed. Similar to that mentioned above regarding the servo motor, by adjusting position of the patient by adjusting position something on which the patient rests (the brace(s)), the system 10 can help reduce chances of accidental patient repositioning during surgery because the bed and brace(s) can provide a stable surface on which the patient rests without straps, slings, supports, etc. holding up part(s) of the patient that could accidentally loosen, shift, or otherwise slip during surgery.

The brace(s) can have a variety of sizes, shapes, and configurations. In an exemplary embodiment, the brace(s) can be formed from a biocompatible, flexible, radiolucent material. The brace(s) can be coupled to the bed in any way, such as by being integrally formed therein, by being included in a slipcover placed over/around the bed, or by being attached to the bed or cover thereon with a securing element such as Velcro or glue. If the brace(s) are configured to be removably and replaceably coupled to the bed, such as with Velcro, the bed can include a diagram or other markings thereon to indicate placement of the brace(s) thereon. The markings can be generic, e.g., be for any surgical procedure, or can be customized for particular surgical procedures, e.g., be color coded with different colors indicating position of brace(s) for different surgical procedures. The brace(s) can be inflated with any one or more types of fluid. The fluid, in an exemplary embodiment, is surgically safe such that in the unlikely event of brace leakage, the fluid cannot harm the patient or surgical staff.

The system 10, e.g., the procedure analysis module 230 discussed further below, can be configured to determine an amount of time it takes to position the patient, e.g., from the system's start of the video tutorial to the system's determination that the patient's position matches the pre-surgery plan. The determined amount of time can be saved in the operation database 304, e.g., in the OR database 322. In alternative or in addition to determining an amount of time it takes to position the patient, the system 10, e.g., the personnel tracking module 236, can be configured to register (e.g., identify and log) the one or more medical personnel who help position the patient and to track movement of the one or more medical personnel who help position the patient, as discussed further below. The determined amount of time and/or the information regarding the medical personnel can be analyzed to develop metrics that can be later viewed and tracked by one or more users, such as the surgeon who performed the surgery and administrators at the hospital where the surgery was performed, to help drive learning and best practices.

Similar to that discussed above regarding facilitating patient position, the plan tracking module 226 can be configured to facilitate positioning of one or more surgical instruments before a surgical procedure begins. Also similar to that discussed above regarding facilitating patient position, the plan tracking module 226 can be configured to match one or more instruments' position with a pre-surgery plan (e.g., using positioning/navigation technology and/or imaging), and the system 10 (e.g., the equipment tracking module 230, discussed further below) can be configured to determine an amount of time is takes to position each instrument, register (e.g., identify and log) the instruments as being present, and/or to track movement of the registered instruments. The instrument movement can be tracked and logged as distinct motions, e.g., insertion and removal of the instrument into the surgical space; actions of the instruments such as removal of bone, movement of tissue, insertion of material (e.g., a bone screw, interbody cage, biologic, combination treatment, etc.), etc.; etc. The determined amount of time and/or the information regarding the instruments can be analyzed to develop metrics that can be later viewed and tracked by one or more users, such as the surgeon who performed the surgery and administrators at the hospital where the surgery was performed, to help drive learning and best practices and/or to determine instrument effectiveness.

The plan tracking module 226 can be configured to provide feedback regarding a surgical procedure throughout actual performance the surgical procedure as measured against at least one model, e.g., a saved simulated procedure and/or a pre-programmed procedure. The feedback can be provided visually (e.g., on a display device, by lights, etc.), by motion (e.g., by vibration, etc.) and/or by sound (e.g., by audio beep, etc.). The feedback can include data including a progress of the actual surgical procedure as measured against the model. The feedback can allow a surgeon and/or other medical personnel involved with the surgical procedure to continually validate and confirm that the steps being taken in the surgery line up with a saved pre-op plan and/or with convention. Should the actual procedure deviate from the model within a certain, predetermined degree of tolerance, the plan tracking module 226 can be configured to trigger an alert, e.g., a visual, auditory, and/or motion signal, indicating the deviation. Different alarms can be used by the plan tracking module 226 to indicate different deviations, e.g., a first signal for a skipped step, a second signal for an incorrect instrument being used, a third signal for a planned instrument being missing from the OR, a fourth signal for not enough tissue and/or bone removed from the patient, a fifth signal for too much tissue and/or bone removed from the patient, a sixth signal indicating unexpected patient vital sign(s), a seventh signal indicating an instrument has entered an undesirable area of the anatomy based on the pre-op plan, etc. In an exemplary embodiment, the plan tracking module 226 can be configured to predict deviation from the model within a certain, predetermined degree of tolerance and trigger the alert before the surgery has gone too far off-model or too close to a higher risk or incorrect area of the patient.

In response to an alert, the system 10 can allow a user, e.g., the surgeon, to access the surgical procedure planning module 218 to modify the saved simulation for the surgical procedure. In this way, the surgeon can prepare a plan on the fly with consideration to unexpected circumstances that arise during the procedure and/or to test different surgical techniques and/or medical devices prior to actually performing the techniques and/or actually using the medical devices. The modified simulation can be performed, saved, and later accessed similar to that discussed above.

Procedure Analysis Module

The procedure analysis module 230 can provide users of the system 10 with an interface for evaluating progress of the surgical procedure. Key metrics of progress for payers, providers, and regulators can be gathered by the procedure analysis module 230 to facilitate billing and regulatory compliance. Non-limiting examples of progress data that the procedure analysis module 230 can gather and/or analyze and provide to a user of the system 10 include anatomical information, nerve information, pain information, a running total case time, a total amount of patient blood loss, spinal disc removal information, an amount of bone removed from the patient, and an amount of tissue and/or bone removed for graft. The progress data can be selectively displayed on a display device as discussed above. The surgical procedure planning module 218 can be configured to similarly provide data to a user performing a surgical simulation so as to help correct any potential problems before an actual surgery is even performed.

Figure 22:
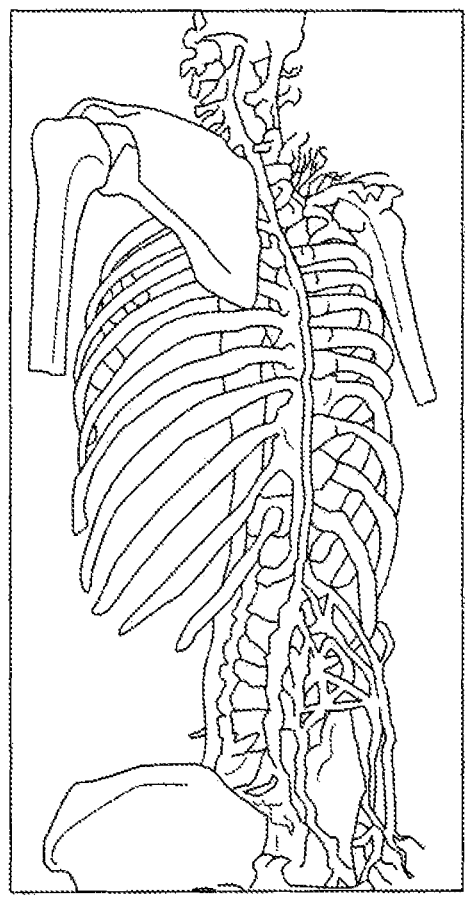
FIG. 22 is a perspective view of an embodiment of an anatomical visualization for a spinal surgery provided by the diagnosis, surgical planning, support, and management system of FIG. 2.

The provided anatomical information can include information regarding tissue (e.g., soft tissue), bone, nerves, intervertebral disc material, etc. The procedure analysis module 230 can be configured to provide anatomical information in a variety of ways. In an exemplary embodiment, the procedure analysis module 230 can be configured to provide a layered anatomical visualization on a display device. The anatomical visualization can be a generic visualization of a typical patient, or the anatomical visualization can be specifically based on the patient, similar to that discussed above regarding modeling of the patient for pre-op electronic simulation. The anatomical visualization can show all tissue types (e.g., soft tissue, bone, vessels, nerves) to help facilitate navigation around them in actual performance of the surgery. FIG. 22 illustrates one embodiment of an anatomical visualization for a spinal surgery in which a bone layer, a vessel layer, and a nerve layer are displayed, with a soft tissue layer hidden. The different layers can be selectively hidden and displayed. For surgery in another area of a patient's body, e.g., knee surgery, a different part of a patient can be shown, e.g., a portion of a leg. In some embodiments, the different layers can be selectively projected, printed, or overlaid onto the patient to facilitate identification of the patient's anatomical structures to help identify "safe" zones and avoid injury to the patient.

Using nerves as an example of the procedure analysis module 230 providing anatomical information, nerve tractography technologies such as Diffusion Tensor Imaging (DTI) or MRI with specialized sequences can be used to determine a 3D shape and location of the nerves by registering water content. The shape and location of the nerves is sensed by MRI unit, which also registers one or more fiducials on the patient. This image can be loaded into the system 10, allowing the image to be merged with the 3D anatomical model based on the reference location in space provided by the fiducial(s). This fusion can allow the system 10 to display the nerves overlaid on the bony anatomy in one or both of pre-op planning and in the OR. Additional OR sensing technologies can help to locate the nerves during surgery, such as a nerve sensing or stimulating probe using conventional triggeredEMG or triggeredMMG technology for nerve localization that can be tracked by the navigation system in order to generate spatial information about the nerve location in real time as the probe is moved during the procedure. This can accommodate tissue movement associated with patient positioning and operative manipulations. This navigable nerve sensing probe can be configured in a grid pattern rather than a single instrument, thereby allowing multiple sensing and stimulating points over the nerve. These multiple sensing and stimulation points can result in determining the distance to the nerve, and through software analysis and conduction theory, can reconstruct the size and shape of the nerve. Because the grid pattern is navigated, its location in space is known, and as a result the location of the nerve in space is known and can be merged to the 3D representation of the patient in the OR navigation system, thereby allowing visual navigation around the nerves as well as the bony structures, even as they are moved along with the muscle tissue or retracted during access.

In one exemplary embodiment, the procedure analysis module 230 can be configured to provide visualization of patient anatomy (e.g., bones, nerve roots, vascular structures, etc.) using augmented reality. The procedure analysis module 230 can be configured to provide an augmented reality imaging system that can overlay computer generated imagery onto one or more physical objects, e.g., a patient, a table, a drape, etc., that can be visualized by a user, e.g., a surgeon or other surgical staff. In an exemplary embodiment, the computer generated imagery can be overlaid on a patient, which can facilitate identification of various anatomical structures of the patient, including those structures that are hidden behind one or more other anatomical structures such that their location can be discerned from the imagery without actually being visible to the user. The imagery can be overlaid in an surgical setting, e.g., an OR, which can facilitate performance of a surgical procedure by providing visualization of patient anatomy that would otherwise not be visible. The surgery can thus be performed with improved accuracy and confidence because a more complete picture of a patient's anatomy can be provided in real time with surgery. The procedure analysis module 230 can be configured to overlay the imagery in 3D with depth perception, which can provide intuitive visualization of 3D objects that cannot be so visualized using a traditional 2D display device, e.g., a computer monitor, and that are more naturally viewed in 3D. The overlaid imagery can also be easily viewed by a user from different angles, such as by the user moving his/her head, walking around, etc. The augmented reality imaging system can allow the surgeon and/or other surgical staff in a surgical setting to focus on the patient rather than on an external display device.

The procedure analysis module 230 can be configured to provide the augmented reality imaging system in a variety of ways. In an exemplary embodiment, the procedure analysis module 230 can be configured to analyze gathered images of a patient to generate a 3D model of the patient's anatomy based on the images. The images can include previously gathered images, e.g., fluoroscopy, MRI, or CT images stored in the diagnosis database 310, and/or images gathered in real-time, e.g., fluoroscopy, ultrasound, or intraoperative CT images. The generated 3D model can be stored in the system 10, such as in the procedure database 316. The procedure analysis module 230 can be configured to register the generated 3D model to one or more reference markers mounted on a physical object, e.g., on a patient in an OR or other surgical setting. The registration can be performed automatically by the procedure analysis module 230, or the registration can be manually triggered by a user, e.g., via a no touch data communication system similar to that discussed above with respect to FIG. 20. The reference marker(s) can be similar to the augmented reality markers 72 discussed above with reference to FIG. 21. In an exemplary embodiment, a plurality of reference markers can be mounted on the patient, such as by adhering the markers to the patient using a biocompatible adhesive that allows removal of the markers from the patient. The procedure analysis module 230 can be configured to track the reference marker(s) mounted on the physical object to determine a correct location to display the generated 3D model with respect to the physical object.

A surgeon and/or other surgical staff can wear a stereoscopic viewing device, such as a head-mounted stereoscopic viewing device similar to the head mounted display 142 discussed above with reference to FIG. 20. The stereoscopic viewing device can be a see-through device, or it can be an opaque display. If the stereoscopic viewing device is an opaque display, the stereoscopic viewing device can include a video camera configured to capture a view in front of the device's wearer so that the wearer isn't "blind." The procedure analysis module 230 can be configured to track the stereoscopic viewing device to help determine where to overlay the generated 3D model in a location where it can be visualized by the wearer of the stereoscopic viewing device. The procedure analysis module 230 can be configured to use the stereoscopic viewing device to overlay the generated 3D model on the physical object, e.g., the patient, in an anatomically correct location. In other words, the procedure analysis module 230 can be configured to project the generated 3D model of anatomy in a location corresponding to the patient's actual anatomy. As the wearer of the stereoscopic viewing device moves around, the procedure analysis module 230 can be configured to automatically adjust the generated 3D model in real time so that the generated 3D model is always overlaid in the anatomically correct location. The wearer can thus use the generated 3D model as a supplement to ordinary visualization (either directly in the case of a transparent viewing device, or with the aid of the video camera in the case of an opaque device) to allow visualization of anatomy that would otherwise not be visible to the wearer.

The procedure analysis module 230 can be configured to overlay information other than anatomical information. The procedure analysis module 230 can be configured to calculate the additional overlaid information based on the patient images previously gathered and/or gathered in real time. The additional overlaid information can include, for non-limiting example, a recommended trajectory for implant implantation (e.g., a recommended implantation trajectory for a pedicle screw), dimensions of anatomy (e.g., dimensions of pedicles/vertebral bodies), a distance between various anatomical structures (e.g., a distance from one pedicle to an adjacent pedicle), and/or an estimated position and orientation of an implanted implant. The dimensions of anatomy can help a surgeon and/or other surgical staff determine an appropriate size of an implant to use with a patient, such as an appropriate screw size. The distance between various anatomical structures can help a surgeon and/or other surgical staff determine an appropriate sized implant to connect multiple anatomic structures, such as a length of spinal rod to span multiple vertebra. The estimated position and orientation of the implanted implant can help a surgeon and/or other surgical staff determine a location of the implant when the implant is otherwise not visible, e.g., if the implant is radiolucent and not visible in a gathered image of the patient. Methods and apparatuses of estimating the position and orientation of an implant are described in more detail in U.S. application Ser. No. 13/488,827 entitled "Methods and Apparatus For Estimating The Position And Orientation Of An Implant Using A Mobile Device" filed Jun. 5, 2012, which is incorporated by reference in its entirety.

Nerve information provided by the procedure analysis module 230 can include information gathered by the procedure analysis module 230 regarding, e.g., nerve health, nerve stretch, and pain levels. The procedure analysis module 230 can be configured to gather data regarding a time length of tissue retraction, an amount of the tissue retraction, and/or an amount of pressure being placed on tissue and/or nerves as a result of the retraction. The procedure analysis module 230 can gather such information using, e.g., sensors attached to a retractor and monitoring nerve diameter, RT Automatic Atlas Segmentation (available from Brainlab Corporation of Feldkirchen, Germany), etc. RT Automatic Atlas Segmentation, for example, can be used in pre-op planning to determine the pathway through nervous tissue with allowable stretch when compared to a library of nerve tension and post-op pain levels, e.g., a library stored in the procedure database 316, and can be used again during the surgical procedure to predict tissue movements without re-imaging the patient. Final imaging can compare a projected movement of the tissues to actual movement of the tissues, and the system 10 can be configured to record this relationship in the OR database 322, thereby improving the system's predictive algorithms through continual learning. If tissue is retracted during surgery for too long, the patient can feel pain following surgery. The procedure analysis module 230 can therefore analyze the gathered data to determine if the tissue retraction should be released and/or readjusted to help avoid future patient pain. The procedure analysis module 230 can be configured to determine that retraction should be released and/or readjusted based on a variety of factors, such as clinical study data, data previously gathered by the system 10 regarding lengths, locations, and durations of retraction in previously performed surgical procedures, and/or data previously gathered by the system 10 regarding pain levels of patients following surgeries. The procedure analysis module 230 can be configured to provides notification of the pain levels to the user during the surgery. The system 10 can thus be configured to correlate retraction lengths, locations, and durations with patient pain and learn over time so as to allow the procedure analysis module 230 to determine when tissue has been retracted improperly and/or for too long. In some embodiments, the procedure analysis module 230 can be configured to cause automatic release or readjustment of tissue retraction upon determination that retraction should be released or readjusted, such as when the instrument performing the retraction is coupled to a movement mechanism that can be electronically controlled by the system 10. Similarly, in some embodiments, the procedure analysis module 230 can be configured to mechanically prevent a retractor from applying too much pressure, e.g., through the use of one or more clutches. Instruments can be provided that can sense tissue segmentation through the use of ultrasound and provide the system 10 with feedback on the instrument's location in a desired tissue plane.

Spinal disc removal information gathered, analyzed, and/or provided by the procedure analysis module 230 can include, e.g., a running total amount of spinal disc removal and chemical content of disc material. The chemical content of disc material can be measured by the procedure analysis module 230 and analyzed to calculate appropriate dosing of medication.

Figure 23:
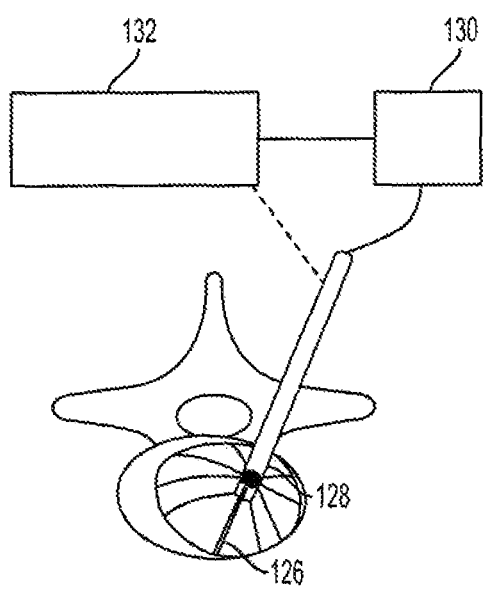
FIG. 23 is a perspective view of an embodiment of a void confirmation system that communicates with the diagnosis, surgical planning, support, and management system of FIG. 2.

FIG. 23 illustrates an embodiment of a void confirmation system of the procedure analysis module 230 configured to indicate how much intervertebral disc material has been removed from a patient's spine. It can be difficult to see how much disc material has been removed, and where it has been removed from. The void confirmation system can allow for electronic measurement of disc removal and electronic confirmation of where disc material has been removed, thereby providing better information than can typically be gathered by visualization. The void confirmation system can include at least one sensor 126 and at least one emitter 128. The sensor(s) 126 can be, e.g., a spherical IR or ultrasonic sensor or a sonar depth sensor. The sensor(s) 126 and the emitter(s) 128 can be introduced into the disc space. The sensor(s) 126 can be configured to gather data regarding a volume of unobstructed disc space, and the emitter(s) 128 can be configured to transmit the gathered data to a CPU 130 of the system 10. The system 10, e.g., the procedure analysis module 230, can be configured to analyze the received data and determine an amount of disc material that has been removed from the patient based on a comparison of the received data with previously gathered data, e.g., pre-op image data indicating a geometry of the patient's disc space. The procedure analysis module 230 can additionally or alternatively be configured to analyze received data for endplate thickness and/or density variations. The CPU 130 can be configured to display results of the analysis on a display 132. Although disc removal is shown in the illustrated embodiment, other material removed from the patient, such as tissue and bone, can be similarly electronically confirmed.

The OR analysis module 234 can be configured to track placement of implant trials (e.g., in pre-op planning) and placement of actual implants. The position of the implants and trials can be tracked using any one or more methods, such as navigation systems that use infrared or visual cameras; electromagnetic, radiofrequency, and microwave sensors attached to or embedded in the implants or trials (e.g., embedded sensors available from CardioMEMS, Inc., Atlanta, GA); etc. Embedded sensors can be used after implantation as well, such as to non-invasively collect data related to bone growth rate, forces acting on the implant, and position of the implant through wireless connection with an external interface device. Additionally or alternatively, the embedded sensors can be used to control the implants through via the system 10 and/or other external control device. For example, an implant in the form of an adjustable height interbody device can be instructed to increase or decrease its height at multiple segments in order to provide better balance or contact with the endplate to promote spinal alignment and bone growth.

Education Module

The education module 228 can provide users of the system 10 with an interface for requesting and/or receiving informational materials during performance of a surgical procedure. By providing access to informational materials in an OR, questions can be quickly answered and the surgery can proceed with minimal delay and without any medical personnel having to leave the OR to obtain the information.

The informational materials can include video conferencing capability and/or educational resources as discussed above regarding the SPP module 218, such as materials stored in the catalog database 318. The education module 228 can allow users of the system 10 to access the informational materials in any way, such by using no-touch controls, as discussed above. The system 10 can be configured to allow access to informational materials regardless of the information displayed on a display device of the system 10 at any particular time.

Video conferencing can be available to bring at least one external third party, e.g., a physician, a family member of the patient, technical staff, a resident, an expert on a certain aspect of the surgical procedure, etc.) into communication with medical personnel in the OR. The system 10 can therefore allow for remote viewing of one or more surgical procedures being performed, which can help provide training, help hospital administrators with scheduling, and/or help keep family members of the patient informed about the surgery. Data regarding the surgical procedure that can be accessed remotely can be limited based on a type of user accessing the system, e.g., more access for residents, less access for family members, etc. In an exemplary embodiment, a remote access app configured to run on a mobile phone, tablet computer, etc. can be configured to allow family members of the patient to remotely access the system 10 to receive updates regarding progress of the surgical procedure, e.g., a timeline or progress report mapping a percentage of progress of the actual surgical procedure against the pre-op plan for the procedure, thereby helping to keep family members automatically informed about the surgery's progress regardless of whether the family members are located at the hospital or not. Additionally, the app can be available for download to personal device(s) and/or available on a device issued temporarily to family members at the hospital, thereby allowing family members to access the system 10 who may not otherwise have a device at the hospital that is appropriate to access the system 10.

Equipment Tracking Module

The equipment tracking module 232 can provide users of the system 10 with an interface for managing equipment used in a surgical procedure. The equipment tracking module 232 can manage equipment by registering, tracking, and ordering equipment.

In an exemplary embodiment, equipment can be registered and tracked throughout a surgical procedure such that at any given time during the procedure (including when a patient may not necessarily be present, such as during setup and clean up), the equipment tracking module 232 can be configured to gather data regarding instrument(s) present in the OR and in a sterile configuration. The equipment tracking module 232 can therefore be configured to help manage efficient use of instruments in a surgical procedure being performed and, through subsequent analysis by the post-op module 206 of data gathered by the equipment tracking module 232, help improve efficiency, lower costs of future surgical procedures, facilitate billing, and maximize reimbursement. The equipment tracking module 232 can additionally or alternatively be configured to track registered instruments in sterilization, which can help ensure that cleaning and sterility have been performed before instruments are used in the OR, help assess quality of sterilization, help reload instruments trays more quickly, and help assist in set scheduling based on case requirements in the pre-op plan for the surgical procedure.

The equipment tracking module 232 can be configured to gather various types of data regarding instruments used in the OR. Non-limiting examples of data that the equipment tracking module 232 can be configured to gather include an identification of which and how many surgical instruments are present in the OR at any given time, how long each surgical instrument is in use during the surgical procedure, number of instrument passes/exchanges, misuse of instruments, loading and acceleration data, instrument damage, amount of power consumed by instruments, and out of instrument specification conditions. The system 10 can be configured to provide instant feedback to the user on instrument use through a display screen or feedback directly from the instrument, e.g. light, vibration, etc. Examples of instrument use feedback include misuse of the instrument, excessive force levels, or a damaged or non-functional instrument.

Equipment can be registered and tracked in a variety of ways, such as by using one or more optical and/or infrared cameras in the OR. The camera(s) can be configured to detect an instrument and compare gathered data regarding the detected instrument with equipment data stored in the equipment database 324 to register the instrument as a certain type of instrument, e.g., a scalpel, a retractor, etc., and/or as a unique instrument, e.g., identification by bar code on the instrument, identification by smart chip or radio frequency identification (RFID) tag embedded in or otherwise attached to the instrument, etc. In this way, every instrument used in the procedure and/or present in the OR can be identified, which can facilitate tracking during the procedure and facilitate use analysis (including non-use) in post-op analysis of the procedure.

One embodiment of an instrument tracking system can include an augmented reality tracking system, similar to that discussed above regarding FIG. 21. The augmented reality marker(s) 72 configured to be recognized by the RGB camera 74 can be used to track position and navigation of instruments.

Figure 24:
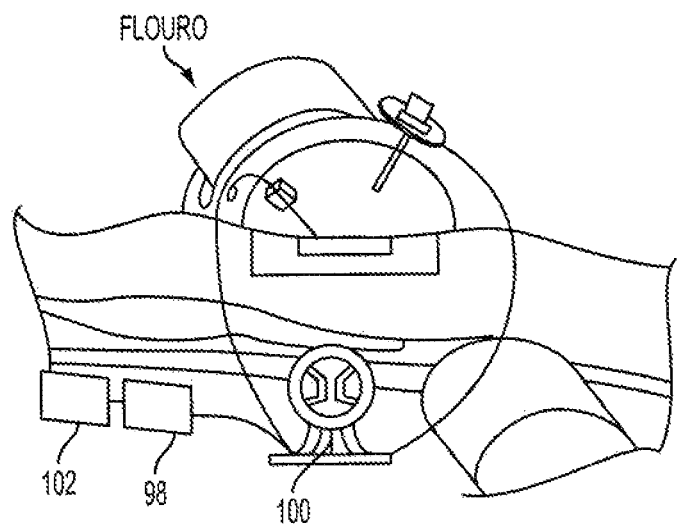
FIG. 24 is a perspective view of an embodiment of an instrument tracking system that communicates with the diagnosis, surgical planning, support, and management system of FIG. 2.

FIG. 24 illustrates an embodiment of an instrument tracking system including a magnetic based tracking system 100, such as Razer Hydra hardware available from Razer USA Ltd. of Carlsbad, CA The magnetic based tracking system 100 can be configured to communicate with a CPU 98 of the system 10, which can cause a data related to gathered tracking data to be displayed on a display 102, e.g., a list of all instruments currently in use. The magnetic based tracking system 100 can be coupled to at least one camera, e.g., a visual camera or an infrared camera, which can be configured to calibrate a location of the magnetic based tracking system 100 and use the electromagnetic tracking of the magnetic based tracking system 100 to navigate instrument(s) without requiring line of sight to the instrument from the camera(s). Whether used in conjunction with the magnetic based tracking system 100 or not, the camera(s) can be configured to record movement of the instrument(s), which can be stored in the equipment database 324 for later analysis, e.g., analysis performed by the post-op surgery feedback module 238 discussed further below.

Figure 25:
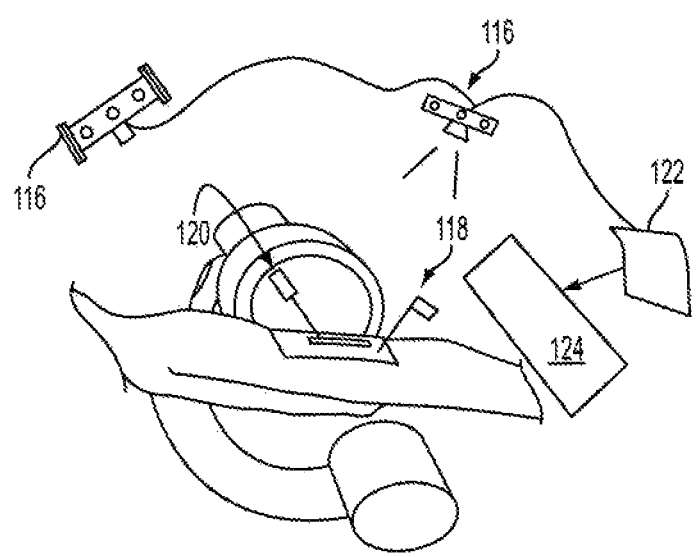
FIG. 25 is a perspective view of another embodiment of a skin surface mapping and instrument tracking system that communicates with the diagnosis, surgical planning, support, and management system of FIG. 2.

FIG. 25 illustrates an embodiment of a skin surface mapping and instrument tracking system including a positioning/navigation technology system, similar to that discussed above patient positioning assistance using positioning/navigation technology such as Microsoft Kinect. The positioning/navigation technology system can include one or more markers 118 configured to be recognized by one or more IR cameras 116. The marker(s) 118 can be positioned on and/or near the patient to facilitate tracking motion of an instrument 120 used relative to the patient. The marker(s) 118 can additionally or alternatively facilitate detection of a skin surface of the patient, determination of bone locations mapped to pre-op image(s) of the patient, and tracking of medical personnel motion and/or posture. The IR camera(s) 116 can be configured to communicate with a CPU 122 of the system 10, which can cause image(s) gathered by the camera(s) 116 to be displayed on a display 124. Fluoroscopy can be used for verification. Although only one instrument 120 is shown in the illustrated embodiment, more than one instrument can be tracked similarly to the instrument 120.

The equipment tracking module 232 can be configured to anticipate future instrument needs during a surgical procedure and trigger an instruction to retrieve the instrument(s) identified as being needed and, if necessary, prepare the retrieved instrument(s) for imminent use. The equipment tracking module 232 can be configured to determine what instrument will next be needed based on any number of factors, such as on previously gathered data stored in the procedure database 316 and/or the products and procedures database 320 regarding previously performed surgical procedures of a same type as the surgical procedure being performed, on the surgical procedure's pre-op plan as indicated in a simulation saved in the procedure database 316, and/or on the flow of the surgical procedure performed thus far. The equipment tracking module 232 can be configured to identify all next-needed instruments, or the equipment tracking module 232 can be configured to determine which instrument(s) are critical to the surgical procedure based on their frequency of use in previously performed surgical procedures of a same type as the surgical procedure being performed and only trigger an instruction for the critical instrument(s). In an exemplary embodiment, the equipment tracking module 232 can be configured to trigger an instruction for all next-needed instruments, regardless of their actual or calculated criticality to the procedure.

The triggered instruction can take any number of forms, such as by identifying an instrument for a medical staff member to retrieve and/or prepare for the surgeon. The identification can be achieved in any number of ways, such as by displaying the instrument on a display screen with a notation that the instrument is needed now or in "X" amount of time, laser pointing to the instrument on an instrument tray, lighting up the instrument's location on an instrument tray, etc.

In some embodiments, retrieval of instruments can be automated, such as by a robotic scrub tech or vending machine/tool changer configured to provide each successive instrument. The robotic scrub tech or vending machine/tool changer can be configured to pick up each successive needed instrument, pass the instrument through a sterile field (e.g., flash sterilization, chemical sterilization, etc.), and deliver the sterilized instrument to a scrub tech. The robotic scrub tech or vending machine/tool changer can thus help reduce instrument sterilization costs because only instruments used are sterilized, rather than sterilizing an entire instrument set. The robotic scrub tech or vending machine/tool changer can be configured to receive a triggered instruction from the equipment tracking module 232 such that only instruments identified as being needed as sterilized on as as-needed basis.

As mentioned above, the equipment tracking module 232 can be configured to verify cleanliness and/or sterilization of instruments in the OR. In an exemplary embodiment, both cleanliness and sterilization can be verified. The equipment tracking module 232 can be configured to verify cleanliness and sterilization in a variety of ways, such as by using a built-in ultraviolet light and an optical camera configured to recognize instruments. The equipment tracking module 232 can additionally or alternatively be configured to determine when a non-sterilized instrument has breached the sterile field of the OR, e.g., by registering the instrument and identifying the instrument as not being noted in the equipment database 324 as having passed through sterilization, and if so, to trigger an alert to user(s) of the system 10 in the OR. The equipment tracking module 232 can be configured to provide a warning, e.g., a visual warning on a display, etc., may if a sterile instrument has been removed from the sterile field.

As also mentioned above, the equipment tracking module 232 can be configured to help reload instruments trays more quickly, since time is often wasted in refilling trays after cleaning instruments in central sterilization. The equipment tracking module 232 can facilitate reload of instruments trays in a variety of ways. FIG. 26 illustrates an exemplary embodiment of an instrument sorting system configured to allow the equipment tracking module 232 to help reload instruments trays more quickly. The instrument sorting system can include an IR and RGB camera 104 configured to gather data regarding an instrument 108 and communicate the gathered data to a CPU 106 of the system 10. The CPU 106, e.g., the equipment tracking module 232 executed by the CPU 106, can be configured to analyze the received data to identify the instrument 108 and provide instructions as to which instrument tray 110 and where in the instrument tray 110 the instrument 108 should be placed (if placement of the instrument 108 in the tray is relevant, e.g., if the instrument 108 is not the only instrument on or to be on the tray 110). The CPU 106 can provide the instruction in a variety of ways. In the illustrated embodiment, the CPU 106 can be coupled to a laser pointer 112 configured to communicate orders to medical personnel by directing medical personnel to the specific tray 110 by laser pointing to the tray 110 and/or a specific location on the tray 110. The laser pointer 112 can be coupled to a movement mechanism, e.g., a rotation mount 114, configured to move in response to instructions received from the CPU 106, e.g., instructions to rotate a certain amount in a certain direction to cause the laser pointer 112 to point to tray 110 and/or a specific location on the tray 110. The laser pointer 112 can include a camera (not shown) configured to provide visual confirmation on a user interface that the laser pointer 112 has pointed to the tray 110, which can allow a user to visually confirm the instruction. Although only one instrument 108 is shown in the illustrated embodiment, the IR and RGB camera 104 can be configured to gather data regarding a plurality of instruments, and the CPU 106 can be configured to analyze data regarding the plurality of instruments and provide tray instructions regarding the plurality of instruments.

The equipment tracking module 232 can be configured to trigger maintenance/sharpening/lubrication/recalibration/disposal cycles of instruments tracked by the equipment tracking module 232. In an exemplary embodiment, when the equipment tracking module 232 registers an instrument is registered as being used in a surgical procedure, the equipment tracking module 232 can cause the scheduling module 222 to determine whether the instrument needs to undergo maintenance/sharpening/lubrication/recalibration/disposal, e.g., if the instrument has been used a certain predetermined number of times as indicated by running tally of uses in surgery detected by the system 10, and if so, to schedule the maintenance/sharpening/lubrication/recalibration/disposal. In this way, the equipment tracking module 232 can help ensure that instruments are maintained in their best possible condition. The equipment tracking module 232 can be configured to provide data on instrument use to a product manufacturer. Examples of the provided data include number of instrument uses, instrument failure, maintenance and calibration cycles of instruments, and real-time complaint reporting. The equipment tracking module 232 can be configured to verify that all instruments and disposables have been removed from the surgical site and are not remaining in the patient.

OR Analysis Module

The OR analysis module 234 can be configured to provide users of the system 10 with an interface for gathering ethnographic information regarding a surgical procedure. The system 10 can thus be configured to analyze each surgical procedure on the basis of one or more factors such as instrument use efficiency, personnel efficiency, and patient health, as well as be configured to aggregate data regarding multiple surgical procedures so as to learn trends over time. Individual analysis of surgical procedures can help predict outcomes of the procedure and/or can help the surgeon establish best practices and learn from previous experience on a personal, confidential level as evaluated by the system 10 acting as a neutral third party. Aggregated data can help hospital administrators develop a cost per hour for OR time, which can allow the hospital to improve efficiency and lower costs.

The OR analysis module 234 can be configured to review data collected over multiple surgical procedures, and can be configured to group the data according to one or more factors such as performing surgeon, procedure type, patient demographic, instruments and implants used, duration, etc. The data can include parameters such as anatomic, physiologic, ergonomic, temporal, spatial, and biomechanical parameters. The system 10, e.g., the post-op module 206, can be configured to perform an analysis on the collected data through one or more algorithms to generate potential new innovations to the surgical procedure, such as a combining of steps, introduction of a new tool from a different procedure, adjustment of a physical location of OR staff or equipment, etc. These generated innovations can then be available for review by users of the system 10, e.g., a user planning a new surgical procedure, and can be integrated into future cases. The system 10 can be configured to record when the innovation was used and can be configured to track the outcomes of these procedures to compare against the outcomes from similar patients/procedures before the innovation was used. The system 10 can be configured to determine through comparison how effective the innovation was, resulting in further learning of the system 10 on how and when to generate the most effective innovations. This analysis can also help the system 10 determine if it would be beneficial to continue recommending this innovation to users and eventually include it as a standardized part of the procedure or to remove it due to its lack of effectiveness.

The system 10 can be configured to automatically, continually gather data throughout every surgical procedure at an OR in which the system 10 is set up, e.g., by camera (still image and/or video image), audio recording, motion sensor, etc., thereby allowing for seamless data gathering largely transparent to medical personnel in the OR. The OR analysis module 234 can be configured to coordinate this data gathering. The system 10, e.g., the post-op module 206 discussed further below, can thus be configured to automatically generate efficiency reports at a user-set frequency, e.g., for every procedure, for all procedures performed in one day at a hospital, for every "X" number of a certain type of procedure performed, etc., which can facilitate analysis and use of the data gathered by the system 10.

Multiple technologies present in an OR can be integrated with the system 10, thereby allowing centralized management and monitoring of multiple technologies. The technologies can be modular, as mentioned above, thereby allowing scaling of the system 10 to hospitals, clinics, etc. of largely varying size and resources, and/allowing the various technologies to be upgraded, replaced, and/or maintained without requiring shutdown of the entire system 10. The OR analysis module 234 can be configured to provide a user interface allowing selective operation and/or user settings of any one or more of the technologies at a given time, thereby allowing for modular and personalized control of the various technologies. Non-limiting examples of technologies that can be integrated with the system 10 can include neural monitoring outputs, educational information (e.g., surgical technique videos, etc.), imaging (e.g., CT, fluoroscopy, ultrasound, etc.), navigation, neural monitoring, lighting, cameras (e.g., endoscope, microscope, feeds from outside the OR, etc.), power usage of instruments, energy devices (e.g., bovie, bipolar, harmonic devices, etc.), powered tools (e.g., burr, drill, etc.), video outputs (e.g., output video to OR screens), projected images, heads-up displays (e.g., in microscope, loupes, glasses, etc.), connection to a hospital network, vital sign monitoring, robotic control (e.g., control of instruments through pre-planned navigated space such as disc-clearing robots, etc.), remote viewing of the system 10, anesthesia, full room decontamination activated after case completion and timed by the scheduling module 222, etc. The technologies can be linked virtually through the system 10, e.g., through a central interface and processor residing in the OR analysis module 234. The system 10 can be configured to manage and display the inputs and outputs of each technology on a common display and input device, or they can be physically combined into one central unit, where each technology physically plugs in to the unit in a rack system or comes as an integrated part of the system from the manufacturer. This physically integrated unit can allow for simplification of systems and/or allow for a reduction in the amount of wires and carts in the OR, and can be scaled in the number of technologies present as needed, or technologies can be added using plug-and-play technology to meet the needs of the surgical case or location of the unit. The technologies can be configured to interface through a standardized operating system of the system 10 that can allow seamless compatibility and integration of newly developed or applied technologies.

Personnel Tracking Module

The personnel tracking module 236 can provide users of the system 10 with an interface for managing and tracking medical personnel involved in a surgical procedure. As mentioned above, one or more medical personnel present in the OR can be registered and tracked, such as a surgeon, first assistance, scrub tech, and any other surgical staff. In an exemplary embodiment, the medical personnel can be tracked throughout the surgical procedure such that at any given time during the procedure (including when the patient may not necessarily be present, such as during setup and clean up), the personnel tracking module 236 can be configured to gather data regarding medical personnel present in the OR. The personnel tracking module 236 can therefore be configured to determine which and how many medical personnel are present in the OR at any given time and how long each of the medical personnel are present in the OR during the surgical procedure. In an exemplary embodiment, medical personnel are registered and tracked by the personnel tracking module 236, and surgical instruments are registered and tracked by the equipment tracking module 232, thereby helping to provide a more complete picture of the surgical procedure for analysis, which can help improve performance of future surgical procedures.

The medical personnel can be registered and tracked in a variety of ways, similar to that discussed above regarding equipment tracking by the equipment tracking module 232, such as by using one or more of optical and/or infrared cameras in the OR, smart clothing monitors, sensors in instruments, motion capture, and body sensors. Non-limiting examples of types of personnel data that the personnel tracking module 236 can be configured to gather include physiological data (e.g., heart rate, eye movement, time to perform each step in a surgical procedure, body temperature (e.g., via infrared measurement, laser measurement, contact sensors, etc.), posture, fatigue, effort/force applied to instruments (e.g., as indicators of stress), etc.), an identification of which and how many medical personnel are present in the OR at any given time, how long each medical personnel member is present during the surgical procedure, number of personnel changes, personnel injury, radiation exposure (e.g., without medical personnel each having to wear a radiation monitoring device such as a dosimeter), etc. The personnel data can relate to patient outcome, as analyzed by the post-op module 206 discussed further below, so gathering and analyzing personnel data can help hospitals plan better (e.g., make changes to OR staff, leave more time between cases, schedule more frequent and/or longer breaks, etc.) and achieve better patient outcomes. The personnel data can also help indicate if particular staff are particularly skilled at a certain surgical procedure and/or certain aspects of a surgical procedure, which can help identify potential training candidates who can instruct others as to their technique.

The personnel tracking module 236 can be configured to anticipate future personnel needs during a surgical procedure and trigger an instruction to page, call, email, or otherwise request the presence of a specific type of medical staff member or a specific individual identified as being needed in the OR. The personnel tracking module 236 can be configured to determine which personnel will next be needed based on any number of factors, such as on previously gathered data stored in the procedure database 316 and/or the products and procedures database 320 regarding previously performed surgical procedures of a same type as the surgical procedure being performed, on the surgical procedure's pre-op plan as indicated in a simulation saved in the procedure database 316, and/or on the flow of the surgical procedure performed thus far. The instruction can indicate an estimated amount of time before the requested personnel is needed in the OR. The personnel tracking module 236 can thus allow medical personnel to maximize use of their time outside the OR by being called to the OR when they are needed. In other words, unnecessary wait time outside the OR can be minimized. Unexpected scenarios arising during the surgery that require additional medical personnel can also be more quickly addressed by the personnel tracking module 236 being configured to request additional medical personnel in real time without anybody currently present in the OR having to leave the OR or even free their hands or leave their current location in the OR.

The tracking of personnel can be used as a reminder to staff to continue to use standard infection prevention methods. For example, patient interactions can be monitored such that when moving from one room to another a reminder (e.g., a blinking light on a wrist band, etc.) can activate to make the staff aware that hand washing and/or other appropriate infection prevention methods are suggested.

Similar to that discussed above regarding the equipment tracking module 232, the personnel tracking module 236 can be configured to determine when a non-sterilized personnel member has breached the sterile field of the OR, e.g., by registering the personnel member and identifying the instrument as not being noted in the ethnography database 326 as having passed through sterilization, and if so, to trigger an alert to user(s) of the system 10 in the OR.

The personnel tracking module 236 can communicate with the scheduling module 222 to help drive OR personnel flow in multiple ORs and allow for automatic rescheduling if medical personnel become unavailable due to, e.g., an unexpected duration of a surgical procedure. The personnel tracking module 236 can thus also allow for more efficient determination of when to start prepping patient, transferring them etc. based on personnel availability. This can lead to the development of cost per hour of OR time, and/or the tracking of how the efficiencies reduce the OR time and therefore cost. The cost per hour of OR time and the efficiencies can be stored in the OR database 322 and/or the equipment database 324.

The personnel tracking module 236 can be configured to gather data regarding registered OR personnel even when the OR personnel are outside the OR and are not actively involved in a case. Non-limiting examples of "outside" data that the personnel tracking module 236 can be configured to gather include nutrition and energy level. Collection of the "outside" data can help the system 10 determine if and how various factors affect case outcomes, and make recommendations for personal changes (e.g., changes in behavior, rest, nutrition, case scheduling, etc.) to improve outcomes. The personnel data can be made available by the system 10 only to the user about which the personnel data was gathered, which can help ensure privacy and help ensure that team morale is not affected, and/or the personnel data can be made available (anonymously or non-anonymously) to users other than the user about which the personnel data was gathered, which can allow for more broad-based data trend analysis.

Post-Op Module

The post-op module 206 can generally provide users of the system 10 with an interface for analyzing a performed surgical procedure and managing patient post-op treatment. More particularly, the post-op module 206 can allow a surgeon to review data gathered and analyzed by the operation module 204 regarding surgeries performed by the surgeon, which can help a surgeon evaluate his/her performance for efficiency, future improvements, etc., and/or can help a hospital or other care facility evaluate surgery logistics such as personnel needs, surgical instrument inventories, OR use times, etc. The post-op module 206 can also analyze the data gathered and analyzed by the operation module 204 to help improve future recommendations of the diagnosis and treatment module 200 regarding effective treatments, and/or help improve future recommendations of the pre-op module 202 regarding simulated surgeries using instruments and/or personnel similar to previously performed surgeries. The post-op module 206 can also suggest post-op treatment options for the patient and can manage the patient's post-op treatment. In this way, the post-op module 206 can be configured to assist with post-op planning and analysis through a continuum from an end of surgery to the patient's discharge instructions. The post-op module 206 can be configured to compares physical, functional, HRQOL, and health economic data describing an actual outcome to predicted values for each parameter that were predicted by the pre-op module 202 during planning. The post-op module 206 can be configured to detect and analyze any variances and can be configured to modulate future predictive models using the detected and analyzed variances.

In one embodiment, the post-op module 206 can be implemented using one or more web pages which are configured to receive user input and present information to a user. In an exemplary embodiment, both patients and medical practitioners can access at least a portion of the post-op module 206.

The post-op module can be used as an educational tool for potential patients with regard to the expectations of post-operative care, post-operative pain, etc.

The post-op module 206 can include a surgery feedback module 238, a post-op treatment module 240, a post-op patient care module 242. Each of the modules 238, 240, 242 is discussed further below in turn.

As mentioned above, the post-op module 206 can be configured to read information from and write information to the post-op database 306. The post-op database 306 can include a treatment plan database 328. Various ones of the post-op module's component modules 238, 240, 242 can be configured to access one or more of the treatment plan database 328 and/or various other databases, e.g., the diagnosis and treatment database 300, the pre-op database 302, the operation database 304, and the recovery database 308. The treatment plan database 328 is discussed further below in connection with the post-op module's component modules 238, 240, 242.

Surgery Feedback Module

The surgery feedback module 238 can provide users of the system 10 with an interface for analyzing a performed surgical procedure. In an exemplary embodiment, only medical administrators and medical personnel can access the surgery feedback module 238. Some aspects of the surgery feedback module 238, such as video of the surgery or comparison between the actual surgical procedure and a pre-op plan, can be accessible to only the performing surgeon, which can help prevent damage to team morale and help protect privacy. The surgery feedback module 238 can, however, be configured to allow the performing surgeon to make aspects of the surgery feedback module 238 that are accessible to only the performing surgeon available to one or more other users of the system 10, e.g., residents, insurance providers, etc., which can help facilitate training and/or billing.

Various types of data gathered and/or analyzed by the system 10 during and before a surgical procedure can be displayed on a user interface and/or otherwise made available to users of the system 10. FIG. 27 illustrates an embodiment of a user interface 148 showing various types of data related to a previously performed surgical procedure. The user interface 148 shows three images of a surgical site captured at a same time from three different perspectives provided by the navigation software with actual post-op images of the implant placement. Another portion of the user interface 148 (top right quadrant) shows a patient x-ray of the surgical site. By allowing the user to view different data and to compare the pre-op planned placement with the actual post-op result simultaneously, the user can better evaluate success of the surgical procedure, including compliance of the surgery with the pre-op plan.

Different types of data can be displayed to a user other than the information shown on the user interface 148, such as time durations of certain steps of the surgical procedure, a total time duration of the surgical procedure, information gathered by the equipment tracking module 232 regarding equipment used in the surgical procedure, information gathered by the personnel tracking module 236 regarding personnel involved with the surgical procedure, a saved pre-op simulation, still or moving image data of all or a portion of the surgical procedure captured by the procedure analysis module 230, tissue removal data gathered by the procedure analysis module 230, pre-op images of the patient stored in the diagnosis database 310, the patient's pre-op treatment compliance stored in the treatment database 312, etc. The surgery feedback module 238 can thus allow each user to evaluate performed surgical procedures in a way most informative and useful for that particular user.

For non-limiting example, a hospital administrator may be concerned with personnel issues to help plan future scheduling of personnel for future surgeries, so the hospital administrator may request that the surgery feedback module 238 provide personnel data gathered during the surgical procedure by the personnel tracking module 236 but not other data gathered by the operation module 204 during the surgical procedure. The hospital administrator may thus be able to determine various personnel issues from the performed surgical procedure and/or from a plurality of performed surgical procedures, such as which types of medical personnel may be redundant in a certain type of surgical procedure, which types of medical personnel should be scheduled at certain times for certain surgeries, whether any particular medical staff member is involved with over "X" number of failures, etc.

For another non-limiting example, the performing surgeon may be most concerned with tracking of the actual surgical procedure against the pre-op plan and may thus request a report from the surgery feedback module 238 indicating deviations of the actual surgical procedure against the pre-op plan. The deviations can be presented as percentage compliance with respect to factors such as goal outcomes, time differences, differences in surgical instruments used, differences in angles of trajectory, differences in patient blood loss, measures against validated procedures (e.g., measures against defined steps that have been shown over time to be effective surgical steps through the continual analysis of patient outcomes proving the superior efficacy and safety of these defined steps), etc., so the surgeon can make decisions such as possible changes to make in future surgical procedures, requests for additional educational materials to be available for future surgical procedures, issues to address in the patient's post-op treatment, notes for possible follow-up surgery, etc.

For another non-limiting example, an insurance administrator may be concerned with a surgeon's compliance with validated procedures and/or specific measures such as reduced re-operations or lower infection rates because the more a surgeon follows validated procedures and complies with specific measures over time, the lower the surgeon's insurance rates could become because the surgeon has been proven to follow validated procedures and complied measures. Similarly, the insurance administrator may be concerned with a surgeon's success rate because the higher a surgeon's success rate, the lower the surgeon's insurance rates could become because the surgeon has been proven to perform effective surgeries. The insurance administrator may therefore request, e.g., a measures against validated procedures report from the surgery feedback module 238 for review by the insurance administrator and/or an insurance carrier. The measures against validated procedures report can be customized by user selection to be over a certain period of time for a certain surgeon and/or a certain type of surgery, to include the last "X" number of surgeries performed by a particular surgeon or group of surgeons at a particular hospital, etc.

The surgery feedback module 238 can be configured to generate one or more post-op reports summarizing the surgery performed. The report can be a brief, one page or less report showing a snapshot of the surgery, which can help quickly inform and/or remind medical practitioners of the surgery performed on a patient and/or help a patient accurately describe the surgery to third parties, such as their PCP, family members, and airport security (who may need, e.g., precise information regarding implants in the patient or medication prescribed to the patient). Each post-op report generated can be targeted to a particular user, such as the performing surgeon, the patient's PCP, or the patient. A post-op report generated for a medical practitioner such as the performing surgeon or the patient's PCP can include medically precise information regarding the surgery and/or the patient, such as the type of surgery performed, the medical devices implanted in the patient, date of the surgery, the medications administered to the patient, projected success rate of the surgery based on historic success rates of the surgery and the patient's particular surgery, etc. A post-op report generated for a patient can include information that is less medically precise than on a report for a medical practitioner, such as the medical devices implanted in the patient, date of the surgery, type of procedure performed, list of medications administered during the procedure, a total time length of the procedure, a projected reimbursement by the patient's insurance, name of and contact information for the performing surgeon, name of and contact information for the hospital or other facility at which the surgery was performed, etc. Post surgical results and metrics stored in the operation database 304 and/or in the recovery database 308, such as length of stay, infection rate, fusion rate, blood loss, etc., can be tracked by the hospital and/or surgeon and can be used to drive patient awareness around quality of care and/or used with payers to help support reimbursement negotiations.

Any of the modules discussed herein can be configured to generate a report similar to the post-op report summarizing the data gathered and/or analyzed by the particular module, which can help keep medical practitioners and patients informed throughout the patient's care.

Post-Op Patient Care Module

The post-op patient care module 242 can provide users of the system 10 with an interface for managing and analyzing a patient's in-hospital post-surgery care. The post-op patient care module 242 can be configured to provide one or more one or more recommended post-op care options based on the efficacy of the surgery as analyzed by the surgery feedback module 238 and/or as indicated by manual input from the performing surgeon and/or other user of the system 10. None, some, or all of the recommended post-op care options can be followed, but by providing a full range of post-op care options, the post-op patient care module 242 can help prevent any post-op care decisions from being overlooked or under-appreciated for a particular patient. Non-limiting examples of post-op care options can include medication types and frequencies of dosage, length of post-op hospital stay, appropriate hospital unit for patient stay post-surgery, appropriate diet for post-op hospital stay, frequency of vital sign measurements, and post-op imaging (x-rays, CT scan, etc).

The post-op patient care module 242 can be configured to determine post-op care options in a variety of ways. Similar to that discussed above regarding the treatment options module 212 and the treatment database 312, the post-op patient care module 242 can be configured to compare pre-op and op data for a particular patient with post-op care options stored in the treatment plan database 328 and determine which of the plurality of possible post-op care options are associated with the patient's diagnosis (as stored in the diagnosis database 310), the patient's demographics (as stored in the diagnosis database 310), the patient's current level of radiation exposure, the patient's care provider (as not all care options may be available at the patient's current location, so transfer of the patient may be appropriate as part of the patient's post-op care), the type of surgery performed on the patient (as stored in the treatment database 312 and/or the products and procedures database 320), and/or the surgery's effectiveness (as stored in the treatment database 312 and/or the products and procedures database 320). The post-op patient care module 242 can be configured to cause a display screen to show a list of the possible post-op care option(s). The possible post-op care option(s) can be provided to the user with a caution that the possible post-op care option(s) are preliminary only and that the user should consider the patient's circumstances in determining a post-op care plan. The possible post-op care option(s) can be provided to the user with historic success rates of each of the possible post-op care option(s). The historic success rates can be stored in the treatment plan database 328 for each of the post-op care options and can be manually entered. Alternatively or in addition, the historic success rates can be based on data collected by the system 10 regarding a plurality of patients such that the system 10 can act as a feedback loop system in which previously collected data regarding post-op care treatments received by actual patients can inform post-op care options for future patients. The possible post-op care option(s) can be provided to the user with educational resources for at least one of the options, e.g., links to informational web pages stored in the system 10 (e.g., in the treatment plan database 328), links to third party educational websites, lists of or links to journal articles or books, links to medical device product brochures (e.g., brochures stored electronically in the system 10), etc.

In some embodiments, the post-op patient care module 242 can provide coding and reimbursement information for each of the suggest post-op care options. Providing such information can facilitate educated decision-making about which of the post-op care options to pursue (if any).

By suggesting post-op care option(s) to a user, the post-op patient care module 242 can allow the user to receive and analyze information that may be outside their area of medical expertise. The post-op patient care module 242 can allow the user to become quickly informed about unfamiliar aspects of the patient's case (e.g., a specific abnormal surgical outcome or with a particular new medication) by recommending particular post-op care options to address unfamiliar as well as familiar aspects of the patient's case, which can facilitate swift, effective treatment of the patient and/or facilitate education of the user and the user's colleagues to which the user may discuss the unfamiliarities.

Post-Op Treatment Planning Module

The post-op treatment planning module 240 can provide users of the system 10 with an interface for receiving one or more post-op treatment plan options based on the post-op care of the patient and on the efficacy of the surgery as analyzed by the surgery feedback module 238 and/or as indicated by manual input from the performing surgeon and/or other user of the system 10. None, some, or all of the recommended post-op treatment plan options can be followed, but by providing a full range of post-op treatment plan options, the post-op treatment planning module 240 can help prevent any post-op treatment decisions from being overlooked or under-appreciated for a particular patient. Non-limiting examples of post-op treatment plan options can include medication types and frequencies of dosage, type and duration of physical therapy, type and duration of occupational therapy, at-home exercise types and frequency, appropriate timing of follow-up doctor visits, and appropriate at-home diet.

The post-op treatment planning module 240 can be configured to determine post-op treatment plan options in a variety of ways. In an exemplary embodiment, the treatment plan database 328 can include a plurality of possible post-op treatment options, each of the possible post-op treatment options being associated with at least one possible diagnosis. This post-op treatment options data can be organized in any way, such as in a table. Similar to that discussed above regarding the treatment options module 212 and the treatment database 312, and the post-op patient care module 242, the post-op treatment planning module 240 can be configured to compare pre-op data, op data, and post-op care data for a particular patient with post-op treatment options stored in the treatment plan database 328 and determine which of the plurality of possible post-op treatment options are associated with the patient's diagnosis (as stored in the diagnosis database 310), the patient's demographics (as stored in the diagnosis database 310), the patient's current level of radiation exposure, the patient's care provider (as not all care options may be available from the patient's doctor), the patient's post-op care, the type of surgery performed on the patient (as stored in the treatment database 312 and/or the products and procedures database 320), and/or the surgery's effectiveness (as stored in the treatment database 312 and/or the products and procedures database 320).

The post-op treatment planning module 240 can be configured to cause a display screen to show a list of the possible post-op treatment option(s). The possible post-op treatment option(s) can be provided to the user with a caution that the possible post-op treatment option(s) are preliminary only and that a user should consider the patient's circumstances in determining a post-op treatment plan. The possible post-op treatment option(s) can be provided to the user with historic success rates and/or with projected outcome scenarios of each of the possible post-op treatment option(s). The historic success rates can be stored in the treatment plan database 328 for each of the post-op treatment options and can be manually entered. Alternatively or in addition, the historic success rates can be based on data collected by the system 10 regarding a plurality of patients such that the system 10 can act as a feedback loop system in which previously collected data regarding post-op treatments received by actual patients can inform post-op treatment options suggested to future patients. The possible post-op treatment option(s) can be provided to the user with educational resources for at least one of the options, e.g., links to informational web pages stored in the system 10 (e.g., in the treatment plan database 328), links to third party educational websites, lists of or links to journal articles or books, links to medical device product brochures (e.g., brochures stored electronically in the system 10), etc. The projected outcome scenarios can be based on one or more factors, such as historic outcomes, the patient's demographics, the patient's lifestyle, the patient's compliance with pre-surgery treatment as gathered by the treatment compliance module 216 and stored in the treatment database 312, etc.

In some embodiments, the post-op treatment planning module 240 can provide coding and reimbursement information for each of the suggest post-op treatment options. Providing such information can facilitate educated decision-making about which of the post-op treatment options to pursue (if any).

The possible treatment options suggested by the post-op treatment planning module 240 can include non-surgical treatment options (e.g., diet adjustments, exercise regimens, medications, etc.) and surgical treatment options (e.g., specific surgical procedures). In an exemplary embodiment, only non-surgical treatment(s) can be initially suggested to a user of the system 10. In this way, a conservative treatment can be pursued before a more radical, typically more costly treatment such as follow-up surgery is pursued. If one or more of the non-surgical treatments are pursued and are determined to unsatisfactorily address a patient's problem(s), then the post-op treatment planning module 240 can be configured to suggest one or more surgical treatment options. The post-op treatment planning module 240 can be configured to suggest the one or more surgical treatment options upon request by a user, e.g., when a medical practitioner requests non-conservative treatment options for a particular patient, and/or can be configured to suggest the one or more surgical treatment options when a trigger event occurs, e.g., after a predetermined threshold amount of time passes from commencement of a non-surgical treatment for a patient after which the patient has not shown a predetermined amount of improvement. By way of non-limiting example, the post-op treatment planning module 240 can be configured to analyze data gathered by the recovery module 208, discussed further below, and determine whether the patient's mobility has improved by a certain degree after a certain amount of time as indicated by reported pain levels and/or analysis of captured images. Before the post-op treatment planning module 240 suggests one or more surgical treatment options following determination that a non-surgical treatment is not achieving a desired outcome, the post-op treatment planning module 240 can be configured to first suggest one or more other non-surgical treatments.

By suggesting treatment option(s) to a user, the post-op treatment planning module 240 can allow the user to receive and analyze information that may be outside their area of medical expertise, similar to that discussed above regarding the treatment options module 212 and the post-op patient care module 242.

Recovery Module

The recovery module 208 can generally provide users of the system 10 with an interface for managing and evaluating a patient's recovery from surgery. More particularly, the recovery module 208 can allow a patient to monitor and manage their post-surgery recovery, such as to record personal data (e.g. pain levels, mobility, time to return to work, compliance with medication, compliance with physical therapy, etc.) and compare their recovery progress against their personal targets and/or against others having similar demographics to the patient. The recovery module 208 can also allow medical professionals to review data gathered and analyzed by the recovery module 208 regarding the patient's post-surgery recovery, which can help the medical professionals monitor the patient's progress and provide the patient with updated and/or revised recovery planning tools and/or recovery activities to help the patient maximize recovery potential. The recovery module 208 can also analyze the data gathered regarding the patient's recovery from surgery to help improve future recommendations of the post-op module 206 regarding effective recovery options for patients having similar demographics to the patient.

In one embodiment, the recovery module 208 can be implemented using one or more web pages which are configured to receive user input and present information to a user. In an exemplary embodiment, both patients and medical practitioners can access at least a portion of the recovery module 208.

The recovery module 208 can include a patient monitoring module 244 and a efficacy analysis module 246. Each of the modules 244, 246 is discussed further below in turn.

As mentioned above, the recovery module 208 can be configured to read information from and write information to the recovery database 308. The recovery database 308 can include a patient targets database 330 and a surgery targets database 332. Various ones of the post-op module's component modules 244, 246 can be configured to access one or more of the patient targets database 330, the surgery targets database 332, and/or various other databases, e.g., the diagnosis and treatment database 300, the pre-op database 302, the operation database 304, and the post-op database 306. The patient targets database 330 and the surgery targets database 332 are discussed further below in connection with the recovery module's component modules 244, 246.

Patient Monitoring Module

The patient monitoring module 244 can provide users of the system 10 with an interface for monitoring and managing their post-surgery recovery. Similar to the treatment compliance module 216, the patient monitoring module 244 can provide users of the system 10 with an interface for tracking patient compliance with a post-op treatment plan. The post-op treatment plan can be one of the suggested treatment options suggested by the post-op treatment plan module 240, can be one of the suggested treatment options suggested by the post-op treatment plan module 240 as modified by a medical practitioner, or can be a treatment plan entered into the system 10 by a medical practitioner without assistance of the post-op treatment plan module 240. The post-op treatment plan can be stored in the treatment plan database 328. The patient monitoring module 244 can thus allow monitoring and management of a patient's post-op treatment, which can help the patient's doctor evaluate the patient's progress and/or can help determine whether and when modifications to the post-op treatment plan may be necessary, either adjustment of the post-op treatment plan (e.g., changing dietary requirements, changing a frequency of doctor check-ups, etc.) or replacement of the post-op treatment plan (e.g., a non-surgical treatment) with another treatment plan (e.g., a surgical treatment).

Patients and users other than patients can submit data to the patient monitoring module 244 for storage in the treatment plan database 328. Data can therefore be received by the patient monitoring module 244 whether the patient is in or not in a medical setting and can be received throughout the patient's post-op treatment and not just when the patient visits or consults a medical practitioner. More accurate and more timely data regarding post-op treatment plan compliance can therefore be gathered and analyzed. Users can submit data to the patient monitoring module 244 similar to that discussed above regarding submission of data to the diagnosis module 210 and to the treatment compliance module 216.

Data can be provided to the patient monitoring module 244 actively by the patient and/or other users entering the data manually, or data can be provided passively, e.g., through the use of sensors or devices autonomously collecting data defined as a part of the post-op treatment plan. Examples of devices and sensors used to collect the passive data include smartphone or tablet integrated devices (e.g., cameras, gyroscopes, accelerometers, global positioning systems, etc.), skin patches (such as patches available from MC10 Inc., etc.), smart clothing with integrated sensors, and implants with integrated sensors (e.g., integrated sensors available from CardioMEMS, Inc.). Examples of the passive data include range of motion, movement tracking, posture, pain levels, bone fusion measures, medication consumption, heart rate, pulse, sleep patterns, etc.

The application and location of material applied or delivered to the patient can be tracked by the patient monitoring module 244. For example, the intraoperative location of an implant, e.g., a spinal interbody fusion implant, can be recorded and compared to data recorded post-operatively or at follow-up visit(s) to determine if the implant is trending to be move or migrating to an undesirable position. Prior to catastrophic outcomes, the patient's rehabilitation regime can be re-directed and/or a revision surgery can be performed. Additionally, an implant can be configured to be adjusted from outside the patient without re-operation through, e.g., radi signals and the use of rare earth magnets built into the implant, which can allow implant height or lordosis to be adjusted in order to compensate for movement of the implant or subsidence. The expansion of the implant can help to restore lordosis, balance, or decompression, for example.

Also similar to that discussed above regarding the treatment compliance module 216, the patient monitoring module 244 can be configured to analyze received compliance data to determine a compliance level and/or a success rate of the treatment overall and/or per symptom, can be configured to compare received post-op treatment compliance data for a patient with historic compliance data for other patients who underwent similar post-op treatment to help determine the effectiveness of the treatment for the patient, and can be configured to receive data submitted by patients and users other than patients for storage in the treatment plan database 328. Users can submit data to the patient monitoring module 244 similar to that discussed above regarding submission of data to the diagnosis module 210 and the treatment compliance module 216. The analysis and/or comparison performed by the patient monitoring module 244 can consider data regarding the patient's specific post-op recovery targets as stored in the patient targets database 330, and/or can consider data regarding post-op recovery targets for typical patients having received a same type of surgery as the patient as stored in the surgery targets database 332.

The patient monitoring module 244 can be configured to provide a user with information regarding a patient's post-op treatment plan, such as by displaying post-op treatment plan information on a device in communication with the system 10. Non-limiting examples of post-op treatment plan information that can be displayed on the device include reminders for upcoming post-op appointments (e.g., physical therapy appointments), reminders of days/times to take medication, percentage of overall compliance with the post-op treatment plan, reminders to upload data (e.g., video of exercise, blood pressure and/or other vital sign reading, etc.), current list of symptoms and/or pain levels, etc.

FIG. 28 illustrates an embodiment of post-op treatment plan display to a user 150 on a display device 152 in communication with the system 10. Although the display device 152 is a touch screen tablet in the illustrated embodiment, the system 10 can communicate with other devices, as discussed above. Similarly, although the post-op treatment plan displayed on the display device 152 in the illustrated embodiment includes a calendar indicating days to take medication and a graph indicating overall compliance with the post-op treatment plan, any combination of different types of information can be shown on a display device in communication with the system 10. The displayed information can be customized by a user so that the user can receive the most relevant information for their particular post-op treatment plan. Providing feedback on a post-op treatment plan to a patient undertaking the plan can help encourage the patient's compliance with the plan because progress can be continually, visibly observed, and because healing and resumption of normal activity can be shown as an obtainable goal.

Efficacy Analysis Module

The efficacy analysis module 246 can provide users of the system 10 with an interface for reviewing data gathered and analyzed by the recovery module 208 regarding the patient's post-surgery recovery. Similar to that discussed above regarding the treatment compliance module 216, the patient monitoring module 244 can be configured to continually analyze received data to help determine the efficacy of a particular patient's post-op treatment plan in achieving the desired functional outcome, and/or to help monitor the patient's general health. This monitoring can be performed actively or passively methods, similar to that discussed above. The patient monitoring module 244 can thus determine that a particular patient's post-op treatment plan should be modified based on comparison of the effectiveness of the treatment plan in helping the patient reach their interim or final recovery targets set by their surgeon and/or when compared to the aggregate of other patients' data having similarities in multiple factors as determined by the system 10 for a high correlation factor, such as procedure type, patient age, bone density, spinal levels treated, etc. The patient monitoring module 244 can learn from other patients' experiences that the present patient's post-op treatment could benefit from a modification, e.g., perform a specific exercise once every other day instead of once daily, cease performance of a particular exercise, decrease salt intake, wear a knee brace 24/7 instead of only while sleeping, add or change medication type and dosage, etc. Thus, the predicted outcome of rehabilitation and treatment can be predicted for the patient if they continue therapies that historical patients have followed. This can increase patient compliance to rehabilitation therapies if the patient can compare their performance to others that have had the same procedure and similar rehabilitation therapy. The patient monitoring module 244 can be configured to suggest the modification of the patient's treatment post-op plan to the patient's care provider, e.g., by providing an alert to the care provider indicating that modification of the patient's post-op treatment plan is recommended. The care provider can review the modification and determine whether to modify the patient's treatment plan. Alternatively, the patient monitoring module 244 can be configured to automatically modify the patient's post-op treatment plan and inform the patient via an alert as to the modified post-op treatment plan. Usually, however, a care provider would review a modification to check its appropriateness for the particular patient before the patient monitoring module 244 automatically modifies the patient's post-op treatment plan and informs the patient of the change. Data regarding efficacy of the patient's post-op treatment plan can be stored in the patient targets database 330. The care provider can compare treatment groups and redirect rehabilitation plans to those that have been determined to be most effective.

The efficacy analysis module 246 can be configured to capture the data collected in the operation module 204, the diagnosis and treatment module 200, and the operation module 204 in order to generate a comprehensive data set for each patient. The efficacy analysis module 246 can be configured to aggregate these data sets with other patient data sets. The data collected can be of high enough value such that when the data is combined using a sufficient quantity of patients, the result is a study that could be published in a peer-reviewed medical journal for the purpose of sharing the outcomes of a certain procedure or treatment type with a selected patient group. The efficacy analysis module 246 can be configured to analyze the collected data to determine variables that may enhance or reduce patient compliance, with insights used to modify patient compliance with one or more compliance enhancers such as reward programs and patient support communities.

System Use

As mentioned above, the systems and methods of using the systems described herein can be used through a medical treatment continuum of patient care. In an exemplary embodiment, the system can be provided throughout an entirety of the treatment continuum of patient care, thereby maximizing opportunities for data collected during various portions of the continuum to be used in informing determinations made in any one or more other portions of the continuum. The system can, however, be provided for only a partial portion of the continuum. The system can be flexibly implemented using any one or more modules thereof in any combination. The system can thus be configured to accommodate different monetary cost constraints, different availabilities of computer infrastructure, and different end user needs. For example, only a diagnosis and treatment module of the system can be provided to facilitate diagnosing patients and determining treatments for the patients based on the diagnoses. For another example, only pre-op and post-op modules of the system can be provided to facilitate the planning and performance of surgical procedures.

FIGS. 34A-42B illustrate exemplary embodiments of using the system 10 in various portions of the medical treatment continuum. Although the methods are illustrated with respect to the system 10 of FIG. 2, any of the systems disclosed herein can be similarly used. Also, although various ones of the methods are illustrated with respect to a spinal surgical procedure, the systems disclosed herein can be used with respect to any type of surgical procedure, as discussed above.

Figure 34A:
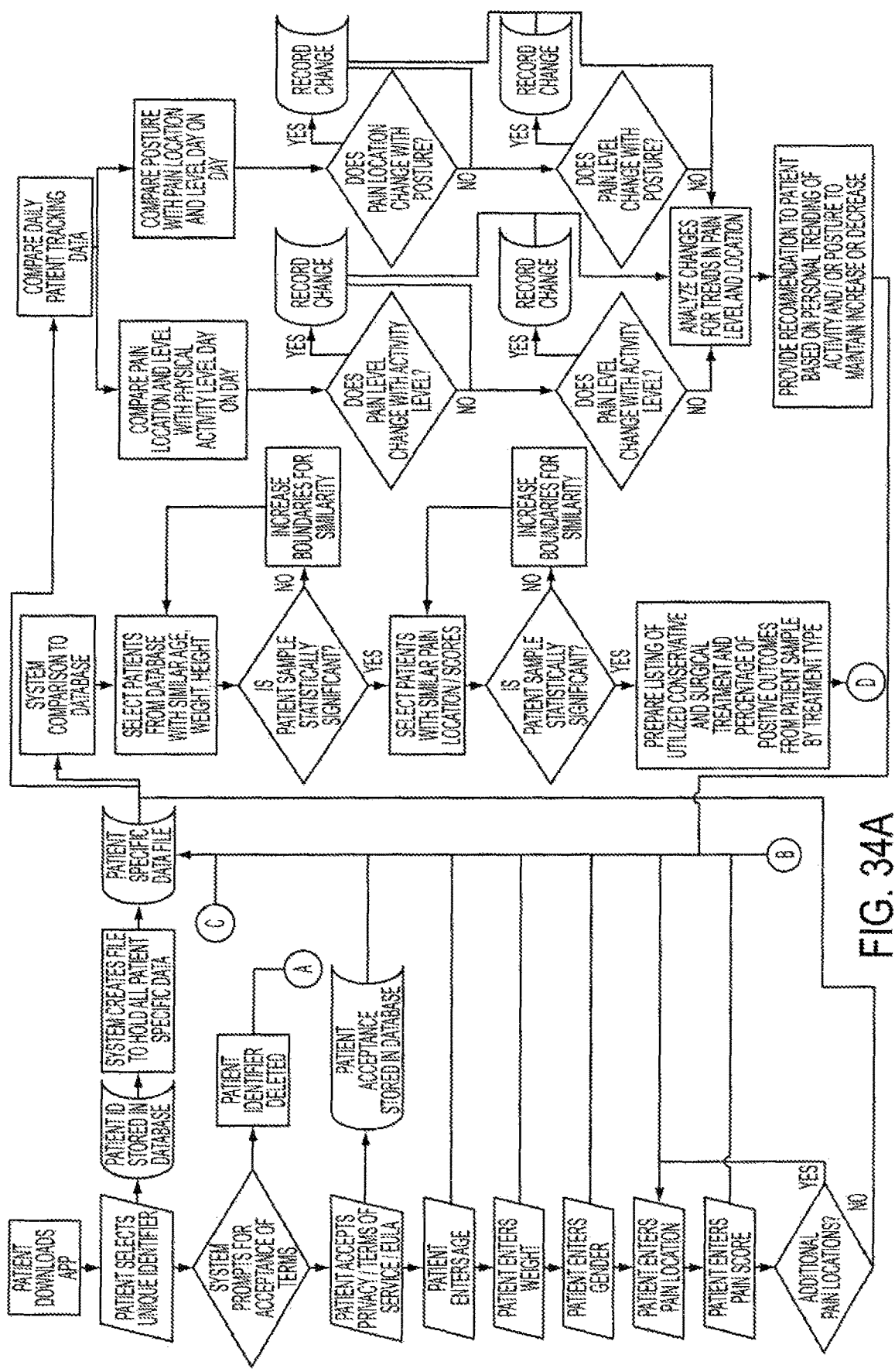
FIG. 34A shows a flowchart of an exemplary embodiment of using a diagnosis and treatment module of the diagnosis, surgical planning, support, and management system of FIG. 2.
Figure 34B:
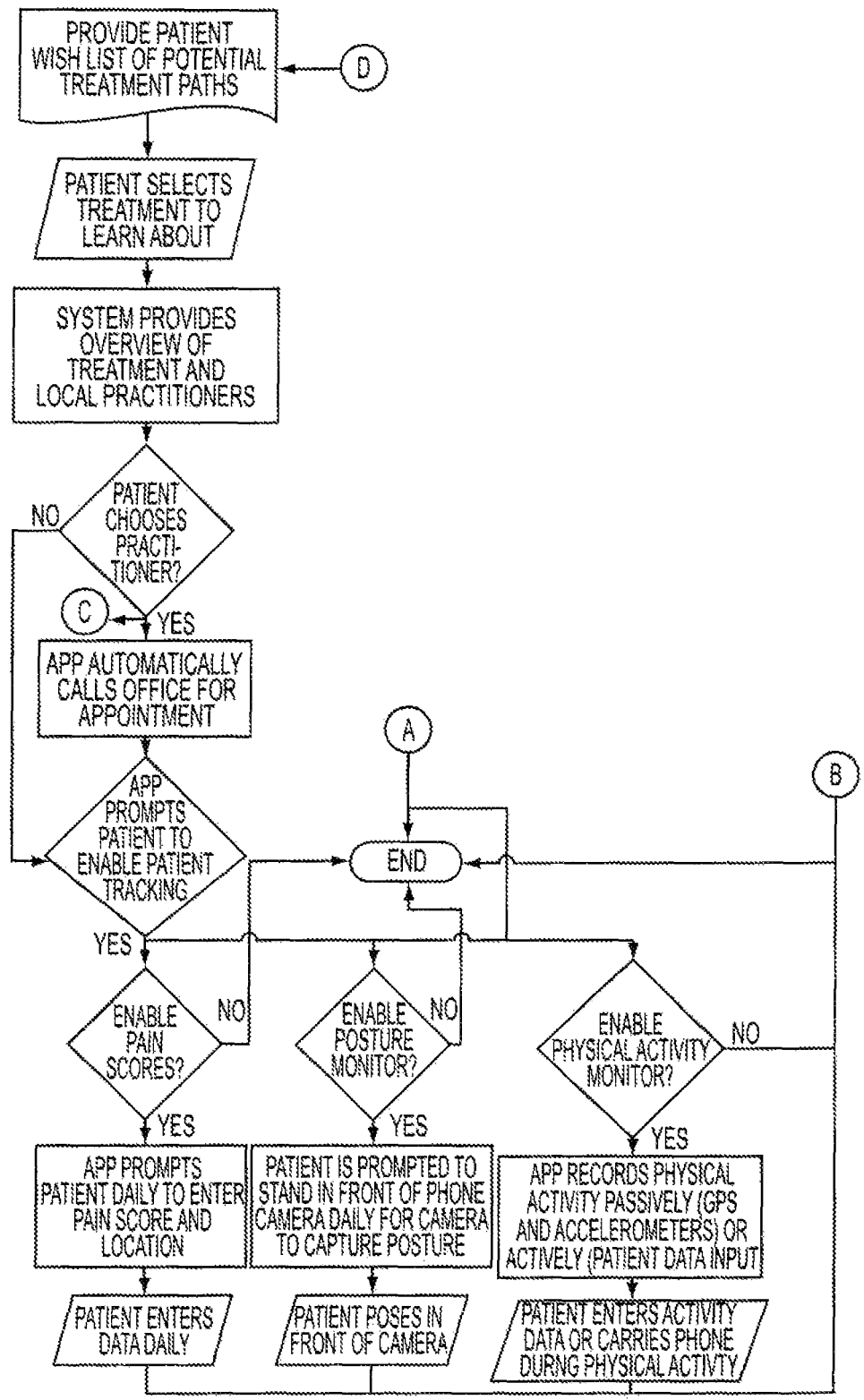
FIG. 34B shows another portion of the flowchart of FIG. 34A.
Figure 35:
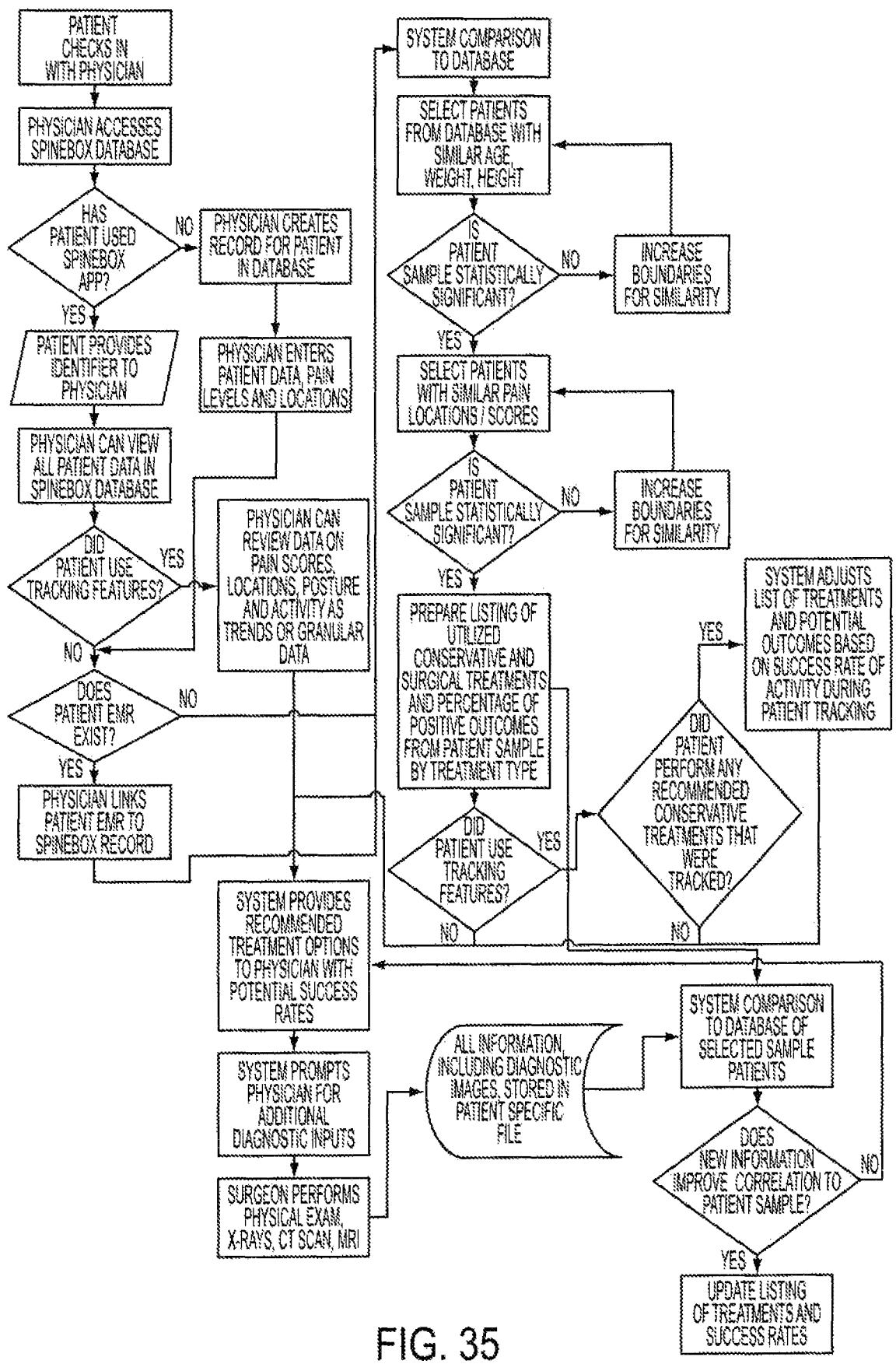
FIG. 35 shows a flowchart of another exemplary embodiment of using a diagnosis and treatment module of the diagnosis, surgical planning, support, and management system of FIG. 2.
Figure 36:
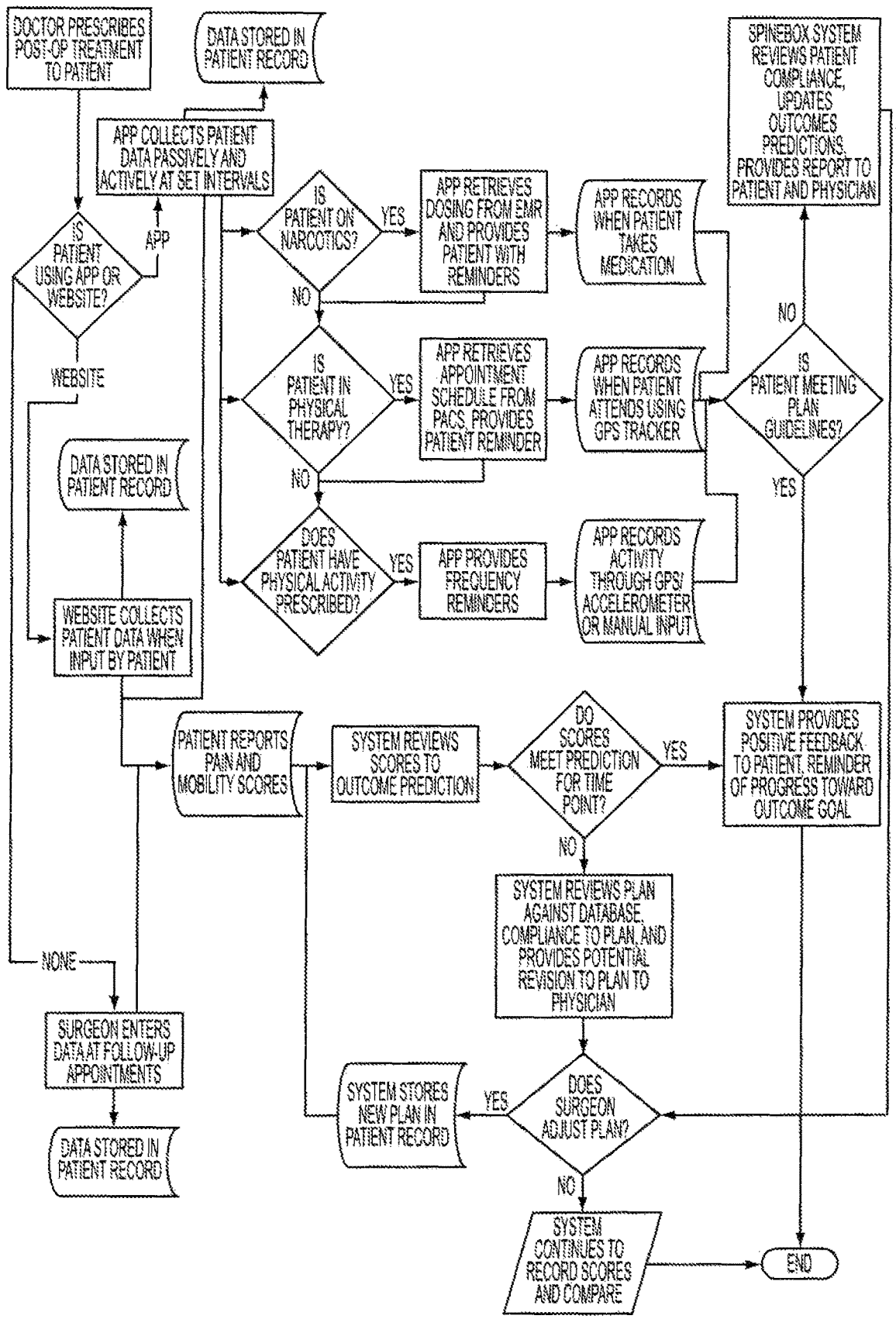
FIG. 36 shows a flowchart of another exemplary embodiment of using a diagnosis and treatment module of the diagnosis, surgical planning, support, and management system of FIG. 2.
Figure 37:
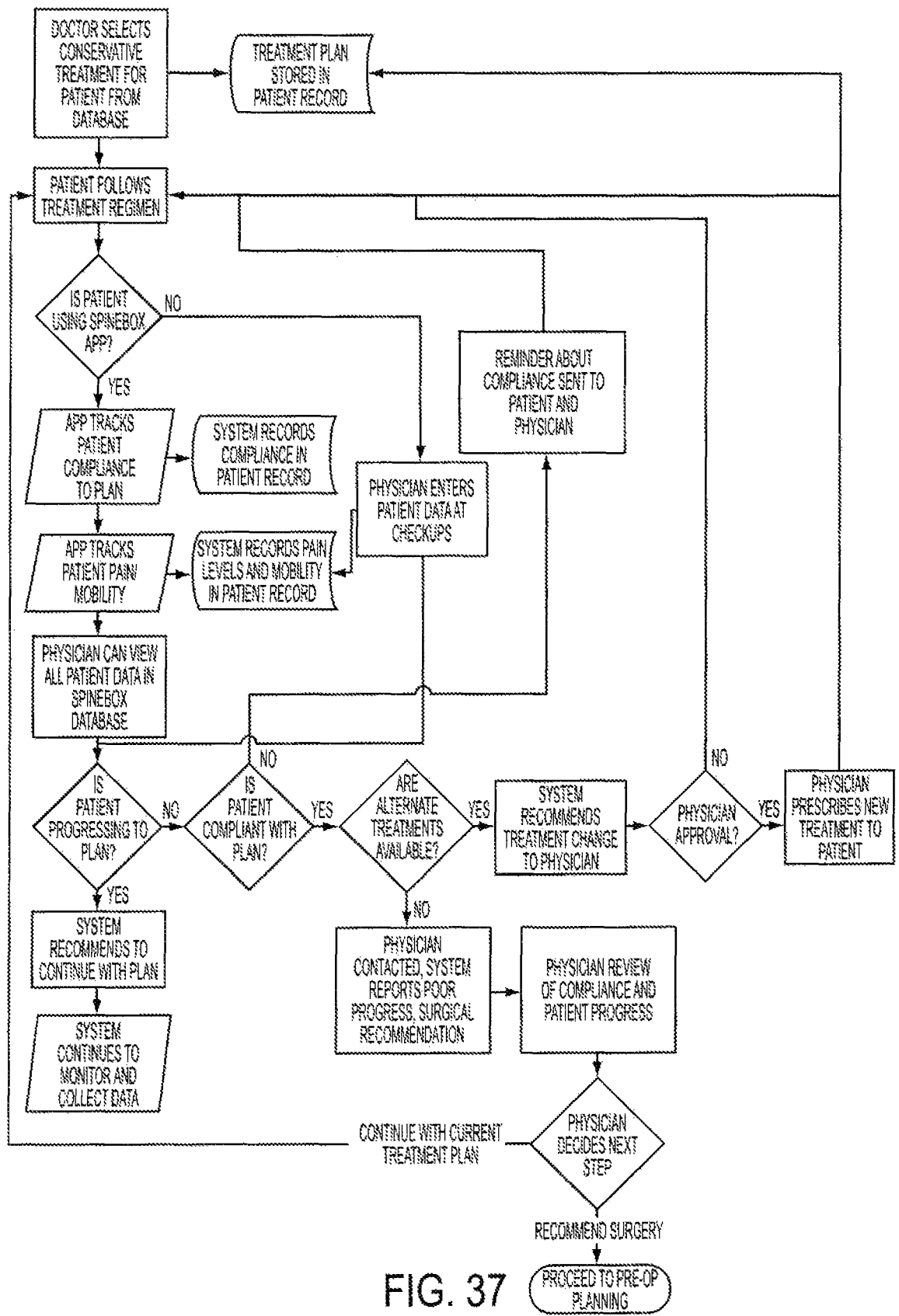
FIG. 37 shows a flowchart of another exemplary embodiment of using a diagnosis and treatment module of the diagnosis, surgical planning, support, and management system of FIG. 2.
Figures 1, 38:
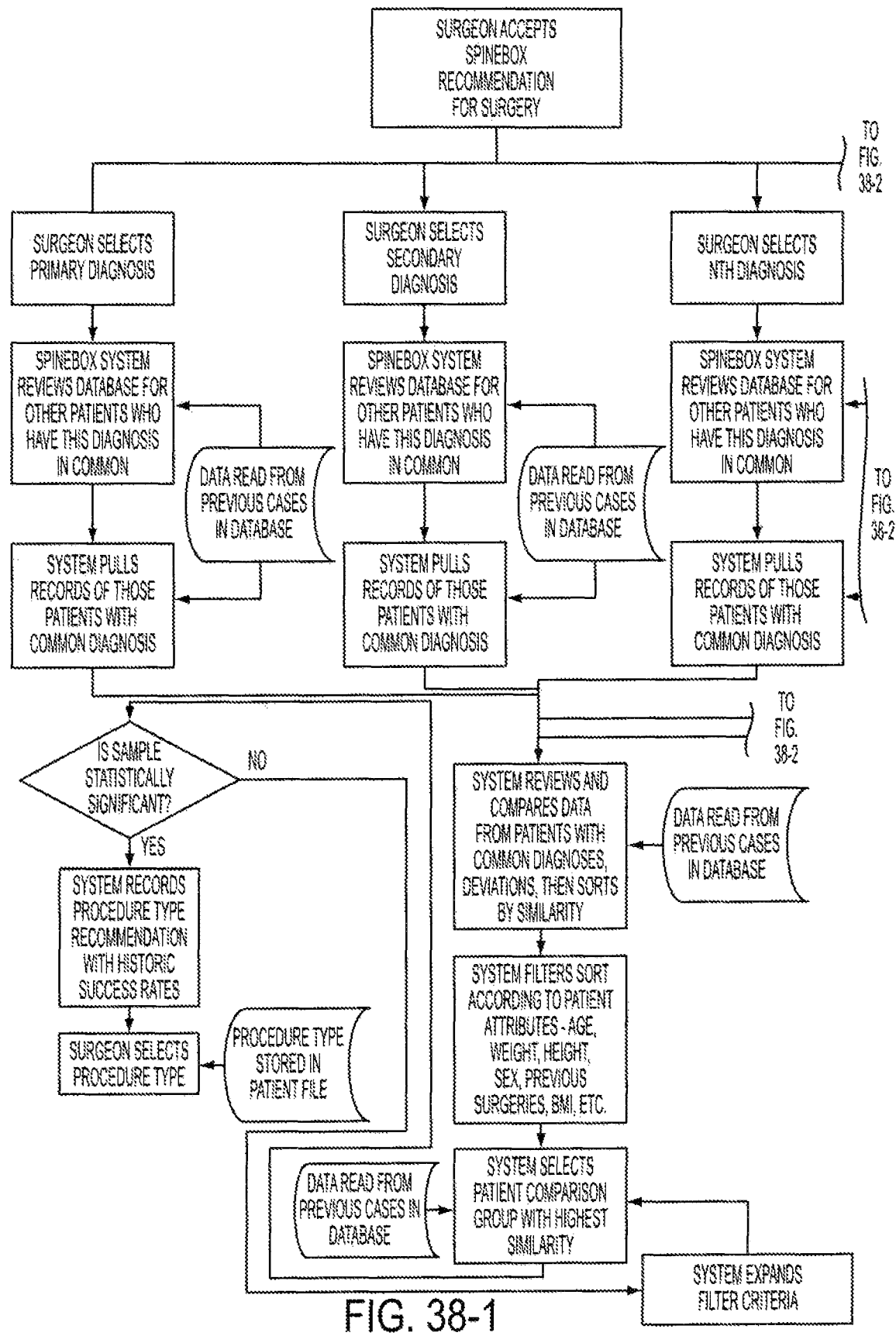
Figures 2, 38:
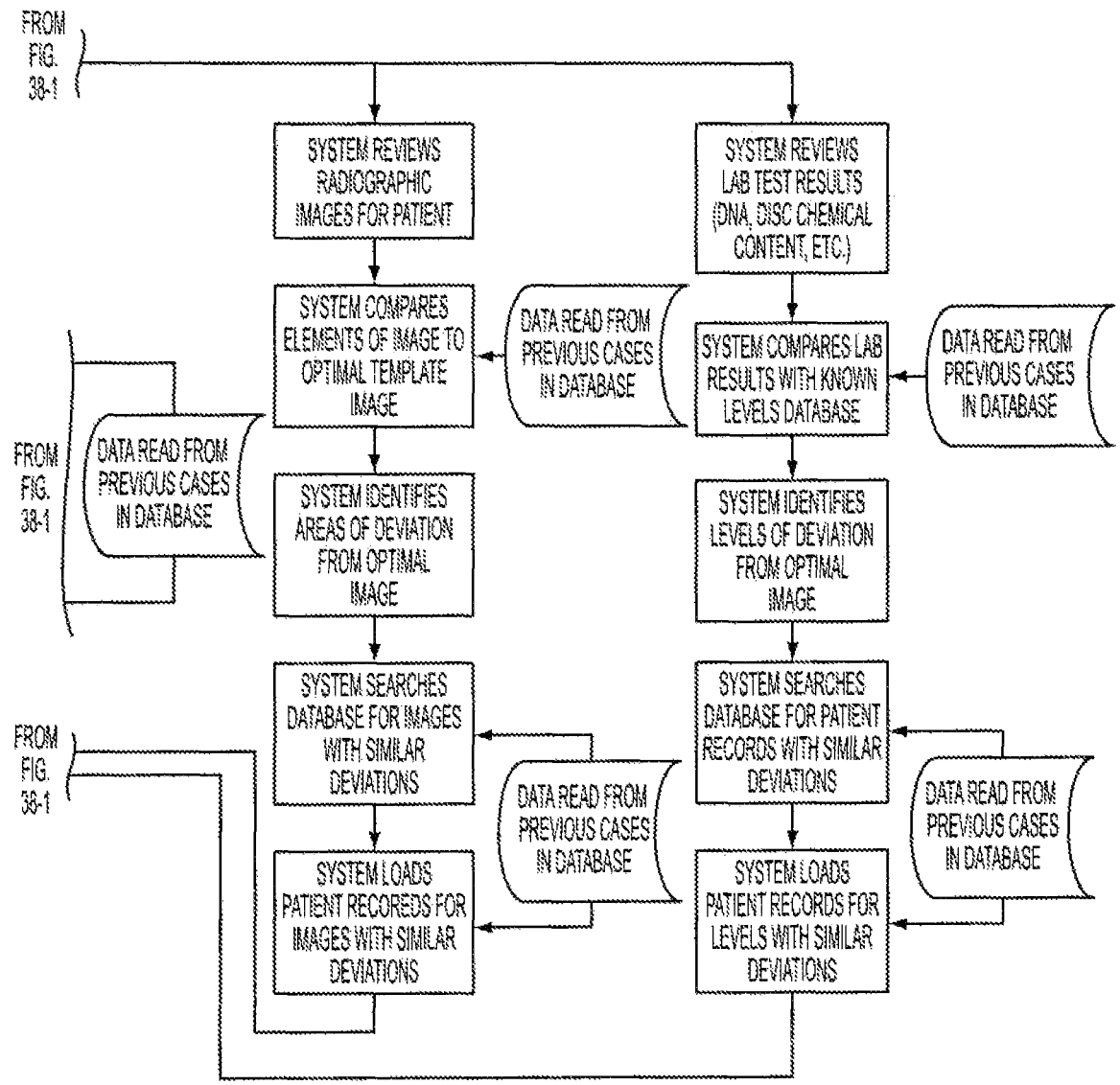
Figures 1, 39A:
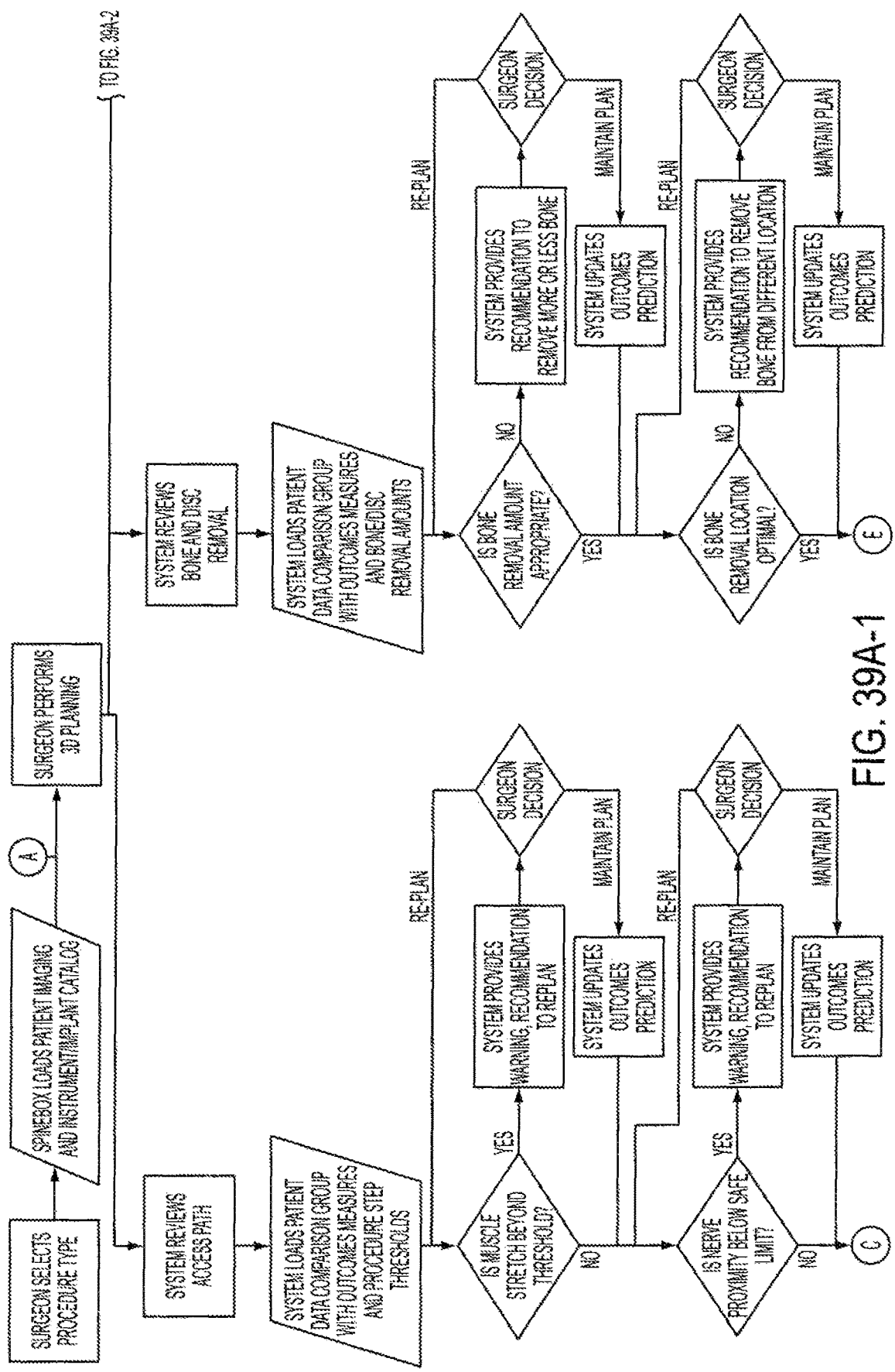
Figures 2, 39A:
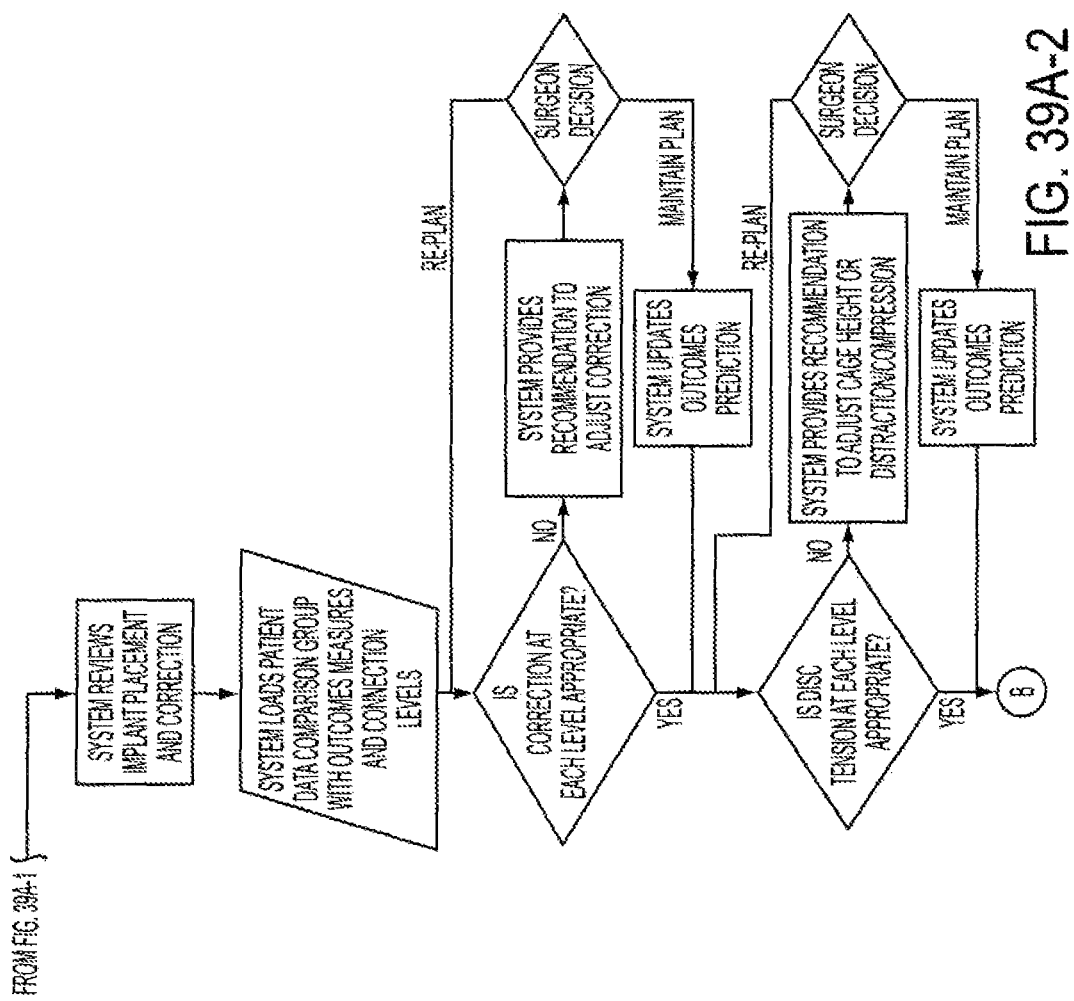
Figures 2, 39B:
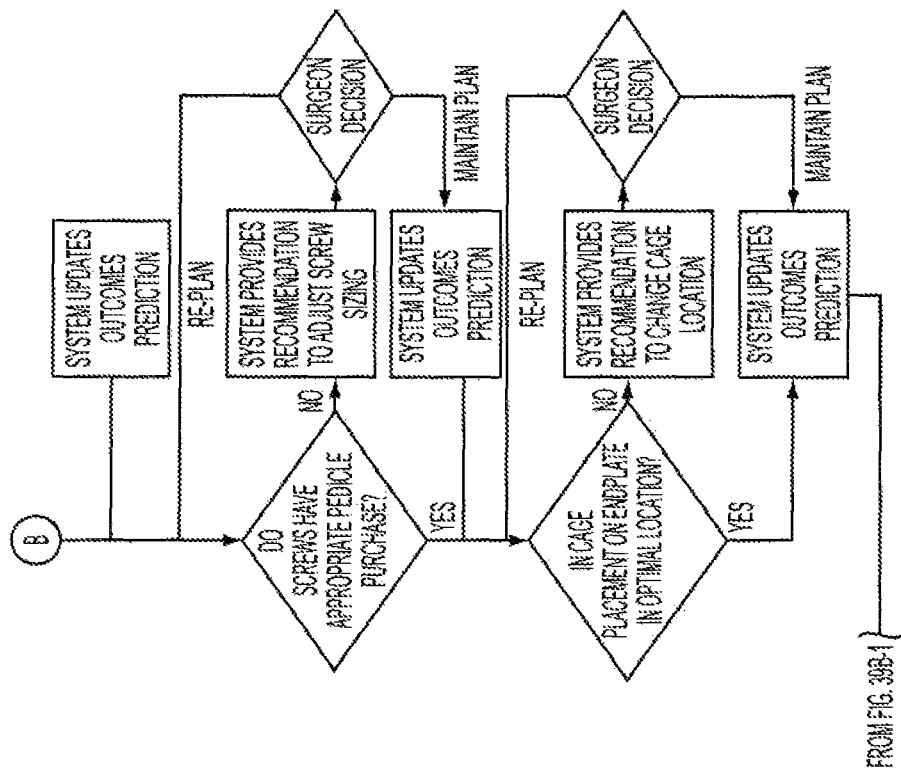
Figures 3, 39B:
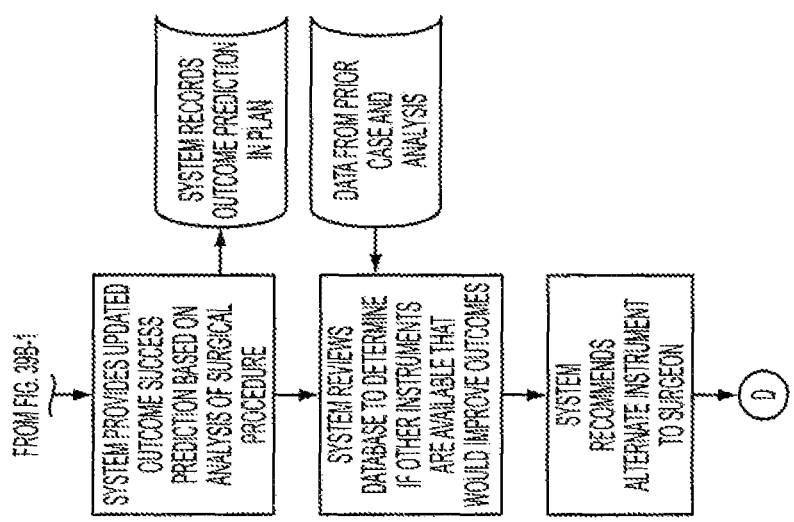
Figure 39C:
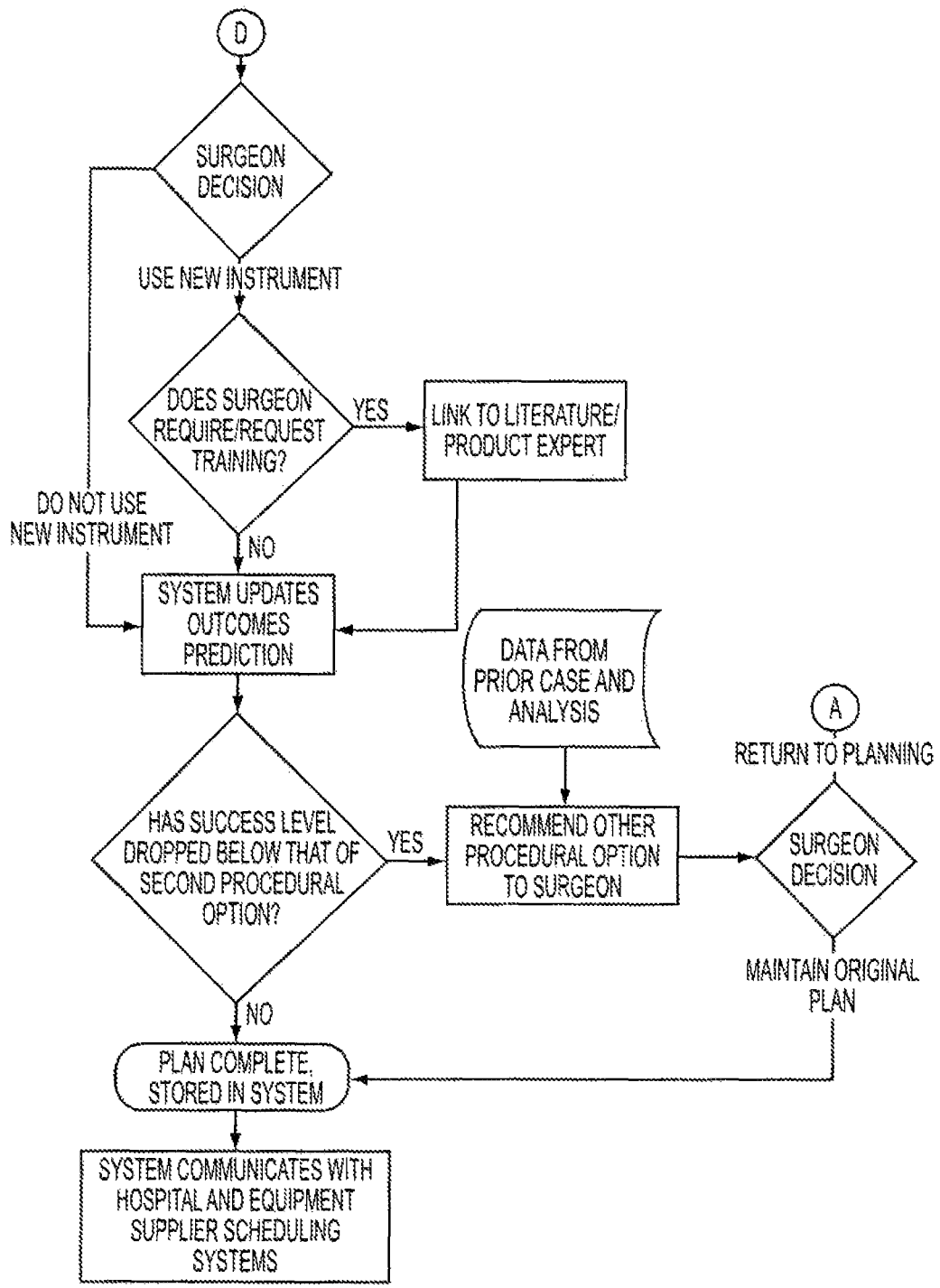
FIG. 39C shows another portion of the flowchart of FIG. 39A-1.
Figure 40:
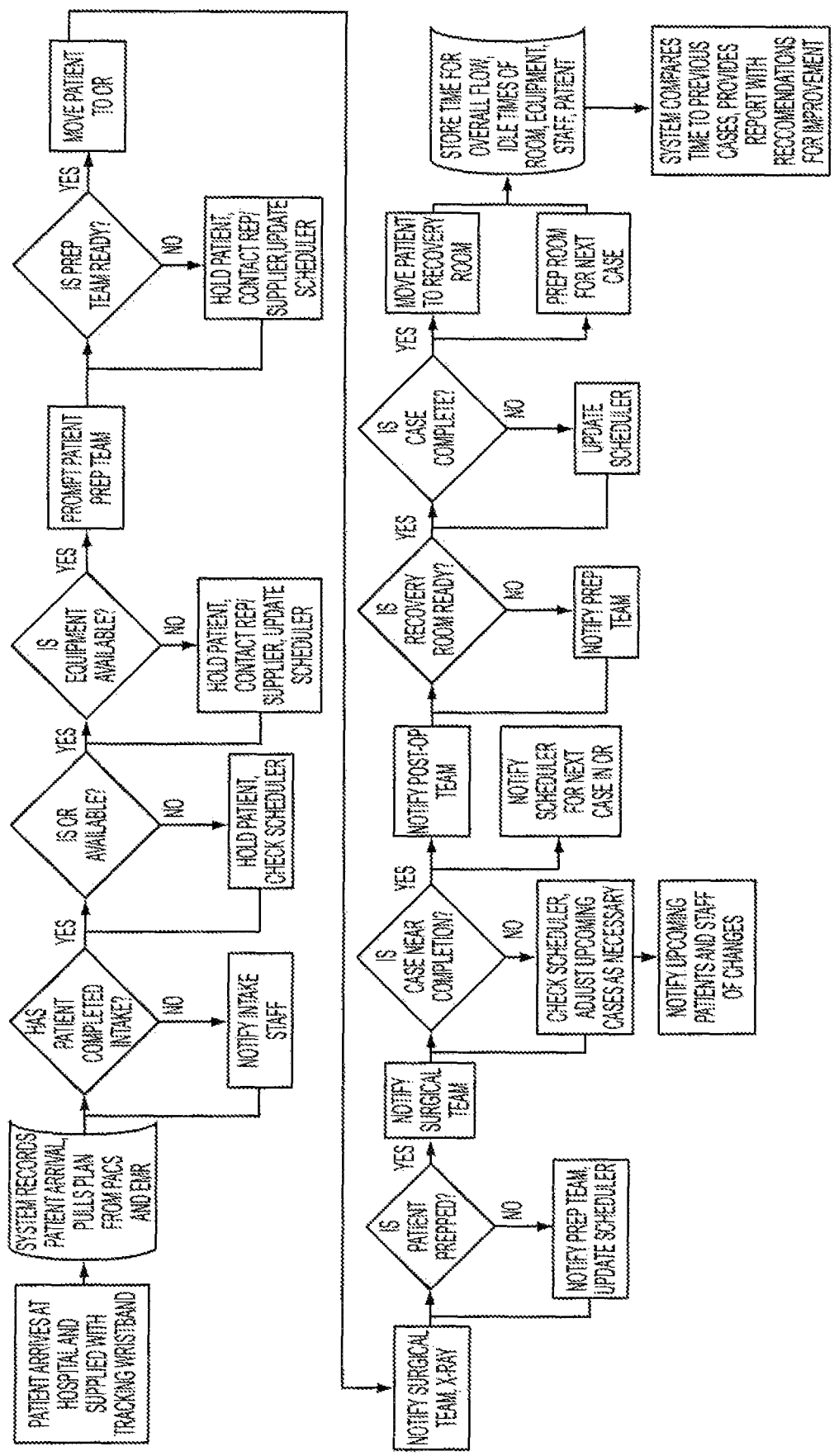
FIG. 40 shows a flowchart of another exemplary embodiment of using a pre-op module of the diagnosis, surgical planning, support, and management system of FIG. 2.
Figure 41A:
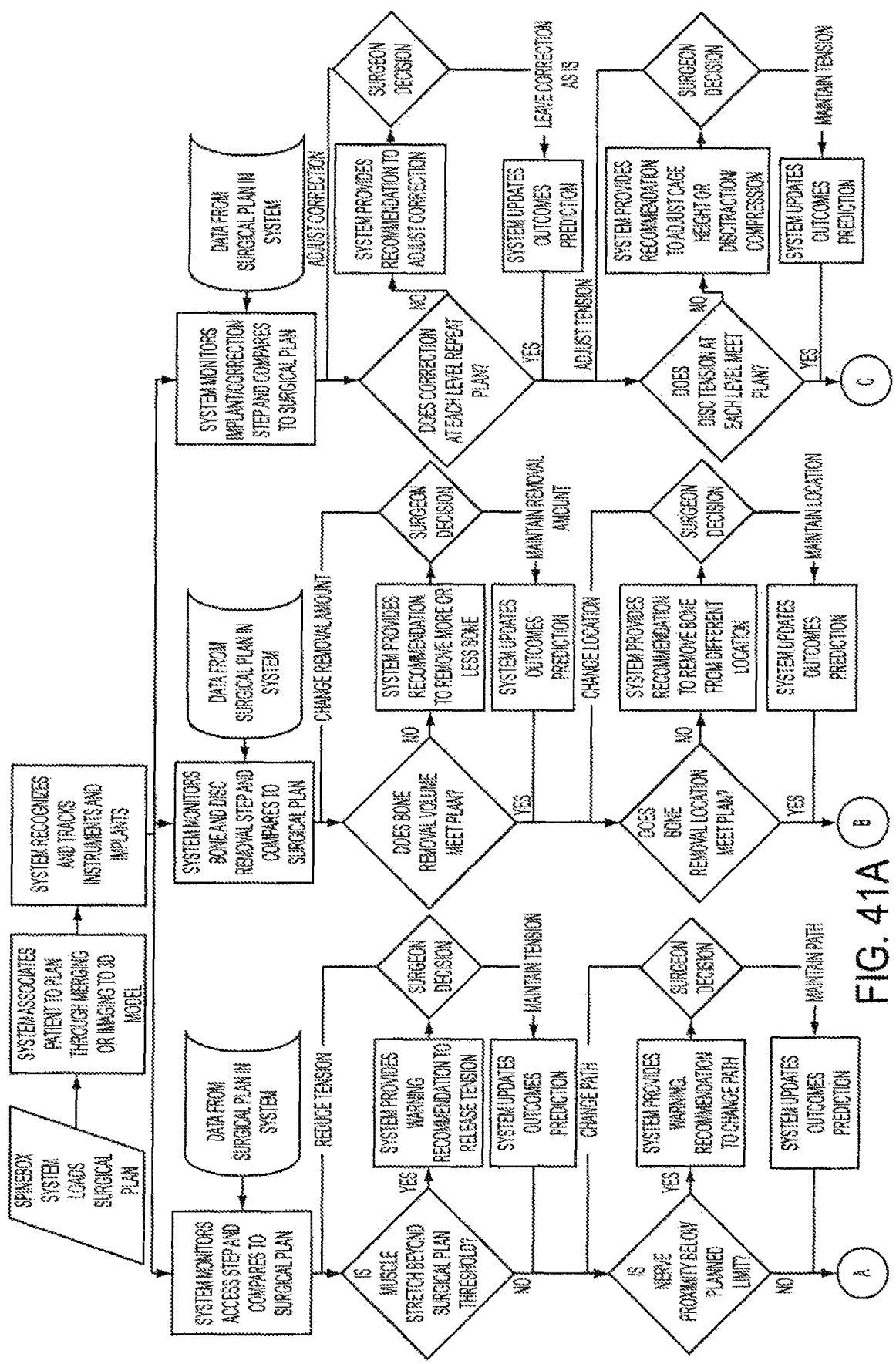
FIG. 41A shows a flowchart of an exemplary embodiment of using an operation module of the diagnosis, surgical planning, support, and management system of FIG. 2.
Figures 1, 41B:
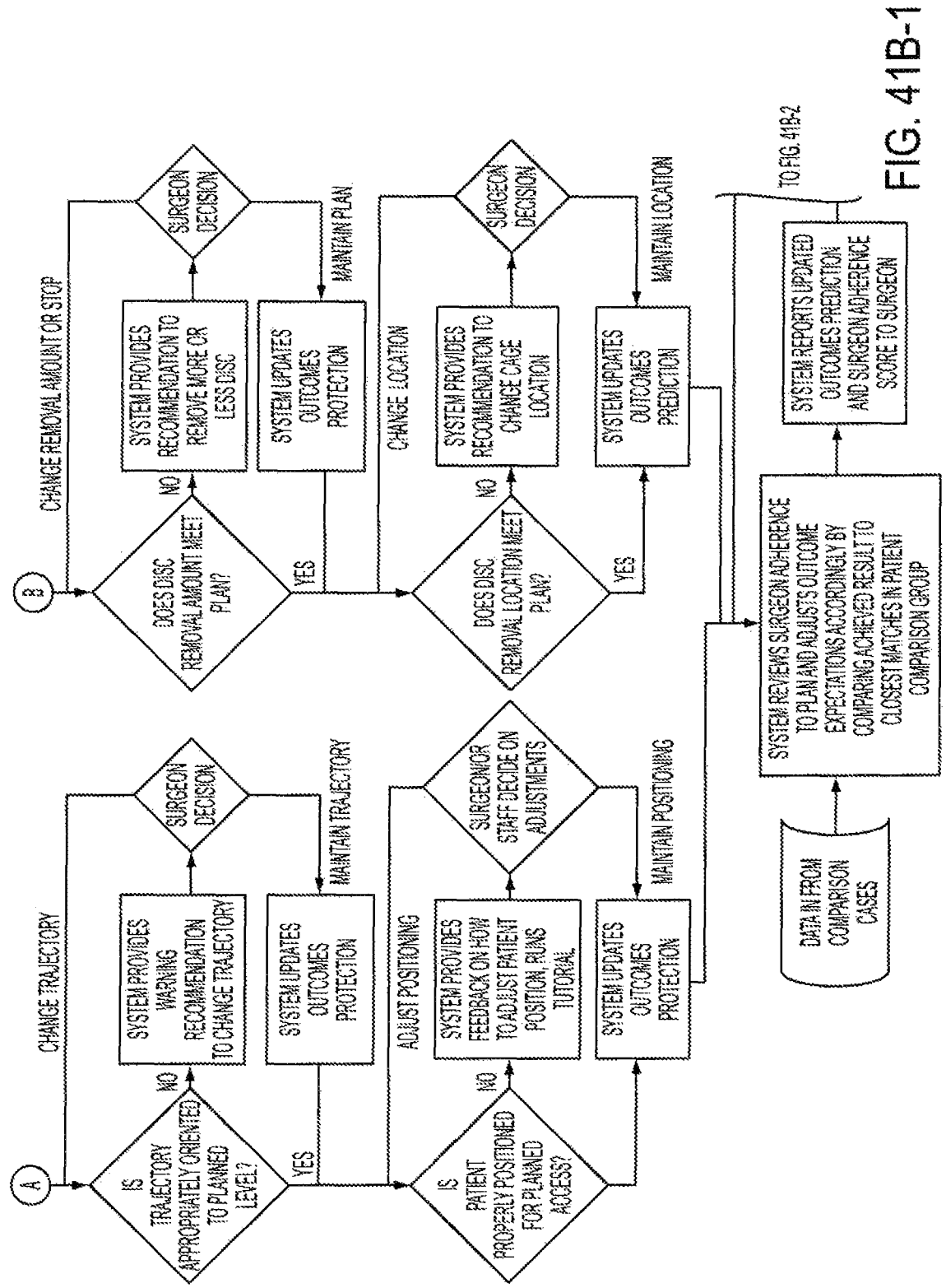
Figures 2, 41B:
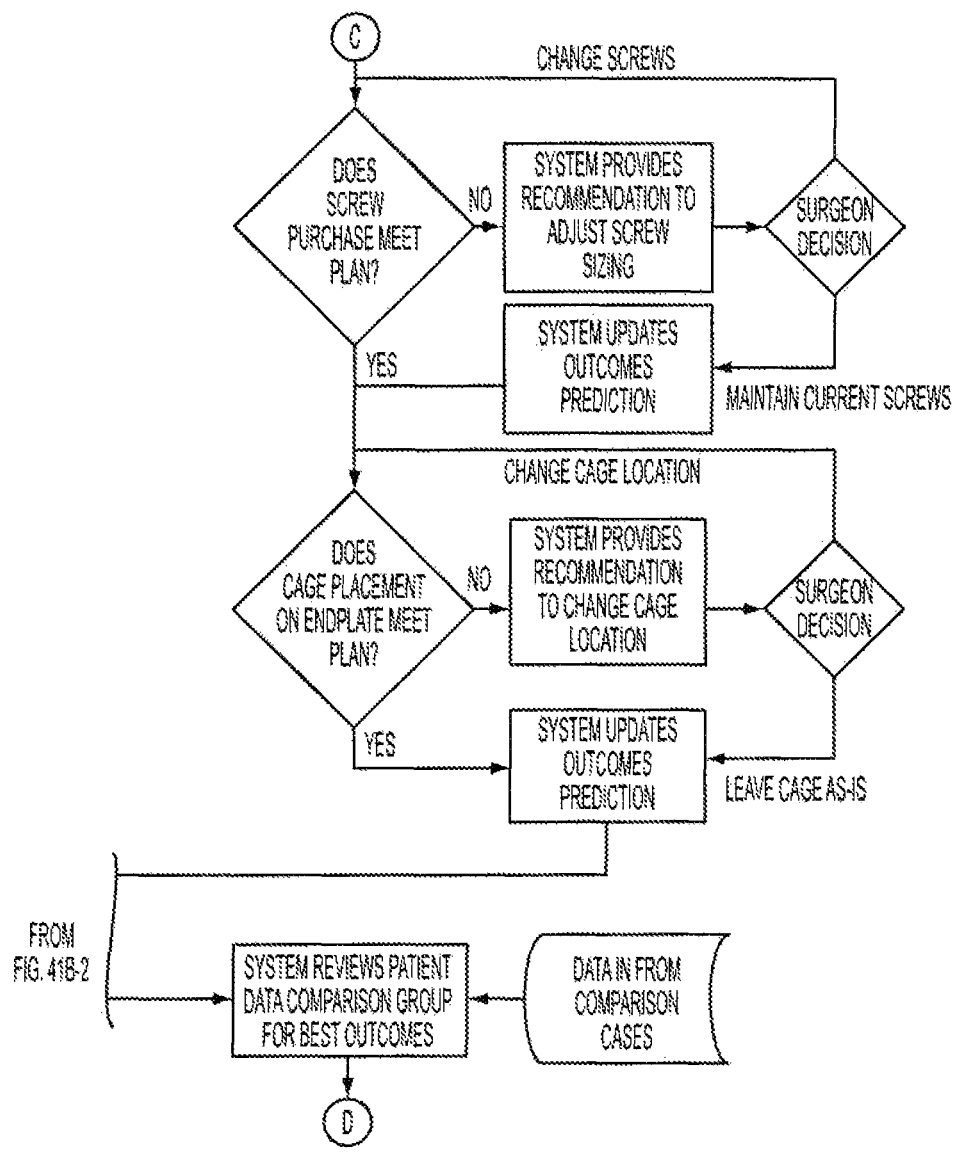
Figure 41C:
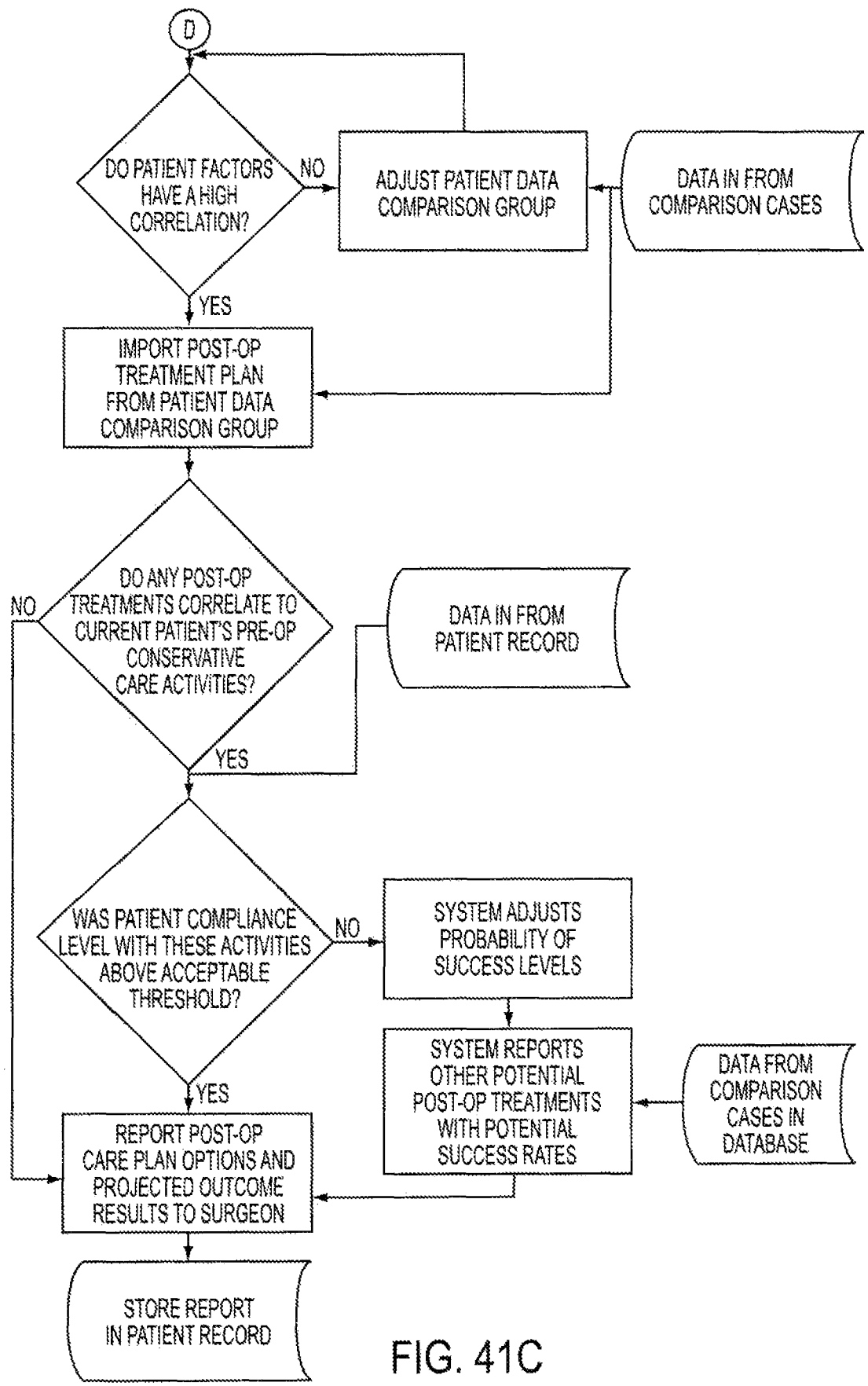
FIG. 41C shows another portion of the flowchart of FIG. 41A.
Figure 42A:
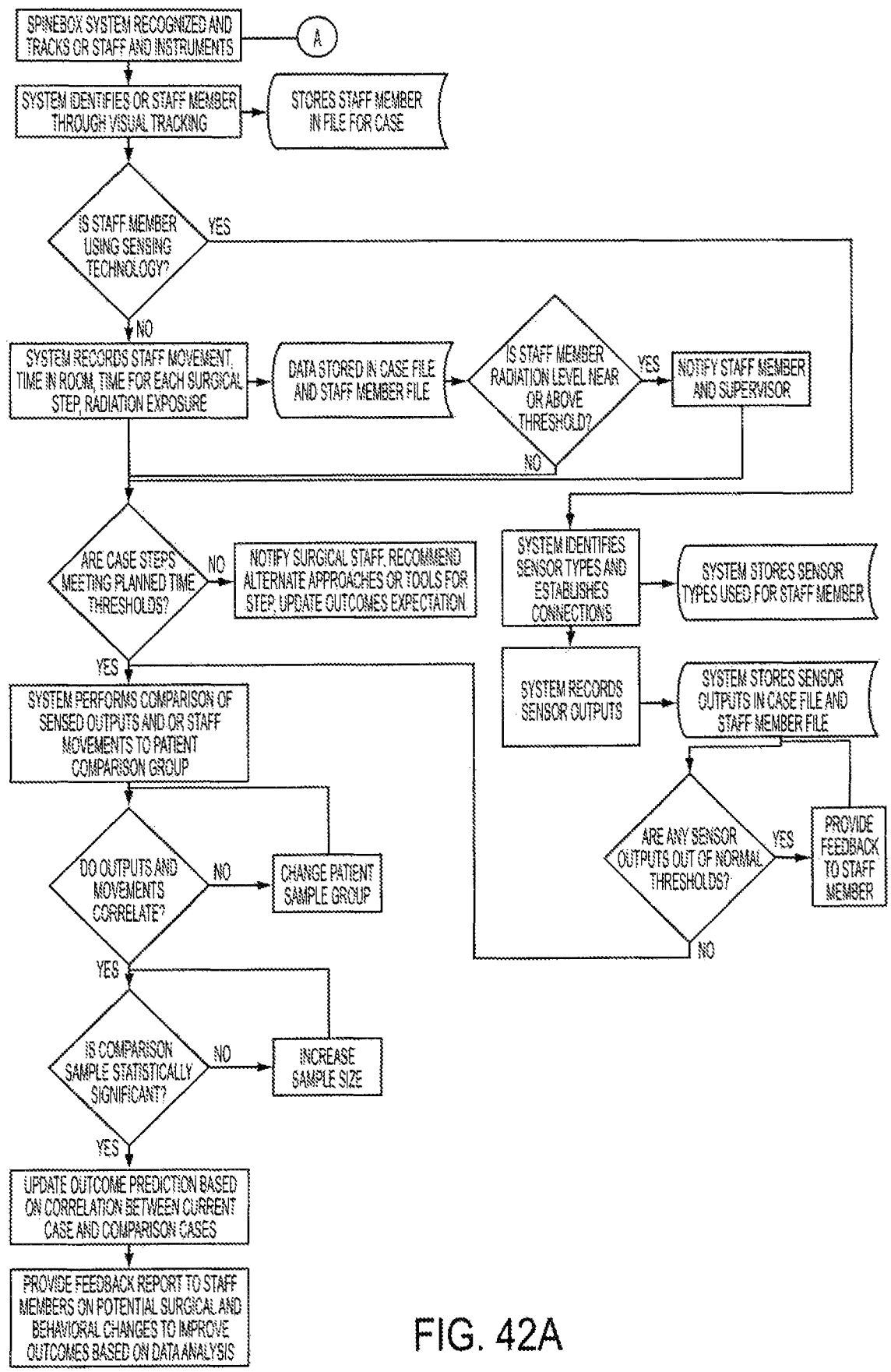
FIG. 42A shows a flowchart of another exemplary embodiment of using an operation module of the diagnosis, surgical planning, support, and management system of FIG. 2.
Figure 42B:
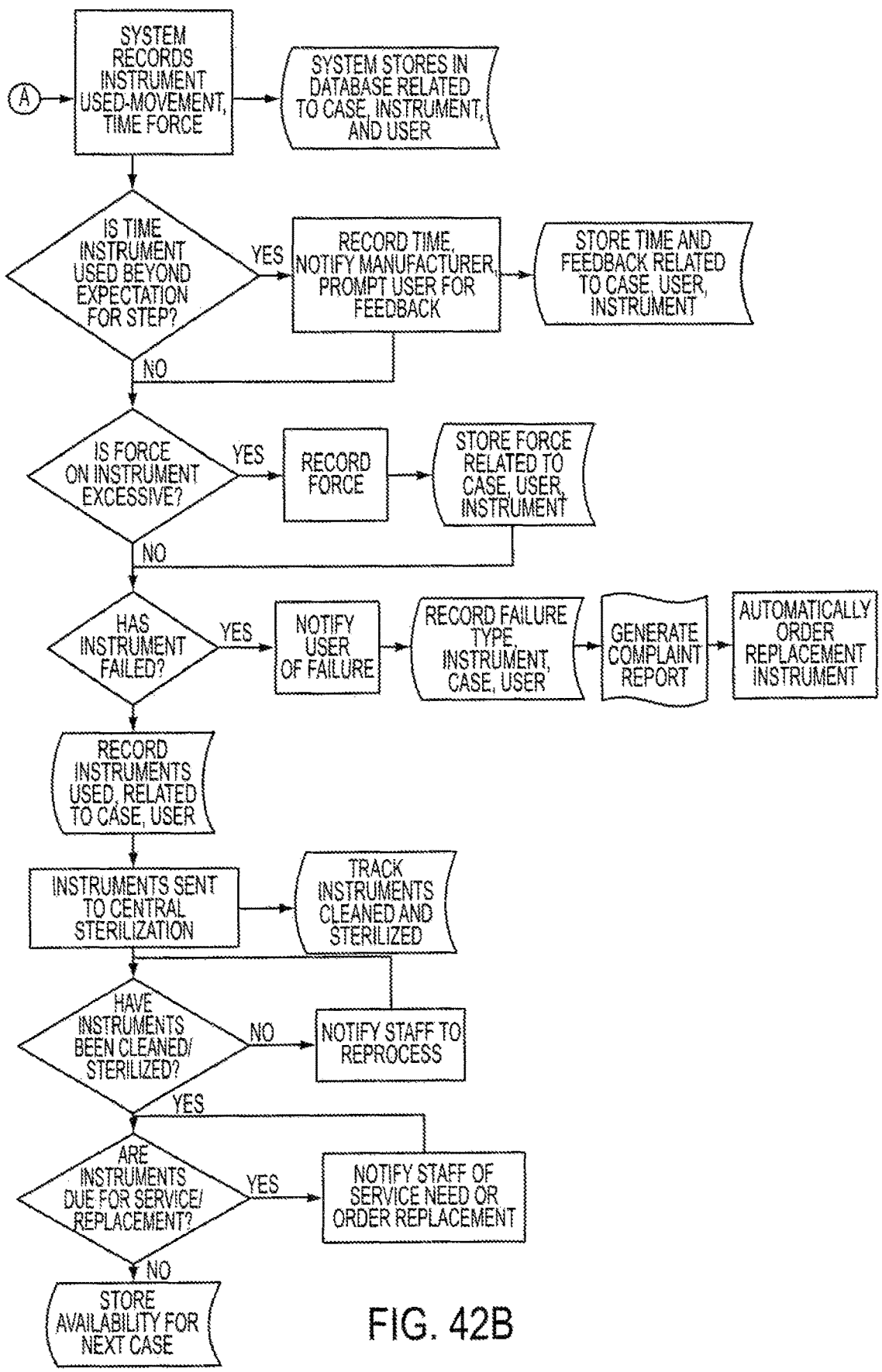
FIG. 42B shows another portion of the flowchart of FIG. 42A.

FIGS. 34A-34B illustrate an exemplary embodiment of a use of the diagnosis and treatment module 200, and in particular the diagnosis module 210. FIG. 35 illustrates another exemplary embodiment of a use of the diagnosis and treatment module 200, and in particular the treatment options module 212. FIG. 36 illustrates another exemplary embodiment of a use of the diagnosis and treatment module 200, and in particular the treatment compliance module 216. FIG. 37 illustrates another exemplary embodiment of a use of the diagnosis and treatment module 200, and in particular the treatment compliance module 216. FIG. 38 illustrates an exemplary embodiment of a use of the pre-op module 202, and in particular the surgical procedure planning module 218. FIGS. 39A-39C illustrate another exemplary embodiment of a use of the pre-op module 202, and in particular the surgical procedure planning module 218. FIG. 40 illustrates another exemplary embodiment of a use of the pre-op module 202, and in particular the scheduling module 222 and the patient preparation module 224. FIGS. 41A-41C illustrate an exemplary embodiment of a use of the operation module 204, and in particular the procedure analysis module 230. FIGS. 42A-42B illustrate another exemplary embodiment of a use of the operation module 204, and in particular the equipment tracking module 232 and the personnel tracking module 236.

CONCLUSION

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical method, comprising:
a processor receiving plan data regarding a virtual performance of a particular surgical procedure on a patient, the virtual performance being a simulation of the particular surgical procedure on a three-dimensional simulated model of the patient using virtual surgical instruments;
the processor receiving performance data regarding an actual performance of the particular surgical procedure on the patient, the performance data being received in real time during the actual performance of the surgical procedure, and the virtual performance of the surgical procedure having been performed and completed prior to a start of the actual performance of the surgical procedure on the patient;
the processor determining deviation between the plan data and the performance data;
if the plan data is determined to deviate from the performance data outside a predetermined degree of tolerance, the processor providing a warning to a user that includes an indication of the determined variance, and the processor receiving subsequent performance data in real time during the actual performance of the surgical procedure and determining deviation between the plan data and the subsequently received performance data; and
if the plan data is determined to deviate from the performance data within the predetermined degree of tolerance, the processor receiving subsequent performance data in real time during the actual performance of the surgical procedure and determining deviation between the plan data and the subsequently received performance data;
wherein the patient is on a bed Burin the actual performance of the surgical procedure;
the surgical procedure Is a spinal surgical procedure;
the method further comprises, upon determining that the plan data deviates from the performance data outside a predetermined degree of tolerance, the processor causing the bed to move so as to position the patient in the desired position;
the desired position aligns a vertebra of patient for a trajectory of approach;
the method further comprises the processor receiving, from a head-mountable stereoscopic viewing device worn by the surgeon, an input indicative of the surgeon desiring the patient to be in a second desired position; and
the method further comprises the processor causing the bed to move so as to position the patient in the second desired position; and
the second desired position aligns a second vertebra of the patient for a trajectory of posterior approach.

2. The method of claim 1, further comprising:
the processor receiving plan data regarding a plurality of virtual performances of the surgical procedure on a plurality of patients;
the processor receiving performance data regarding a plurality actual performances of the surgical procedure on the plurality of patients in real time with the actual performances of the surgical procedures;
the processor determining if the plan data regarding the plurality of virtual performances varies from the performance data regarding the plurality actual performances;
the processor determining if any one or more of the determined variances are a same type of variance; and
the processor providing a recommendation to a user performing another virtual performance of the surgical procedure based on the one or more determined variances determined to be the same type of variance.

3. The method of claim 1, wherein the indication of the determined deviation includes a recommended course of action to match the actual performance of the surgical procedure to the virtual performance of a surgical procedure.

4. The method of claim 1, wherein a type of the received performance data comprises at least one of data regarding movement of a surgical instrument being used in the actual performance of the surgical procedure, movement of staff present for the actual performance of the surgical procedure, patient vital signs, identification of a surgical instrument being used in the actual performance of the surgical procedure, identification of staff present in the actual performance of the surgical procedure, an amount of tissue retraction, a duration of tissue retraction, and one or more real time images of the patient acquired during the actual performance of the surgical procedure; and a type of the received plan data corresponds to the type of the received performance data.

5. The method of claim 1, wherein the determined deviation comprises at least one of a surgical instrument being moved relative to the patient than in the actual performance of the surgical procedure different than movement of at least one of the virtual surgical instruments in the virtual performance of the surgical procedure, a surgical implant being used in the actual performance of the surgical procedure being implanted at a different location within the patient than the surgical implant used in the virtual performance of the surgical procedure, different radiation exposures in the actual performance of the surgical procedure and the virtual performance of the surgical procedure, different lengths of tissue retraction time in the actual performance of the surgical procedure and the virtual performance of the surgical procedure, different pharmaceutical administration to the patient in the actual performance of the surgical procedure than in the virtual performance of the surgical procedure, a different number of staff being present in the actual performance of the surgical procedure than a number of virtual staff present in the virtual performance of the surgical procedure, a different duration of a step in the actual performance of the surgical procedure than in the virtual performance of the surgical procedure, a different surgical instrument being used in a step of the actual performance of the surgical procedure than in the virtual performance of the surgical procedure, and a step performed in the virtual performance of the surgical procedure not having been performed in the actual performance of the surgical procedure.

6. The method of claim 1, further comprising receiving input, from a user during performance of the actual surgical procedure, to a surgical instrument in electronic communication with the processor;

wherein one of the virtual surgical instruments corresponds to the surgical instrument.

7. The method of claim 6, wherein the plan data includes data indicative of virtual actions taken by the user via the corresponding virtual surgical instrument, the performance data includes data indicative of actual actions taken by a medical professional during the actual performance of the surgical procedure, and determining if the plan data varies from the performance data includes determining a variance of the virtual actions from the actual actions.

8. A medical system, comprising:

a storage device configured to store a pre-operative plan for a spinal surgical procedure to be performed on a patient, the plan including a desired position of the patient relative to a surgeon; and a processor configured to determine a position of the patient during setup for actual performance of the spinal surgical procedure on the patient, compare the determined position and the desired position to determine if a deviance exists between the determined position and the desired position, and provide user feedback in real time with the setup that is indicative of the deviation between the determined position and the desired position, the feedback including at least one of a visual signal, an auditory signal, and a motion signal;

wherein the patient is on a bed;

the processor configured to, upon determining a deviance between the determined position and the desired position, cause the bed to move so as to position the patient in the desired position;

the desired position aligns a vertebra of the patient for a trajectory of lateral approach;

the processor is configured to, in real time with the actual performance of the spinal surgical procedure on the patient and after the bed has been caused to move:

receive a user input indicative of surgeon desiring the patient to be in a second desired position;

cause the bed to move so as to position the patient in the second desired position; and the second desired position aligns a second vertebra of the patient for a trajectory of posterior approach.

9. The system of claim 8, wherein the desired position of the patient relative to the surgeon includes a desired position of a center of a vertebral disc of the patient straight down from a perspective of the surgeon.

10. The system of claim 8, further comprising an augmented reality reference marker configured to be positioned relative to the patient during the setup; and a camera configured to visualize the augmented reality reference marker during the setup and to communicate data regarding the visualization to the processor;

wherein the processor is configured to determine the position of the patient during setup using the data regarding the visualization.

11. The system of claim 8, further comprising a motor configured to be operatively coupled to the bed;

wherein the processor is configured to, if the deviance is determined to exist between the determined position and the desired position, actuate the motor and thereby cause the bed to move so as to position the patient in the desired position.

12. The system of claim 8, further comprising an inflatable brace configured to be operatively coupled to the bed;

wherein the processor is configured to, if the deviance is determined to exist between the determined position and the desired position, selectively inflate and deflate the brace and thereby cause the bed to move so as to position the patient in the desired position.

13. The system of claim 8, further comprising a head-mountable stereoscopic viewing device configured to receive the user input.

14. The system of claim 13, wherein the plan includes pre-surgical images of the patient; and the processor is configured to cause a display of the head-mountable stereoscopic viewing device to display the pre-surgical images data overlaid on the patient during the actual performance of the spinal surgical procedure on the patient.

15. The system of claim 8, wherein the plan includes a desired position of an instrument relative to the surgeon;

the processor is configured to determine a position of the instrument during the setup for the actual performance of the spinal surgical procedure on the patient, compare the determined position of the instrument and the desired position of the instrument to determine if a deviance exists between the determined position of the instrument and the desired position of the instrument, and provide user feedback in real time with the setup that is indicative of the deviation between the determined position of the instrument and the desired position of the instrument, the feedback including at least one of a visual signal, an auditory signal, and a motion signal.

16. The method of claim 1, wherein the processor causing the bed to move includes one of
actuating a motor operatively coupled to the bed, and
at least one of inflating and deflating an inflatable brace operatively coupled to the bed.

\* \* \* \* \*